(12) United States Patent
Higuchi et al.

(10) Patent No.: US 10,299,475 B2
(45) Date of Patent: May 28, 2019

(54) PESTICIDE

(71) Applicant: ISHIHARA SANGYO KAISHA, LTD., Osaka (JP)

(72) Inventors: Koji Higuchi, Shiga (JP); DamdinSuren Boldbaatar, Shiga (JP); Yuta Tazawa, Shiga (JP); Michiko Kanuma, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/911,642

(22) PCT Filed: Aug. 22, 2014

(86) PCT No.: PCT/JP2014/072041
§ 371 (c)(1),
(2) Date: Feb. 11, 2016

(87) PCT Pub. No.: WO2015/025960
PCT Pub. Date: Feb. 26, 2015

(65) Prior Publication Data
US 2016/0192651 A1    Jul. 7, 2016

(30) Foreign Application Priority Data

Aug. 23, 2013  (JP) ................... 2013-172954
May 15, 2014   (JP) ................... 2014-101799

(51) Int. Cl.
*A01N 37/22*   (2006.01)
*C07F 7/08*    (2006.01)
(Continued)

(52) U.S. Cl.
CPC ............ *A01N 37/22* (2013.01); *A01N 37/34* (2013.01); *A01N 37/38* (2013.01); *A01N 43/08* (2013.01); *A01N 43/10* (2013.01); *A01N 43/16* (2013.01); *A01N 43/18* (2013.01); *A01N 43/20* (2013.01); *A01N 43/30* (2013.01); *A01N 43/36* (2013.01); *A01N 43/38* (2013.01); *A01N 43/40* (2013.01); *A01N 43/90* (2013.01); *A01N 47/20* (2013.01); *A01N 55/00* (2013.01); *C07C 231/14* (2013.01); *C07C 235/42* (2013.01); *C07C 235/46* (2013.01); *C07C 235/84* (2013.01); *C07C 235/88* (2013.01); *C07C 237/30* (2013.01); *C07C 243/38* (2013.01); *C07C 255/29* (2013.01); *C07C 255/54* (2013.01); *C07C 271/28* (2013.01); *C07C 317/22* (2013.01); *C07C 323/18* (2013.01); *C07C 323/42* (2013.01); *C07D 207/09* (2013.01); *C07D 207/50* (2013.01); *C07D 209/08* (2013.01);
(Continued)

(58) Field of Classification Search
USPC ........................................... 514/63
See application file for complete search history.

(56) References Cited

U.S. PATENT DOCUMENTS 3,987,102 A  10/1976 Karrer
3,987,108 A  10/1976 Karrer
(Continued)

FOREIGN PATENT DOCUMENTS

EP  0 921 120      6/1999
JP  S50-18628 A   2/1975
(Continued)

OTHER PUBLICATIONS

International Search Report issued with respect to application No. PCT/JP2014/072041, dated Nov. 11, 2014.
(Continued)

*Primary Examiner* — Marcos L Sznaidman
(74) *Attorney, Agent, or Firm* — Greenblum & Bernstein, P.L.C.

(57) ABSTRACT

To provide a compound highly active against pests, a pesticide using the compound, and a method for controlling pests by applying the compound.
A phenoxyalkylbenzamide compound represented by the formula (I) or its salt; a pesticide containing it as an active ingredient, and a controlling method, which comprises applying an effective amount of the compound:

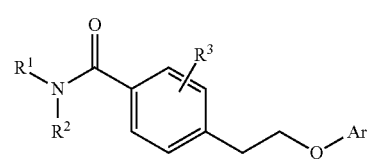

wherein $R^1$, Y and $R^3$ are a hydrogen atom or the like, and Ar is as follows:

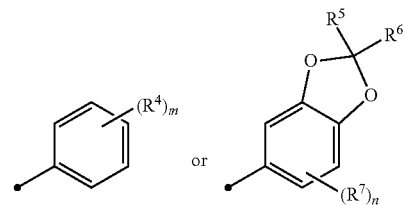

wherein $R^4$ and $R^7$ are halogen or the like, $R^5$ and $R^6$ are a hydrogen atom or the like, m is from 0 to 5, and n is from 0 to 3.

11 Claims, No Drawings

(51) Int. Cl.

| | | |
|---|---|---|
| A01N 37/34 | (2006.01) | |
| A01N 37/38 | (2006.01) | |
| A01N 43/08 | (2006.01) | |
| A01N 43/10 | (2006.01) | |
| A01N 43/16 | (2006.01) | |
| A01N 43/18 | (2006.01) | |
| A01N 43/20 | (2006.01) | |
| A01N 43/30 | (2006.01) | |
| A01N 43/36 | (2006.01) | |
| A01N 43/38 | (2006.01) | |
| A01N 43/40 | (2006.01) | |
| A01N 43/90 | (2006.01) | |
| A01N 47/20 | (2006.01) | |
| C07C 255/54 | (2006.01) | |
| C07C 271/28 | (2006.01) | |
| C07C 317/22 | (2006.01) | |
| C07C 323/42 | (2006.01) | |
| C07C 235/42 | (2006.01) | |
| C07C 235/84 | (2006.01) | |
| C07C 235/88 | (2006.01) | |
| C07C 237/30 | (2006.01) | |
| C07C 255/29 | (2006.01) | |
| C07D 213/75 | (2006.01) | |
| C07D 309/04 | (2006.01) | |
| C07D 317/46 | (2006.01) | |
| C07D 317/64 | (2006.01) | |
| C07D 231/40 | (2006.01) | |
| C07D 333/28 | (2006.01) | |
| C07D 333/36 | (2006.01) | |
| C07D 335/02 | (2006.01) | |
| C07C 323/18 | (2006.01) | |
| C07D 453/02 | (2006.01) | |
| C07D 207/09 | (2006.01) | |
| C07C 243/38 | (2006.01) | |
| C07D 207/50 | (2006.01) | |
| C07D 209/08 | (2006.01) | |
| C07D 211/26 | (2006.01) | |
| C07D 211/98 | (2006.01) | |
| C07D 213/30 | (2006.01) | |
| C07D 213/61 | (2006.01) | |
| C07D 305/08 | (2006.01) | |
| C07D 307/14 | (2006.01) | |
| A01N 55/00 | (2006.01) | |
| C07C 231/14 | (2006.01) | |
| C07C 235/46 | (2006.01) | |

(52) U.S. Cl.
CPC .......... *C07D 211/26* (2013.01); *C07D 211/98* (2013.01); *C07D 213/30* (2013.01); *C07D 213/61* (2013.01); *C07D 213/75* (2013.01); *C07D 231/40* (2013.01); *C07D 305/08* (2013.01); *C07D 307/14* (2013.01); *C07D 309/04* (2013.01); *C07D 317/46* (2013.01); *C07D 317/64* (2013.01); *C07D 333/28* (2013.01); *C07D 333/36* (2013.01); *C07D 335/02* (2013.01); *C07D 453/02* (2013.01); *C07F 7/081* (2013.01); *C07F 7/083* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2602/08* (2017.05); *C07C 2603/74* (2017.05)

(56) References Cited

U.S. PATENT DOCUMENTS

| | | | |
|---|---|---|---|
| 4,094,989 A | 6/1978 | Karrer | |
| 4,153,731 A | 5/1979 | Karrer | |
| 2004/0229949 A1 | 11/2004 | Andersson et al. | |
| 2010/0305124 A1 | 12/2010 | Fusslein et al. | |
| 2011/0136796 A1* | 6/2011 | Mautino | ............ C07D 233/56 514/227.8 |
| 2013/0310379 A1 | 11/2013 | Albrecht et al. | |

FOREIGN PATENT DOCUMENTS

| | | |
|---|---|---|
| JP | 2011-518841 A | 6/2011 |
| JP | 2013-60420 A | 4/2013 |
| WO | 2005/090286 A1 | 9/2005 |
| WO | 2007/008963 A1 | 1/2007 |
| WO | 2007/144639 A1 | 12/2007 |
| WO | 2009-132238 A2 | 10/2009 |
| WO | 2012/068589 A2 | 5/2012 |
| WO | 2013/003505 A1 | 1/2013 |
| WO | 2013/027660 A1 | 2/2013 |

OTHER PUBLICATIONS

International Preliminary Report on Patentability issued with respect to application No. PCT/JP2014/072041, dated Feb. 23, 2016.
Extended European Search Report issued in Patent Application No. 14838546.1, dated Feb. 7, 2017.
Japanese Office Action from Application No. 2015-532920 dated Apr. 2, 2018 with English language translation.
CAS Registry No. 1422925-35-6, Mar. 11, 2013.
CAS Registry No. 1422721-22-9, Mar. 8, 2013.
CAS Registry No. 1422627-89-1, Mar. 8, 2013.
CAS Registry No. 1413524-77-2, 2012.
CAS Registry No. 1394541-51-5, 2012.

* cited by examiner

PESTICIDE

TECHNICAL FIELD

The present invention relates to a pesticide comprising, as an active ingredient, a novel phenoxyalkylbenzamide compound or its salt.

BACKGROUND ART

Patent Document 1 discloses N-(aminoalkyl)arylamide compounds and N-(aminoalkyl)arylsulfonamide compounds useful as pharmaceutical chemicals, and Patent Document 2 discloses 2-oxybenzamide derivatives useful as pharmaceutical chemicals, however, they are distinguished from the compounds of the present invention. Further, Patent Document 3 discloses amido-pyridyl ether compounds useful as parasiticides, however, the compounds have a pyridyl moiety and are different from the compounds of the present invention. Patent Document 4 discloses a wide range of compounds having an EXZH2 inhibitory effect, however, it failed to specifically disclose the compounds of the present invention. Patent Document 5 discloses a group of compounds having an opioid receptor-inhibitory effect, however, it failed to specifically disclose the compounds of the present invention.

PRIOR ART DOCUMENTS

Patent Documents

Patent Document 1: WO2007/008963
Patent Document 2: WO2007/144639
Patent Document 3: WO2013/003505
Patent Document 4: WO2012/068589
Patent Document 5: WO2005/090286

DISCLOSURE OF INVENTION

Technical Problem

Many pesticides have been used over a period of time, however, quite a few of them have various problems such that their effects are insufficient, and that pests have acquired resistance and their use is restricted. Accordingly, development of a novel pesticide with few such defects has been desired. The object of the present invention is to provide a compound highly active against pests, to provide a pesticide using the compound, and a method for controlling pests by applying the compound.

Solution to Problem

The present inventors have conducted extensive studies to overcome the above problems and as a result, found that novel compounds represented by the formula (I) having a phenoxyalkylbenzamide structure or their salts have a very high controlling effect against pests at a low dose, and accomplished the present invention.

That is, the present invention provides a phenoxyalkylbenzamide compound represented by the formula (I) or its salt (hereinafter sometimes referred to as Invention Compound):

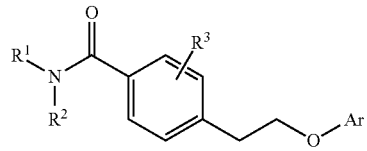

(I)

wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl, alkylcarbonylalkyl, Y or alkyl substituted by Y;

Y is a saturated or unsaturated cyclic group which may be substituted by Z, and the cyclic group may contain one or two hetero atoms selected from a nitrogen atom which may be substituted by alkyl, an oxygen atom and a sulfur atom;

Z is halogen, alkyl, haloalkyl, alkoxy, haloalkoxy, cyano, amino, alkoxycarbonylamino or nitro;

$R^2$ is a hydrogen atom, alkyl, alkylcarbonyl or alkylcarbonylalkyl; or $R^1$ and $R^2$ may form, together with the adjacent nitrogen atom, a cyclic structure which may be substituted by Z, and the cyclic structure may further contain one hetero atom selected from a nitrogen atom which may be substituted by alkyl, an oxygen atom and a sulfur atom;

$R^3$ is a hydrogen atom, halogen, alkyl, haloalkyl, alkylcarbonyl, alkoxycarbonyl, alkoxy, amino, monoalkylamino, dialkylamino, cyano or nitro;

Ar is

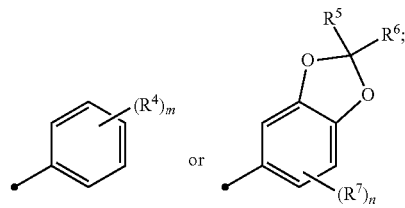

each of $R^4$ and $R^7$ which are independent of each other, is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano, nitro, phenoxy which may be substituted by $R^9$, phenyl which may substituted by $R^9$, or a heterocyclic group which may be substituted by $R^9$;

each of $R^5$ and $R^6$ which are independent of each other, is a hydrogen atom, halogen, alkyl or haloalkyl;

$R^8$ is hydrogen, alkyl, halogen, alkoxy, alkylcarbonyl, alkoxycarbonyl, amino, monoalkylamino, dialkylamino, trialkylsilyl or Y;

$R^9$ is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano or nitro;

m is an integer of from 0 to 5; and n is an integer of from 0 to 3, a pesticide containing the Invention Compound as an active ingredient, an insecticide containing the Invention Compound as an active ingredient, and a method for controlling pests, which comprises applying an effective amount of the Invention Compound.

Advantageous Effects of Invention

The Invention Compound has a high controlling effect against pests even at low dose.

DESCRIPTION OF EMBODIMENTS

In this specification, unless otherwise specified, the halogen or the halogen as a substituent may, for example, be fluorine, chlorine, bromine or iodine. The number of halogens as the substitutes may be one or more, and if more, the respective halogens may be the same or different. Further, the positions for substitution with such halogens may be any positions.

In this specification, unless otherwise specified, the alkyl or the alkyl moiety may be either linear or branched, and it may, for example, be specifically a $C_{1-6}$ alkyl such as methyl, ethyl, n-propyl, isopropyl, n-butyl, isobutyl, sec-butyl, tert-butyl, n-pentyl, neopentyl or n-hexyl.

In this specification, unless otherwise specified, the alkenyl or the alkenyl moiety may be either linear or branched, and it may, for example, be specifically $C_{2-6}$ alkenyl such as vinyl, 1-propenyl, 2-propenyl, 2-methyl-2-propenyl, isopropenyl, 1-butenyl, 1,3-butadienyl or 1-hexenyl.

In this specification, unless otherwise specified, the alkynyl or the alkynyl moiety may be either linear or branched, and it may, for example, be specifically a $C_{2-6}$ alkynyl such as ethynyl, 1-propynyl, 2-propynyl, 1-butynyl, 2-methyl-3-butynyl or 1-hexynyl.

In this specification, unless otherwise specified, the number of the alkoxy groups displacing the alkyl in the alkoxyalkyl may be one or more, and if more, the respective alkoxy may be the same or different. Further, the positions for substitution with such alkoxy may be any positions of the alkyl.

In this specification, unless otherwise specified, the cyclic group as a substituent may be either saturated or unsaturated, and it may, for example, be specifically a cycloalkyl such as cyclopropyl, cyclobutyl, cyclopentyl, cyclohexyl, cycloheptyl or adamantly; an aryl such as phenyl, naphthyl or indanyl; a 5-membered monocyclic heterocyclic ring such as tetrahydrofuranyl, pyrrolidinyl, pyrazolyl, imidazolyl, thienyl, furyl, pyrrolyl, oxazolyl, isoxazolyl, thiazolyl, isothiazolyl, 1,3,4-oxadiazolyl, 1,2,4-oxadiazolyl, 1,3,4-thiadiazolyl, 1,2,4-thiadiazolyl, 1,2,3-thiadiazolyl, 1,2,4-triazolyl, 1,2,3-triazolyl or 1,2,3,4-tetrazolyl; a 6-membered monocyclic heterocyclic ring such as pyridyl, pyrimidyl, pyrazinyl, pyridazinyl, 1,3,5-triazinyl, 1,2,4-triazinyl, 4-tetrahydropyranyl, 4-tetrahydrothiopyranyl, 4-piperidinyl or 1-methy-4-piperidinyl; or a bridged polycyclic heterocyclic ring such as quinuclidinyl. Among such cyclic groups, a saturated or unsaturated 3- to 7-membered ring is preferred. Further, the heterocyclic ring moiety in "the heterocyclic ring which may be substituted by $R^9$" defined for Het may, for example, be the above 5-membered monocyclic heterocyclic ring, 6-membered monocyclic heterocyclic ring or bridged polycyclic heterocyclic ring. The 5-membered monocyclic heterocyclic ring is preferably thienyl such as 2-thienyl or 3-thienyl; furyl such as 2-furyl or 3-furyl; pyrrolyl such as 2-pyrrolyl or 3-pyrrolyl; oxazolyl such as 2-oxazolyl, 4-oxazolyl or 5-oxazolyl; isoxazolyl such as 3-isoxazolyl, 4-isoxazolyl or 5-isoxazolyl; thiazolyl such as 2-thiazolyl, 4-thiazolyl or 5-thiazolyl; isothiazolyl such as 3-isothiazolyl, 4-isothiazolyl or 5-isothiazolyl; pyrazolyl such as 3-pyrazolyl, 4-pyrazolyl or 5-pyrazolyl; imidazolyl such as 2-imidazolyl, 4-imidazolyl or 5-imidazolyl; 1,3,4-oxadiazolyl such as 2-(1,3,4-oxadiazolyl); 1,2,4-oxadiazolyl such as 3-(1,2,4-oxadiazolyl) or 5-(1,2,4-oxadiazolyl); 1,3,4-thiadiazolyl such as 2-(1,3,4-thiadiazolyl); 1,2,4-thiadiazolyl such as 3-(1,2,4-thiadiazolyl) or 5-(1,2,4-thiadiazolyl); 1,2,3-thiadiazolyl such as 4-(1,2,3-thiadiazolyl) or 5-(1,2,3-thiadiazolyl); 1,2,4-triazolyl such as 3-(1,2,4-triazolyl) or 5-(1,2,4-triazolyl); 1,2,3-triazolyl such as 4-(1,2,3-triazolyl) or 5-(1,2,3-triazolyl); 1,2,3,4-tetrazolyl such as 5-(1,2,3,4-tetrazolyl); or the like. Further, the 6-membered monocyclic heterocyclic ring is preferably pyridyl such as 2-pyridyl, 3-pyridyl or 4-pyridyl; pyrimidyl such as 2-pyrimidyl, 4-pyrimidyl or 5-pyrimidyl; pyrazinyl such as 2-pyrazinyl or 3-pyrazinyl; pyridazinyl such as 3-pyridazinyl or 4-pyridazinyl; 1,3,5-triazinyl such as 2-(1,3,5-triazinyl); 1,2,4-triazinyl such as 3-(1,2,4-triazinyl), 5-(1,2,4-triazinyl) or 6-(1,2,4-triazinyl); or the like. Among them, preferred is pyridyl or thienyl. Further, the "cyclic structure formed together by $R^1$ and $R^2$" may be a skeleton such as a saturated monocyclic heterocyclic ring such as aziridine, azetidine, pyrrolidine, piperidine, hexamethyleneimine, piperazine, morpholine or thiomorpholine; an unsaturated monocyclic heterocyclic ring such as pyrrole, pyrazole or imidazole; or a bridged polycyclic heterocyclic ring such as indole.

In this specification, m and n represents the numbers of substituents $R^4$ and $R^7$, respectively. When the number of such substituents is 2 or more, the 2 or more substituents may be the same or different.

The salt of the compound of the formula (I) includes all kinds so long as they are acceptable in this technical field. It may, for example, be a salt with an inorganic acid such as hydrochloric acid, hydrobromic acid, sulfuric acid or phosphoric acid; a salt with an organic carboxylic acid such as tartaric acid, formic acid, acetic acid, citric acid, fumaric acid, maleic acid, trichloroacetic acid or trifluoroacetic acid; or a salt with sulfonic acid such as methanesulfonic acid, benzenesulfonic acid, p-toluenesulfonic acid, mesitylenesulfonic acid or naphthalenesulfonic acid.

The Invention Compound may have isomers such as geometrical isomers, tautomers or optical isomers, and each or both of such isomers and mixtures thereof are included in the present invention. In this specification, unless otherwise specified, isomers are in the form of a mixture. Further, in the present invention, various isomers other than those mentioned above, may be included within the scope of the common knowledge in this technical field.

Further, depending upon the type of the isomer, it may have a chemical structure different from the above formula, but for those skilled in the art, it can sufficiently be recognized that it is in an isomeric relationship and falls within the scope of the present invention.

The Invention Compound can be produced in accordance with the following processes and a usual process for producing a salt, however, the present invention is by no means limited to such processes.

Process [1]

The Invention Compound may be produced by the following process [1]:

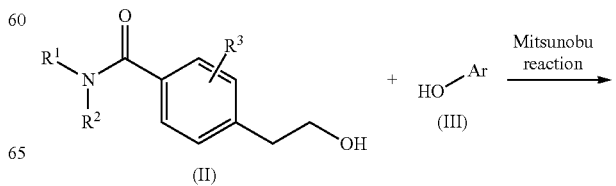

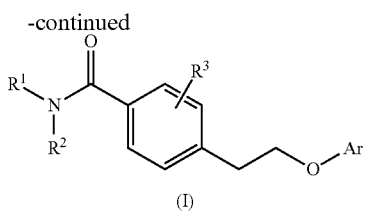

In the process [1], $R^1$, $R^2$, $R^3$ and Ar are as defined above.

This reaction is a reaction of coupling the compound of the formula (II) and the compound of the formula (III) in the presence of an azo reagent and a phosphine reagent by Mitsunobu reaction to obtain the compound of the formula (I). The compound of the formula (II) may be prepared by the after-mentioned process. Further, the compound of the formula (III) may be a commercially available product or may be prepared in accordance with a known method as disclosed in the after-mentioned Preparation Example 3(2).

The azo reagent used in this reaction may, for example, be diethyl azodicarboxylate (DEAD), diisopropyl azodicarboxylate (DIAD), di-tert-butyl azodicarboxylate (DBAD), 1,1'-(azodicarbonyl)dipiperidine (ADDP), 1,1'-azobis(N,N-diisopropylformamide) (TIPA) or 1,6-dimethyl-1,5,7-hexahydro-1,4,6-tetrazocine-2,5-dione (DHAD).

The phosphine reagent used in this reaction may, for example, be a trialkylphosphine such as trimethylphosphine, triethylphosphine, tripropylphosphine, triisopropylphosphine, tributylphosphine, triisobutylphosphine or tricyclohexylphosphine; or a triarylphosphine such as triphenylphosphine, diphenyl(2-pyridyl)phosphine or (4-dimethylaminophenyl)diphenylphosphine.

This reaction may be carried out usually in the presence of a solvent. The solvent is not particularly limited so long as the reaction proceeds, and for example, one or more may be properly selected and mixed from a halogenated hydrocarbon such as methylene chloride, chloroform, dichloroethane, trichloroethane or carbon tetrachloride; an aromatic hydrocarbon such as benzene, toluene, xylene or chlorobenzene; a hydrocarbon such as n-hexane or n-heptane; an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethane; and the like.

The reaction temperature is usually from 0° C. to 150° C. The reaction time is usually from 1 minute to 48 hours.

Process [2]

The Invention Compound may be produced by the following process [2]:

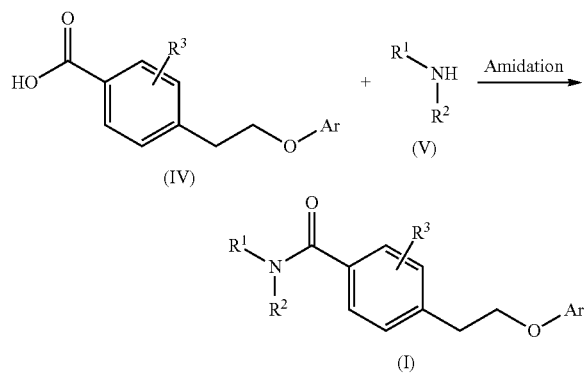

In the process [2], $R^1$, $R^2$, $R^3$ and Ar are as defined above.

The compound of the formula (I) may be prepared by reacting the compound of the formula (IV) which can be prepared by the after-mentioned process and the compound of the formula (V) which may be commercially available or may be prepared in accordance with a known process, in the presence of a condensing agent and a base.

The condensing agent used in this reaction may, for example, be N,N'-dicyclohexylcarbodiimide (DCC), 1-ethyl-3-(3-dimethylaminopropyl)carbodiimide hydrochloride (EDC-HCl), O-(benzotriazol-1-yl)-N,N,N',N'-tetramethyluronium hexafluorophosphate (HBTU) or 4-(4,6-dimethoxy-1,3,5-triazin-2-yl)-4-methylmorpholinium chloride (DMT-MM).

The base used in this reaction is not particularly limited so long as the reaction proceeds, and for example, one or more may be properly selected and mixed from a tertiary amine such as triethylamine, 4-methylmorpholin or diisopropylethylamine; 1,8-diazabicyclo[5.4.0]-7-undecene (DBU); pyridine; 4-(dimethylamino)pyridine (DMAP); 2,6-lutidine; and the like.

This reaction may be carried out usually in the presence of a solvent. The solvent is not particularly limited so long as the reaction proceeds, and it may be any solvent inert to the reaction. For example, one or more may be properly selected and mixed from a halogenated hydrocarbon such as methylene chloride, chloroform, dichloroethane, trichloroethane or carbon tetrachloride; a hydrocarbon such as n-hexane or n-heptane; an ester such as methyl acetate, ethyl acetate or propyl acetate; an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethane; and the like.

This reaction may be carried out in the presence of a catalyst as the case requires, and the catalyst may be properly selected from 4-(dimethylamino)pyridine, 4-hydroxybenzotriazole and the like.

The reaction temperature is usually from 0° C. to 150° C. The reaction time is usually from 1 minute to 72 hours.

Further, this reaction may also be carried out after the compound of the formula (IV) is converted into its active derivative such as an acid chloride or an acid anhydride, in the presence of a base and a solvent.

To convert the compound of the formula (IV) into an acid chloride, thionyl chloride, oxalyl chloride or the like may be used, and to convert it into an acid anhydride, acetyl chloride, trifluoroacetyl chloride or the like may be used. As a reagent to convert it into another active derivative, ethyl chlorocarbonate, methanesulfonyl chloride, trifluoromethanesulfonyl chloride, p-toluenesulfonyl chloride or the like may be used.

This reaction may be carried out usually in the presence of a solvent. The solvent may, for example, be the same solvent as in the process [I].

The reaction temperature is usually from −20° C. to 80° C. The reaction time is usually from 1 minute to 48 hours.

The compound of the formula (I) may be produced by reacting the compound of the formula (V) and a reaction solution containing the obtained active derivative usually in the presence of a base and a solvent.

The base used in this reaction is not particularly limited so long as the reaction proceeds, and for example, one or more may be properly selected and mixed from a tertiary amine such as triethylamine or diisopropylethylamine; an alkali metal carbonate such as sodium carbonate, potassium carbonate or cesium carbonate; an alkali metal hydride such as sodium hydride or potassium hydride; an alkali metal alkoxide such as sodium methoxide, sodium ethoxide or potassium tert-butoxide; 1,8-diazabicyclo[5.4.0]-7-undecene (DBU), pyridine, 4-(dimethylamino)pyridine (DMAP), 2,6-lutidine; and the like.

This reaction may be carried out usually in the presence of a solvent. The solvent may, for example, be the same solvent as in the process [I].

The reaction temperature is usually from −20° C. to 80° C. The reaction time is usually from 1 minute to 48 hours.

Process for Intermediate [1]

The compound of the formula (II) as a starting material in the process [1] may be prepared, for example, by reactions of the following steps (1) to (7).

reaction. For example, one or more may be properly selected and mixed from a halogenated hydrocarbon such as methylene chloride, chloroform, dichloroethane, trichloroethane or carbon tetrachloride; an aromatic hydrocarbon such as benzene, toluene, xylene or chlorobenzene; a hydrocarbon such as n-hexane or n-heptane; an ether such as diethyl ether, tert-butyl methyl ether, 1,4-dioxane, tetrahydrofuran (THF) or 1,2-dimethoxyethane; an alcohol such as methanol, ethanol or isopropyl alcohol; and the like.

This reaction may be carried out in the presence of a catalyst as the case requires. The catalyst may, for example, be iodine, a trifluoroborane-diethyl ether complex or zinc borohydride.

The reaction temperature is usually from −80° C. to 150° C. The reaction time is usually from 1 minute to 48 hours.

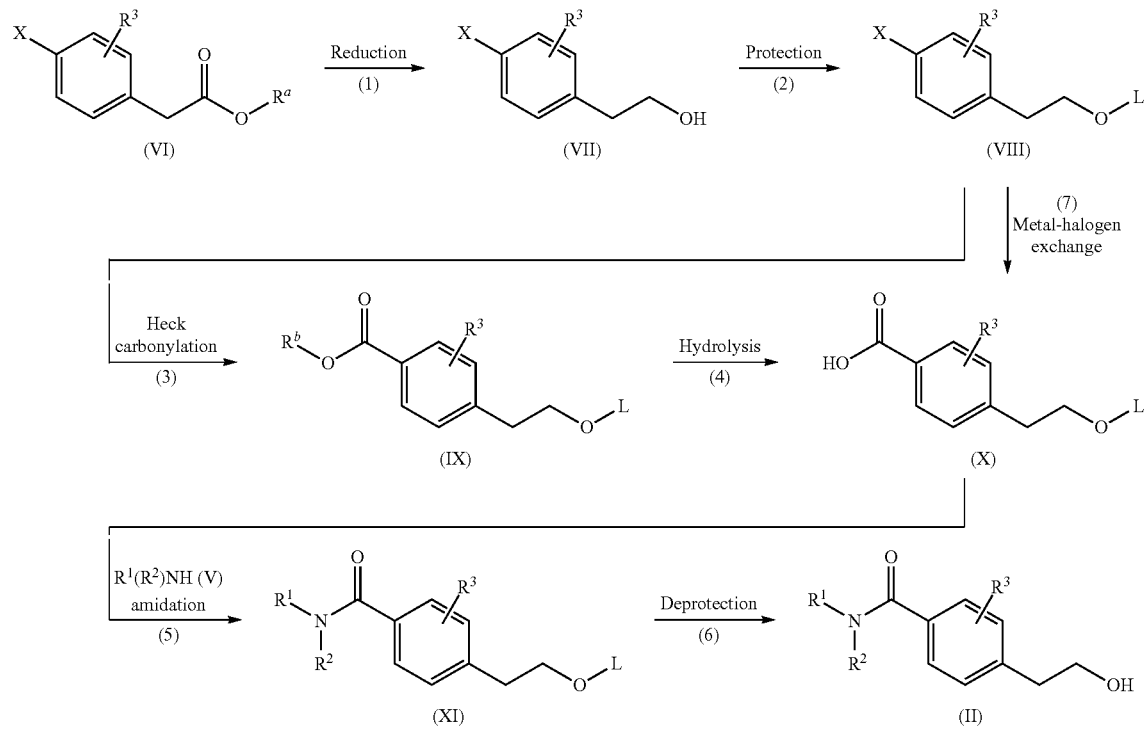

In the above reaction formulae, $R^1$, $R^2$ and $R^3$ are as defined above. X is a chlorine atom, a bromine atom or an iodine atom, each of $R^a$ and $R^b$ which are independent of each other, is a hydrogen atom or $C_{1-6}$ alkyl, and L is a silyl protecting group.

Step (1)

This reaction is a reaction of reducing the compound of the formula (VI) to obtain the compound of the formula (VII). This reaction may be carried out in the presence of a reducing agent. The compound of the formula (VI) may be a commercially available product or may be prepared in accordance with a known process.

The reducing agent used in this reaction may, for example, be lithium aluminum hydride, diisobutylaluminum hydride, sodium bis(2-methoxyethoxy)aluminum dihydride, sodium borohydride, lithium borohydride or a borane-THF complex.

This reaction is carried out usually in the presence of a solvent. The solvent is not particularly limited so long as the reaction proceeds, and may be any solvent inert to the reaction. For example, one or more may be properly selected This reaction may be carried out in the presence of an inert gas as the case requires, and the inert gas may, for example, be an argon gas or a nitrogen gas.

Step (2)

This reaction is a reaction of protecting the hydroxy group of the compound (VII) to obtain the compound of the formula (VIII). This reaction may be carried out in the presence of a protecting reagent and a base.

The protecting reagent used in this reaction may, for example, be trimethylsilyl chloride (TMSCl), triethylsilyl chloride (TESCl), tert-butyldimethylsilyl chloride (TBSCl), dimethylthexylsilyl chloride (TDSCl), triisopropylsilyl chloride (TIPSCl) or tert-butyldiphenylsilyl chloride (TBDPSCl).

The base used in this reaction may, for example, be the same base as in the process [2].

This reaction is carried out usually in the presence of a solvent. The solvent may, for example, be the same solvent as in the process [1].

The reaction temperature is usually from 0° C. to 150° C. The reaction time is usually from 1 minute to 48 hours.

The protecting group for the hydroxy group and the protecting method are in accordance with known literature or books (for example, Protective Groups in Organic Synthesis Forth Edition, John Wiley & Sons, Inc.).

Step (3)

This reaction is a reaction of subjecting the compound of the formula (VIII) to Heck carbonylation to obtain the compound of the formula (IX). This reaction may be carried out in the presence of a palladium catalyst, carbon monoxide, a base and an alcohol.

The palladium catalyst used in this reaction may be any catalyst commonly used in the Heck carbonylation reaction, and may, for example, be tris(dibenzylideneacetone)dipalladium(0) ($Pd_2(dba)_3$), tetrakis(triphenylphosphine)palladium(0) ($Pd(PPh_3)_4$), [1,1'-bis(diphenylphosphino)ferrocene]dichloropalladium(II) ($Pd(dppf)Cl_2$) or palladium(II) acetate ($Pd(OAc)_2$). The reaction may be carried out in the presence of a ligand as the case requires, and the ligand may, for example, 1,2-bis(diphenylphosphino)ethane (dppe), 1,3-bis(diphenylphosphino)propane (dppp), 1,4-bis(diphenylphosphino)butane (dppb) or 1,1'-bis(diphenylphosphino)ferrocene (dppf).

The base used in this reaction is not particularly limited so long as the reaction proceeds, and for example, one or more may be properly selected and mixed from a tertiary amine such as triethylamine or diisopropylethylamine; an alkali metal carbonate such as sodium carbonate, potassium carbonate or cesium carbonate; an alkaline earth metal carbonate such as calcium carbonate or barium carbonate; an alkali metal hydroxide such as lithium hydroxide, sodium hydroxide or potassium hydroxide; an alkaline earth metal hydroxide such as calcium hydroxide or barium hydroxide; and the like.

The alcohol used in this reaction may, for example, be methanol, ethanol or tert-butyl alcohol.

This reaction may be carried out usually in the presence of a solvent. The solvent is not particularly limited so long as the reaction proceeds, and may be any solvent inert to the reaction. For example, one or more may be properly selected and mixed from an aromatic hydrocarbon such as benzene, toluene, xylene or chlorobenzene, a hydrocarbon such as n-hexane or n-heptane; an alcohol such as methanol, ethanol or isopropyl alcohol; an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethene; water; and the like.

The reaction temperature is usually from 0° C. to 150° C. The reaction time is usually from 1 minute to 48 hours.

The pressure in the reactor may be optional pressure within a range of from 1 to 50 atm.

Step (4)

This reaction is a reaction of hydrolyzing the compound of the formula (IX) in a case where $R^6$ is $C_{1-6}$ alkyl, to obtain the compound of the formula (X). This reaction may be carried out in accordance with a process possible in a conventional synthetic organic chemistry.

This reaction may be carried out usually by using a base and a solvent.

The base is not particularly limited so long as the reaction proceeds, and for example, one or more may be properly selected and mixed from an alkali metal hydroxide such as lithium hydroxide, sodium hydroxide or potassium hydroxide; an alkaline earth metal hydroxide such as calcium hydroxide or barium hydroxide; an alkali metal carbonate such as sodium carbonate, potassium carbonate or cesium carbonate; an alkaline earth metal carbonate such as calcium carbonate or barium carbonate; and the like.

The solvent is not particularly limited so long as the reaction proceeds, and may be any solvent inert to the reaction. For example, one or more may be properly selected and mixed from an alcohol such as methanol, ethanol or isopropyl alcohol; an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethane; water; and the like.

The reaction temperature is usually from 0° C. to 100° C. The reaction time is usually from 1 minute to 72 hours.

Step (5)

This reaction is a reaction of amidating the compound of the formula (X) and the compound of the formula (V) to obtain the compound of the formula (XI). This reaction may be carried out in the same manner as the process [2].

Step (6)

This reaction is a reaction of deprotecting the compound of the formula (XI) to obtain the compound of the formula (II). This reaction may be carried out in the presence of an acid.

The acid used in this reaction may, for example, be an inorganic acid such as hydrochloric acid or an organic acid such as acetic acid, formic acid or trifluoroacetic acid.

This reaction may be carried out usually in the presence of a solvent. The solvent is not particularly limited so long as the reaction proceeds and may be any solvent inert to the reaction. For example, one or more may be properly selected and mixed from an ether such as diethyl ether, tert-butyl methyl ether, 1,4-dioxane, tetrahydrofuran (THF) or 1,2-dimethoxyethane; an alcohol such as methanol, ethanol or isopropyl alcohol; water; and the like.

Proper deprotection of the protective group may be carried out in accordance with known literature or books (for example, Protective Groups in Organic Synthesis Forth Edition, John Wiley & Sons, Inc.).

Step (7)

This reaction is another process to obtain the formula (X), and by subjecting the compound of the formula (VIII) to metal-halogen exchange, the compound of the formula (X) may be obtained. This reaction may be carried out in the presence of a lithiation reagent and carbon dioxide.

The lithiation reagent used in this reaction may, for example, be an alkyllithium such as n-butyllithium or tert-butyllithium; or a lithium amide such as lithium diisopropylamide (LDA).

This reaction may be carried out usually in the presence of a solvent. The solvent is not particularly limited so long as the reaction proceeds, and may be any solvent inert to the reaction. For example, one or more may be properly selected and mixed from a hydrocarbon such as n-hexane or n-heptane; an ether such as diethyl ether, tert-butyl methyl ether, 1,4-dioxane, tetrahydrofuran (THF) or 1,2-dimethoxyethane; dimethylpropyleneurea (DMPU); hexamethylphosphoramide (HMPA); and the like.

The reaction temperature is usually from −80° C. to 0° C. The reaction time is usually from 1 minute to 24 hours.

This reaction may be carried out in the presence of an inert gas as the case requires, and the inert gas may, for example, be an argon gas or a nitrogen gas.

Further, the compound of the formula (II) as a starting material in the process [1] may be prepared, for example, by reactions of the following steps (8) to (10):

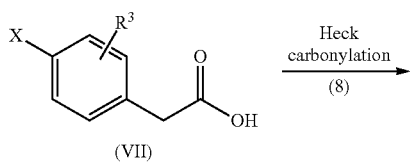

(VII)

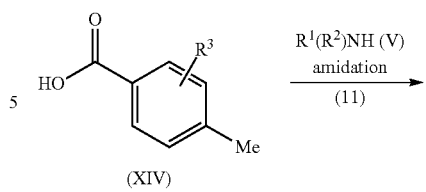

(XIV)

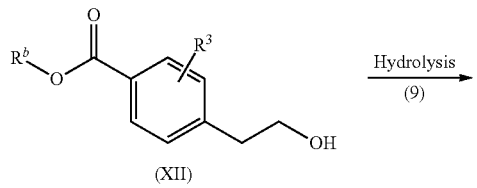

(XII)

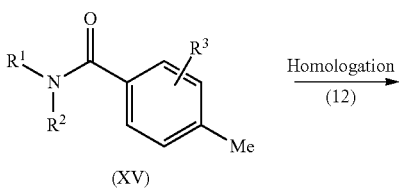

(XV)

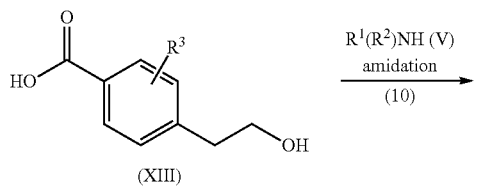

(XIII)

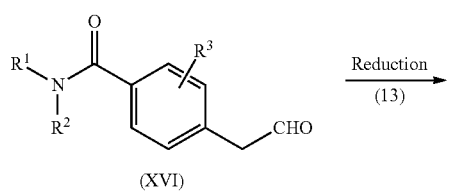

(XVI)

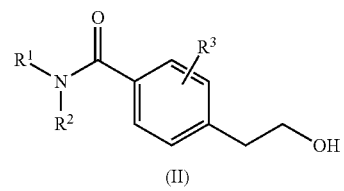

(II)

In the above reaction formulae, $R^1$, $R^2$, $R^3$, $R^b$ and X are as defined above.

Step (8)

This reaction is a reaction of subjecting the compound of the formula (VII) to Heck carbonylation to obtain the compound of the formula (XII). This reaction may be carried out in the same manner as the step (3) in the process for intermediate [1]. The compound of the formula (VII) may be a commercially available compound or may be prepared by the method of the above step (1).

Step (9)

This reaction is a reaction of hydrolyzing the compound of the formula (XII) in a case where $R^b$ is $C_{1-6}$ alkyl to obtain the compound of the formula (XIII). This reaction may be carried out in the same manner as the step (4) in the process for intermediate [1].

Step (10)

This reaction is a reaction of amidating the compound of the formula (XIII) and the compound of the formula (V) to obtain the compound of the formula (II). This reaction may be carried out in the same manner as the process [2].

Further, the compound of the formula (II) as a starting material in the process [1] may also be prepared, for example, by reactions of the following steps (11) to (13):

In the above reaction formulae, $R^1$, $R^2$ and $R^3$ are as defined above.

Step (11)

This reaction is a reaction of amidating the compound of the formula (XIV) and the compound of the formula (V) to obtain the compound of the formula (XV). This reaction may be carried out in the same manner as the process [2]. The compound of the formula (XIV) may be a commercially available product or may be prepared in accordance with a known process.

Step (12)

This reaction is a reaction of reacting the compound of the formula (XV) with N,N-dimethylformamide dimethylacetal or the like, followed by treatment with an acid such as hydrochloric acid or sulfuric acid to obtain the compound of the formula (XVI). This reaction may be carried out, for example, in accordance with Synthetic Communications, 41, 3078 to 3084 (2011).

Step (13)

This reaction is a reaction of reducing the compound of the formula (XVI) to obtain the compound of the formula (II). This reaction may be carried out in the same manner as the step (1) in the process for intermediate [1].

Process for Intermediate [2]

The compound of the formula (IV) as a starting material in the process [2] may be prepared, for example, by reactions of the following steps (14) to (17):

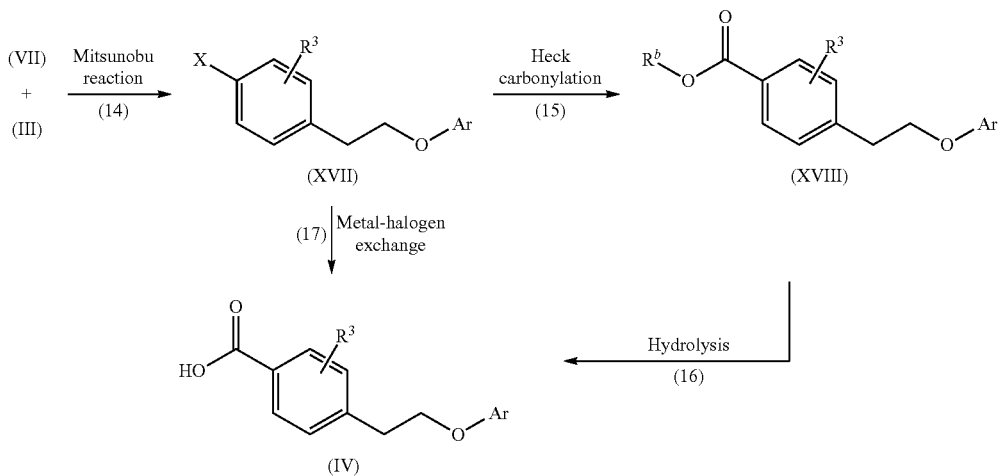

Step (14)

This reaction is a reaction of subjecting the compound of the formula (VII) and the compound of the formula (III) to Mitsunobu reaction to obtain the compound of the formula (XVII). This reaction may be carried out in the same manner as in the process [1].

Step (15)

This reaction is a reaction of subjecting the compound of the formula (XVII) to Heck carbonylation to obtain the compound of the formula (XVIII). This reaction may be carried out in the same manner as the step (3) in the process for intermediate [1].

Step (16)

This reaction is a reaction of hydrolyzing the compound of the formula (XVIII) in a case where $R^b$ is $C_{1-6}$ alkyl to obtain the compound of the formula (IV). This reaction may be carried out in the same manner as the step (4) in the process for intermediate [1].

Step (17)

This reaction is another process to obtain the compound of the formula (IV) by subjecting the compound of the formula (XVII) to metal-halogen exchange to obtain the compound of the formula (IV). This reaction may be carried out in the same manner as the step (7) in the process for intermediate [1].

The compound of the formula (IV) as a starting material in the process [2] may be prepared, for example, by reactions of the following steps (14) to (17).

Further, the compound of the formula (XVIII) as an intermediate in the process for intermediate [2] may be prepared, for example, by a reaction of the following step (18):

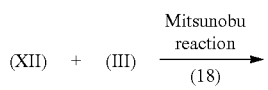

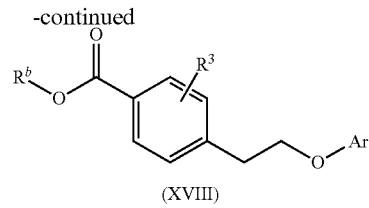

In the above reaction formulae, $R^3$, $R^b$ and Ar are as defined above.

Step (18)

This reaction is a reaction of subjecting the compound of the formula (XII) and the compound of the formula (III) to Mitsunobu reaction to obtain the compound of the formula (XVIII). This reaction may be carried out in the same manner as the process [1].

Among the compounds of the formula (XVIII) as an intermediate in the process for intermediate [2], a compound of the formula (XVIII-3) and a compound of the formula (XVIII-4) may be prepared, for example, by reactions of the following steps (19) and (20), respectively. Further, a compound of the formula (XVIII-1-X) as a material compound in both the steps may be prepared, for example, by the reaction of the above step (15) or (18). Further, the compound of the formula (XIX) and the compound of the formula (XX) may be commercially available products or may be prepared in accordance with a known process.

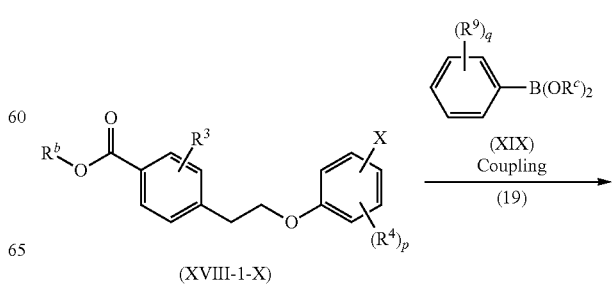

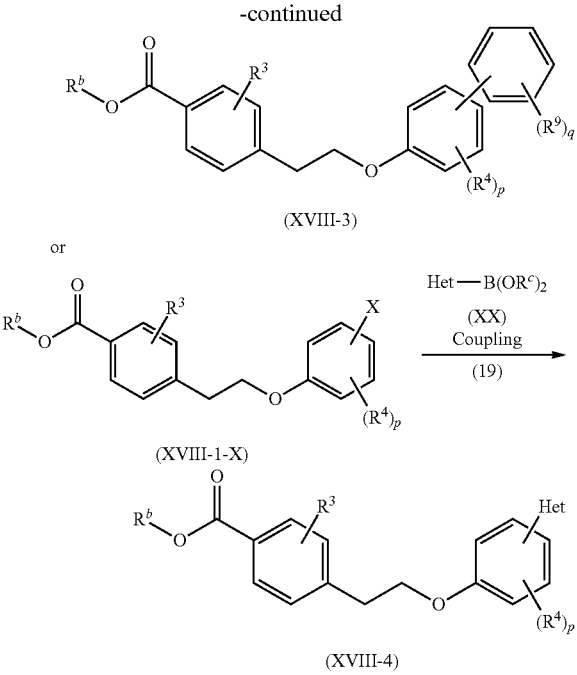

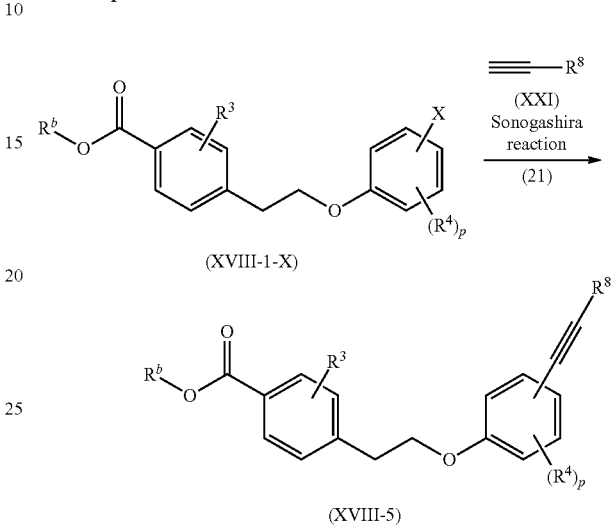

Among the compounds of the formula (XVIII) as an intermediate in the process for intermediate [2], a compound of the formula (XVIII-5) may be prepared, for example, by a reaction of the following step (21). Further, a compound of the formula (XVIII-1-X) as a material compound in this step may be prepared by the reaction of the above step (15) or (18). Further, the compound of the formula (XXI) may be a commercially available product or may be prepared by a known process.

In the above reaction formulae, $R^3$, $R^4$, $R^9$, $R^b$, X and Het are as defined above, p is an integer of from 0 to 4, and q is an integer of from 0 to 5. $R^c$ is hydrogen atoms or $C_{1-6}$ alkyls which may be the same or different, or the two $R^c$'s together may form a —CH$_2$CH$_2$— or —C(CH$_3$)$_2$C(CH$_3$)$_2$—.

The reactions in the steps (19) and (20) are carried out in the presence of a metal catalyst and a base. The metal catalyst used in the reactions may be a catalyst commonly used in a cross coupling reaction, and may, for example, be a palladium catalyst such as palladium-carbon, palladium chloride, palladium acetate, tetrakis(triphenylphosphine)palladium or bis(triphenylphosphine)palladium dichloride, or a copper catalyst such as metal copper, copper(I) acetate, copper(II) acetate, copper(I) oxide, copper(II) oxide or copper iodide.

The base used in the reactions may, for example, be the same base as in the step (3) in the process for intermediate [1].

These reactions may be carried out usually in the presence of a solvent. The solvent is not particularly limited so long as the reaction proceeds, and may be any solvent inert to the reaction. For example, one or more may be properly selected and mixed from a halogenated hydrocarbon such as methylene chloride, chloroform, dichloroethane, trichloroethane or carbon tetrachloride; an aromatic hydrocarbon such as benzene, toluene, xylene or chlorobenzene; a hydrocarbon such as n-hexane or n-heptane; an alcohol such as methanol, ethanol or isopropyl alcohol; an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethene; water; and the like.

The reaction temperature is usually from 0° C. to 150° C. The reaction time is usually from 1 minute to 48 hours.

The reactions may be carried out in the presence of an inert gas as the case requires, and the inert gas may, for example, be an argon gas or a nitrogen gas.

In the above reaction formulae, $R^3$, $R^4$, $R^8$, $R^b$, p and X are as defined above.

This reaction may be carried out in the presence of a palladium catalyst, a copper salt and a base. The palladium catalyst used in the reaction may be a catalyst commonly used in a cross coupling reaction. It may, for example, be tetrakis(triphenylphosphine)palladium or bis(triphenylphosphine)palladium dichloride.

The copper salt may be copper(I) iodide.

The base used in this reaction may, for example, be the same base as in the step (3) in the process for intermediate [1].

This reaction may be carried out usually in the presence of a solvent. The solvent is not particularly limited so long as the reaction proceeds, and may be any solvent inert to the reaction. For example, one or more may be properly selected and mixed from an aprotic polar solvent such as acetonitrile, N,N-dimethylformamide (DMF), dimethylsulfoxide (DMSO), dimethylacetamide (DMA), hexamethylphosphoric triamide (HMPA) or sulfolane; an ether such as diethyl ether, tert-butyl methyl ether, 1,4-dioxane, tetrahydrofuran (THF) or 1,2-dimethoxyethene; a tertiary amine such as triethylamine or diisopropylethylamine; and the like.

The reaction temperature is usually from 0° C. to 150° C. The reaction time is usually from 1 minute to 48 hours.

This reaction may be carried out in the presence of an inert gas as the case requires, and the inert gas may, for example, be an argon gas or a nitrogen gas. Process for intermediate [3]

Among the compounds of the formula (III) as a starting material in the process [1], a compound of the formula (III-3) and a compound of the formula (III-4) may be prepared, for example, by reactions of the following steps (22) and (23), respectively.

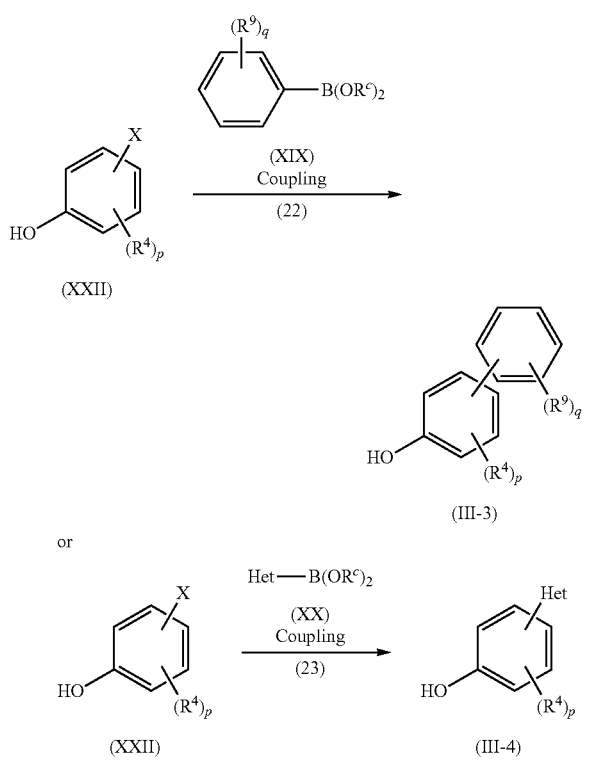

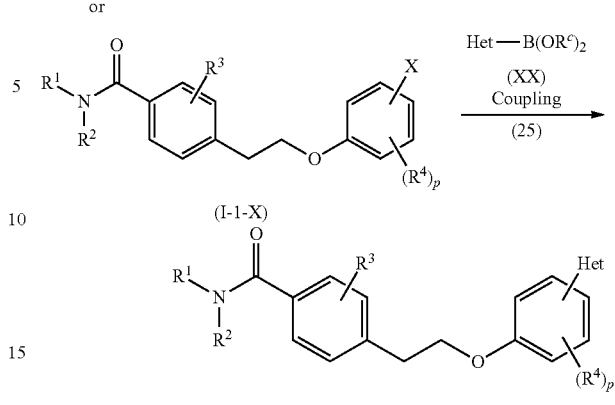

In the process [3], $R^1$, $R^2$, $R^3$, $R^4$, $R^9$, $R^c$, p, q, X and Het are as defined above.

The reactions in the steps (24) and (25) are carried out in the presence of a metal catalyst and a base. The reactions may be carried out in the same manner as the steps (19) and (20) in the process for intermediate [2].

Process [4]

The Invention Compound may be prepared by a reaction of the step (26) in the following process [4]. Further, the compound of the formula (I-1-X) as a material compound in this step may be prepared by the reaction of the above process [1] or [2]. Further, the compound of the formula (XX) may be a commercially available product or may be prepared in accordance with a known process:

In the process for intermediate [3], $R^4$, $R^9$, $R^c$, p, q, X and Het are as defined above.

The reactions of the steps (22) and (23) may be carried out in the presence of a metal catalyst and a base. The reactions may be carried out in the same manner as in the steps (19) and (20) in the process for intermediate [2], respectively.

Process [3]

The Invention Compound may be prepared by reactions of the steps (24) and (25) in the following process [3]. Further, the compound of the formula (I-1-X) as a material compound in this step may be prepared by the reaction in the above process [1] or [2]. Further, the compound of the formula (XIX) and the compound of the formula (XX) may be commercially available products or may be prepared in accordance with a known process:

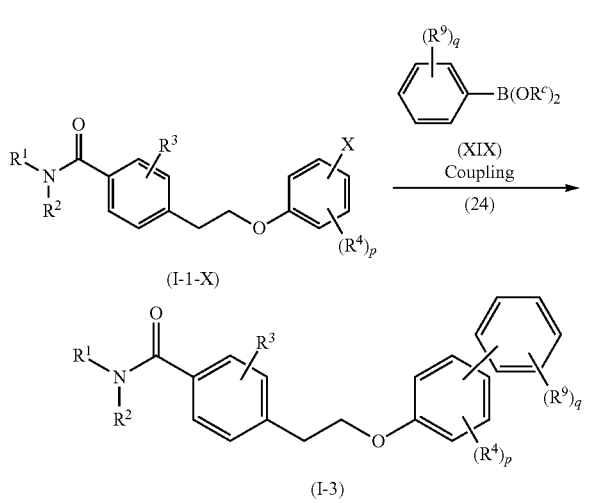

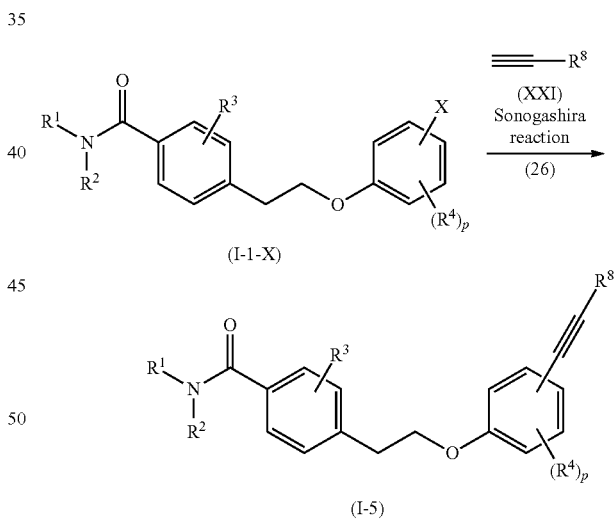

In the above reaction formula, $R^1$, $R^2$, $R^3$, $R^4$, $R^9$, p and X are as defined above.

This reaction is carried out in the presence of a palladium catalyst, a copper salt and a base. This reaction may be carried out in the same manner as the step (21) in the process for intermediate [2].

Preferred embodiments of the pesticide containing the Invention Compound will be described below. The pesticide containing the Invention Compound may, for example, be an insecticide. The insecticide may, for example, be an agent to control insects, mites, nematodes or soil pests which become problematic in the agricultural and horticultural fields, i.e. an agricultural and horticultural insecticide, miticide, nematicide or soil pesticide. Further, it may be an agent for controlling harmful external parasites which are parasitic on the body surface (the back, axillae, abdomen, inside of thigh, or the like) of host animals such as pet animals, farm animals or poultry, i.e. an agent for controlling animal ectoparasites.

The Invention Compound is useful as agricultural or horticultural insecticides, miticides, nematicides, or soil pesticides. The compound is specifically effective in controlling: pests including aphids such as green peach aphid and cotton aphid, agricultural pests such as diamondback moth, cutworm, common cutworm, codling moth, bollworm, tobacco budworm, gypsy moth, rice leafroller, smaller tea tortrix, colorado potato beetle, cucurbit leaf beetle, boll weevil, planthoppers, leafhoppers, scales, stinkbugs, whiteflies, thrips, grasshoppers, anthomyiids, scarabaeidae, black cutworm, turnip moth, and ants, gastropods such as slugs and snails, sanitary pests such as house tick, cockroaches, house fly, and common house mosquito, stored grain pests such as angoumois grain moth, azuki bean weevil, red flour beetle, and tenebrionids, and clothing or house pests such as clothes moth, black carpet beetle, and termites; mites including plant-parasitic mites such as twospotted spider mite, carmine spider mite, kanzawa spider mite, citrus red mite, European red mite, broad mite, pink citrus rust mite, and bulb mite, and mites feeding on household dust, such as Tyrophagus putrescentiae, Dermotophagoides farinae, and Chelacaropsis moorei; nematodes including plant-parasitic nematodes such as root-knot nematodes, cyst nematodes, root-lesion nematodes, rice white-tip nematode, strawberry bud nematode, and pine wood nematode; and soil pests including isopods such as wood louse and pill bug. The agricultural or horticultural insecticide, miticide, nematicide, or soil pesticide which comprises the Invention Compound is especially effective in controlling plant-parasitic mites, agricultural pests, plant-parasitic nematodes, or the like, and is more highly effective in controlling plant-parasitic mites and agricultural pests, among those. Consequently, the agent according to the present invention is exceedingly useful as insecticides or miticides. Furthermore, the agricultural or horticultural insecticide, miticide, nematicide, or soil pesticide which comprises the Invention Compound is effective also in controlling various pests which are resistant to chemicals such as organophosphorus pesticides, carbamate pesticides, synthetic pyrethroid pesticides, neonicotinoid pesticides, or the like. Moreover, since the Invention Compound is excellent in terms of the property of infiltrating and migrating, not only soil insect pests, mites, nematodes, gastropods, isopods, or the like, but also pests living in or on the stalks and leaves can be controlled by treating the soil with the agricultural or horticultural insecticide, miticide, nematicide, or soil pesticide which comprises the Invention Compound.

Other preferable embodiments of the insecticide which comprises the Invention Compound may include an agricultural or horticultural insecticide, miticide, nematicide, or soil pesticide for comprehensively controlling the plant-parasitic mites, agricultural pests, plant-parasitic nematodes, gastropods, soil pests, or the like, shown above.

Usually, the agricultural or horticultural insecticide, miticide, nematicide, or soil pesticide which comprises the Invention Compound is produced by mixing the compound with various agricultural additives to formulate the compound into various forms such as dusts, granules, water dispersible granules, wettable powders, water-based suspension concentrates, oil-based suspension concentrates, water-soluble granules, water-soluble powders, emulsifiable concentrates, soluble concentrates, pastes, aerosols, ultra low volume formulations, or the like, and is then used. The agent according to the present invention can be formulated into any preparations which are in common use in this field, so long as the preparation is suitable for the objects of the present invention. Examples of the additives for use in such preparations may include: solid carriers such as diatomaceous earth, slaked lime, calcium carbonate, talc, white carbon, kaolin, bentonite, kaolinite, sericite, clay, sodium carbonate, sodium bicarbonate, sodium sulfate, zeolite, and starch; solvents such as water, toluene, xylene, sorbent naphtha, dioxane, acetone, isophorone, methyl isobutyl ketone, chlorobenzene, cyclohexane, dimethyl sulfoxide, N,N-dimethylformamide, N,N-dimethylacetamide, N-methyl-2-pyrrolidone, and alcohols; anionic surfactants such as fatty acid salts, benzoate, alkylsulfosuccinate, dialkylsulfosuccinate, polycarboxylate, salts of alkylsulfuric acid ester, alkylsulfate, alkylarylsulfate, alkyl diglycol ether sulfate, salts of alcohol sulfuric acid ester, alkylsulfonate, alkylarylsulfonate, arylsulfonate, ligninsulfonate, (alkyldiphenyl ether)disulfonate, polystyrenesulfonate, salts of alkylphosphoric acid ester, alkylarylphosphate, styrylarylphosphate, salts of polyoxyethylene alkyl ether sulfuric acid ester, polyoxyethylene alkylaryl ether sulfate, salts of polyoxyethylene alkylaryl ether sulfuric acid ester, polyoxyethylene alkyl ether phosphate, salts of polyoxyethylene alkylaryl phosphoric acid ester, and salts of naphthalenesulfonic acid condensed with formaldehyde; nonionic surfactants such as sorbitan fatty acid esters, glycerin fatty acid esters, fatty acid polyglycerides, fatty acid alcohol polyglycol ethers, acetylene glycol, acetylene alcohol, oxyalkylene block polymers, polyoxyethylene alkyl ethers, polyoxyethylene alkylaryl ethers, polyoxyethylene styrylaryl ethers, poly(oxyethylene glycol) alkyl ethers, polyethylene glycol, polyoxyethylene fatty acid esters, polyoxyethylene sorbitan fatty acid esters, polyoxyethylene glycerin fatty acid esters, polyoxyethylene hydrogenated castor oil, and polyoxypropylene fatty acid esters; and vegetable oils and mineral oils, such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. One or more of these additive ingredients can be suitably selected and used, so long as the use thereof does not depart from the objects of the present invention. It is also possible to use additives suitably selected from additives which are known in this field other than the additives shown above. For example, use can be made of various additives in common use, such as fillers, thickeners, anti-settling agents, anti-freezing agents, dispersion stabilizers, safeners, and anti-mold agents. The mixing ratio (weight ratio) of the Invention Compound to such various additives may be from 0.001:99.999 to 95:5, preferably from 0.005:99.995 to 90:10. When those preparations are actually used, the preparations can be used as such or be used after the preparations are diluted to a given concentration with a diluent such as water, and various spreading agents (surfactants, vegetable oils, mineral oils, or the like) are added thereto according to need.

Methods for applying the agricultural or horticultural insecticide, miticide, nematicide, or soil pesticide which comprises the Invention Compound cannot be unconditionally specified because the methods depend on the weather conditions, type of preparation, time for application, application site, kind of the disease and pest, state of infestation thereof, or the like. However, the concentration of active-ingredient to be applied may be generally 0.05-800,000 ppm, preferably 0.5-500,000 ppm, and the amount of the preparation to be applied per unit area may be 0.05-50,000 g, preferably 1-30,000 g, in terms of the amount of the Invention Compound per hectare. Methods for controlling pests, mites, nematodes, or soil pests, in particular, for controlling plant-parasitic mites, agricultural pests, or plant-parasitic nematodes, by such application methods are included in the present invention.

Various preparations of the agricultural or horticultural insecticide, miticide, nematicide, or soil pesticide which comprises the Invention Compound or dilutions thereof can be usually applied by an application method in general use. Namely, the preparations or dilutions can be applied by aerial application (e.g., spraying, misting, atomizing, granule scattering, application to water surface, or the like), application to soil (mixing, irrigation, or the like), surface application (coating, dust coating, covering, or the like), use of an impregnated toxic bait, or the like. It is also possible to use a method in which the active ingredient is supplied as a mixture thereof with a feed to a farm animal to inhibit pests, in particular, insect pests, from breeding and growing on the excreta. Furthermore, the Invention Compound can be applied by the so-called ultra low volume application method. In this method, the active ingredient can be contained in a concentration of 100%.

The agricultural or horticultural insecticide, miticide, nematicide, or soil pesticide which comprises the Invention Compound can be used as a mixture or in combination with other agricultural chemicals, fertilizers, safeners, or the like, and there are cases where the agent according to the present invention shows an even better effect or function when used in such manner. Examples of the other agricultural chemicals may include herbicides, insecticides, miticides, nematicides, soil pesticides, bactericides, antiviral agents, attractants, antibiotics, plant hormones, and plant growth regulators. In particular, an insecticidal composition in which the Invention Compound is used as a mixture or in combination with one or more active-ingredient compounds for other agricultural chemicals can attain preferable improvements in application range, time for chemical treatment, control activity, or the like. Incidentally, the Invention Compound and the active-ingredient compound(s) for other agricultural chemicals may be separately formulated and thereafter mixed together just before application thereof, or may be formulated together and used. Such insecticidal compositions are included in the present invention.

Examples of the active-ingredient compounds (common name, partly including names under application; or test codes according to Japan Plant Protection Association) for the insecticides, miticides, nematicides, or soil pesticides among the other agricultural chemicals include: organic phosphoric acid ester compounds such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim and triazophos;

carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives such as cartap, thiocyclam, bensultap, thiosultap-sodium, thiosultap-disodium, monosultap, bisultap and thiocyclam hydrogen oxalate; organic chlorine compounds such as dicofol, tetradifon, endosulfan, dienochlor and dieldrin;

organometallic compounds such as fenbutatin oxide and cyhexatin;

pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, flumethrin and decamethrin;

benzoylurea compounds such as diflubenzuron, chlorfluazuron, teflubenzuron, flufenoxuron, triflumuron, hexaflumuron, lufenuron, novaluron, noviflumuron, bistrifluron and fluazuron;

juvenile hormone-like compounds such as methoprene, pyriproxyfen, fenoxycarb and diofenolan;

pyridazinone compounds such as pyridaben;

pyrazole compounds such as fenpyroximate, fipronil, tebufenpyrad, ethiprole, tolfenpyrad, acetoprole, pyrafluprole and pyriprole;

neonicotinoid compounds such as imidacloprid, nitenpyram, acetamiprid, thiacloprid, thiamethoxam, clothianidin, nidinotefuran, dinotefuran and nithiazine;

hydrazine compounds such as tebufenozide, methoxyfenozide, chromafenozide and halofenozide;

pyridine compounds such as pyridalyl and flonicamid;

cyclic keto-enol compounds such as spirodiclofen, spiromesifen and spirotetramat;

strobilurin compounds such as fluacrypyrim;

pyridinamine compounds such as flufenerim;

dinitro compounds;

organic sulfur compounds;

urea compounds;

triazine compounds;

hydrazone compounds; and other compounds including flometoquin, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyanaliliprole, cyenopyrafen, pyrifluquinazon, fenazaquin, amidoflumet, sulfluramid, hydramethylnon, metaldehyde, ryanodine, verbutin, AKD-1022, chlorobenzoate, thiazolylcinnanonitrile, sulfoxaflor, fluensulfone, 3-bromo-N-(4-chloro-2-(1-cyclopropylethylcarbamoyl)-6-methylphenyl)-1-(3-chloropyridin-2-yl)-1H-pyrazole-5-carboxamide, 3-bromo-N-(2-bromo-4-chloro-6-(cyclopropylmethylcarbamoyl)phenyl)-1-(3-chloropyridin-2-yl)-1H-pyrazole-5-carboxamide, 3-bromo-N-(4-chloro-2-methyl-6-(methylcarbamoyl)phenyl)-1-(3-chloropyridin-2-yl)-1H-pyrazole-5-carboxamide, and 3-bromo-1-(3-chloropyridin-2-yl)-N-(4-cyano-2-methyl-6-(methylcarbamoyl)phenyl)-1H-pyrazole-5-carboxamide.

Furthermore, the Invention Compound can be used as a mixture or in combination with: Furher, *Bacillus thuringiensis aizawai, Bacillus thuringiensis kurstaki, Bacillus*

*thuringiensis israelensis, Bacillus thuringiensis japonensis, Bacillus thuringiensis tenebrionis,* insecticidal crystal proteins produced by *Bacillusthuringiensis,* microbial pesticides such as entomopathogenic viral agents, entomopathogenic filamentous agents, and nematopathogenic filamentous agents, antibiotics and semisynthetic antibiotics such as avermectin, emamectin Benzoate, milbemectin, milbemycin, spinosad, ivermectin, lepimectin, DE-175, abamectin, emamectin and spinetoram; natural substances such as azadirachtin and rotenone; repellents such as deet, or the like.

Examples of the active-ingredient compounds (common name, partly including names under application; or test codes according to Japan Plant Protection Association) for the bactericides among the other agricultural chemicals may include: anilinopyrimidine compounds such as mepanipyrim, pyrimethanil and cyprodinil;

triazolopyrimidine compounds such as 5-chloro-7-(4-methylpiperidin-1-yl)-6-(2,4,6-trifluorophenyl)[1,2,4]triazolo[1,5-a]pyrimidine;

pyridinamine compounds such as fluazinam;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, azaconazole, triticonazole and imazalil;

quinoxaline compounds such as quinomethionate;

dithiocarbamate compounds such as maneb, zineb, mancozeb, polycarbamate, metiram, propineb and thiram;

organic chlorine compounds such as fthalide, chlorothalonil and quintozene;

imidazole compounds such as benomyl, thiophanate-methyl, carbendazim, thiabendazole, fuberiazole and cyazofamid;

cyanoacetamide compounds such as cymoxanil;

anilide compounds such as metalaxyl, metalaxyl-M (mefenoxam), oxadixyl, ofurace, benalaxyl, benalaxyl-M (kiralaxyl, chiralaxyl), furalaxyl, cyprofuram, carboxin, oxycarboxin, thifluzamide, boscalid, bixafen, isotianil, tiadinil and sedaxane;

sulfamide compounds such as dichlofluanid;

copper compounds such as cupric hydroxide and oxine copper;

isoxazole compounds such as hymexazol;

organophosphorus compounds such as fosetyl-Al, tolclofos-Methyl, S-benzyl O,O-diisopropyl phosphorothioate, O-ethyl S,S-diphenyl phosphorodithioate, aluminum ethyl hydrogen phosphonate, edifenphos and iprobenfos;

phthalimide compounds such as captan, captafol and folpet;

dicarboximide compounds such as procymidone, iprodione and vinclozolin;

benzanilide compounds such as flutolanil, mepronil and benodanil;

amide compounds such as penthiopyrad, penflufen, furametpyr, isopyrazam, silthiopham, fenoxanil, fenfuram, fluxapyroxad and benzovindiflupyr;

benzamide compounds such as fluopyram and zoxamide;

piperazine compounds such as triforine;

pyridine compounds such as pyrifenox and pyrisoxazole;

carbinol compounds such as fenarimol and nuarimol;

piperidine compounds such as fenpropidin;

morpholine compounds such as fenpropimorph and tridemorph;

organotin compounds such as fentin hydroxide and fentin acetate;

urea compounds such as pencycuron;

cinnamic acid compounds such as dimethomorph and flumorph;

phenyl carbamate compounds such as diethofencarb;

cyanopyrrole compounds such as fludioxonil and fenpiclonil;

strobilurin compounds such as azoxystrobin, kresoxim-methyl, metominostrobin, trifloxystrobin, picoxystrobin, oryzastrobin, dimoxystrobin, pyraclostrobin, fluoxastrobin, Enestroburin, Pyraoxystrobin, Pyrametostrobin, coumoxystrobin, enoxastrobin, fenaminstrobin, flufenoxystrobin and triclopyricarb;

oxazolidinone compounds such as famoxadone;

thiazolecarboxamide compounds such as ethaboxam;

valine amide compounds such as iprovalicarb and benthiavalicarb-isopropyl;

acylamino acid compounds such as methyl N-(isopropoxycarbonyl)-L-valyl-(3RS)-3-(4-chlorophenyl)-β-alaninate (valiphenalate);

imidazolinone compounds such as fenamidone;

hydroxyanilide compounds such as fenhexamid;

benzenesulfonamide compounds such as flusulfamide;

oxime ether compounds such as cyflufenamid;

anthraquinone compounds;

crotonic acid compounds;

antibiotics such as validamycin, kasugamycin and polyoxins;

guanidine compounds such as iminoctadine and dodine;

quinoline compounds such as tebufloquin;

thiazolidine compounds such as flutianil;

Sulfur compounds such as Sulfur; and other compounds including pyribencarb, isoprothiolane, pyroquilon, diclomezine, quinoxyfen, propamocarb hydrochloride, chloropicrin, dazomet, metam-sodium, metrafenone, nicobifen, UBF-307, diclocymet, proquinazid, am isulbrom (am ibromdole), mandipropamid, fluopicolide, carpropamid, meptyldinocap, isofetamid, pyriofenone, ferimzone, spiroxamine, fenpyrazamine, ametoctradin, valifenalate, oxathiapiprolin, tolprocarb, NK-1001, SB-4303, MIF-1001, MIF-1002, BAF-1107, NF-171, SYJ-247, and NNF-0721.

Other examples of agricultural chemicals which can be used as a mixture or in combination with the Invention Compound may include active-ingredient compounds for herbicides, in particular, herbicides of the soil application type, such as those given in The Pesticide Manual (15th edition).

Examples of the ectoparasites may include animal-parasitic mites and fleas. Since the number of kinds of these parasites is exceedingly large and it is difficult to enumerate all, examples thereof are shown below.

Examples of the animal-parasitic mites may include: ticks such as *Boophilus microplus, Rhipicephalus sanquineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus,* and *Dermacentor taiwanesis; Dermanyssus pallinae;* northern fowl mites such as *Orithonyssus sylviarum* and *Ornithonyssus bursa;* trombiculids such as *Eutrombicula wichmanni, Leptotrombidium akamushi, Leptotrombidium pallidum, Leptotrombidium fuii,*

*Leptotrombidium tosa, Neotrombicula autumnalis, Eutrombicula alfreddugesi,* and *Helenicula miyagawai;* cheyletids such as *Cheyletiella yasguri, Cheyletiella parasitivorax,* and *Cheyletiella blakei;* sarcoptids such as *Psoroptes cuniculi, Chorioptes bovis, Otodectes cynotis, Sarcoptes scabiei,* and *Notoedres cati;* and demodexes such as *Demodex canis.* The agent for controlling animal ectoparasites, which comprises the Invention Compound, is especially effective in controlling ticks among those.

Examples of the animal-parasitic fleas may include ectoparasitic wingless insects belonging to the order *Siphonaptera.* More specific examples thereof may include fleas belonging to the families Pulicidae, Ceratephyllus, and the like. Examples of the fleas belonging to the family Pulicidae may include *Ctenocephalides canis, Ctenocephalides felis, Pulex irritants, Echidnophaga gallinacea, Xenopsylla cheopis, Leptopsylla semis, Nosopsyllus fasciatus,* and *Monopsyllus anisus.* The agent for controlling animal ectoparasites, which comprises the Invention Compound, is especially effective in controlling fleas belonging to the family Pulicidae among those, in particular, *Ctenocephalides canis, Ctenocephalides felis,* and the like.

Examples of other ectoparasites may include: lice such as cattle louse, horse louse, sheep louse, longnosed cattle louse, and head louse; chewing lice such as dog chewing louse; and blood-sucking dipterous pests such as horseflies, biting midges, and black flies.

Examples of the host animals may include various pet animals, farm animals, and poultry. More specific examples thereof may include dogs, cats, mice, rats, hamsters, guinea pigs, squirrels, rabbits, ferrets, birds (e.g., pigeons, parrots, hill mynas, Java sparrows, parakeets, society finches, canaries, or the like), cattle, horses, pigs, sheep, ducks, and chickens. The agent for controlling animal ectoparasites, which comprises the Invention Compound, is effective in controlling pests or mites which are ectoparasitic on pet animals or farm animals, among those. The agent is especially effective for dogs, cats, cattle, or horses among the pet animals and farm animals.

In the case where the Invention Compound is used as an agent for controlling animal ectoparasites, the compound may be used as such or can be used after having been formulated together with adequate additives into various forms such as dusts, granules, tablets, powders, capsules, liquid formulations, emulsions, water-based suspensions, oil-based suspensions, wettable powders, small grains, or the like. Besides being formulated into such forms, the Invention Compound can be formulated into any preparations which are in common use in this field, so long as the preparation is suitable for the objects of the present invention. Examples of the additives for use in the preparations may include: the anionic surfactants and nonionic surfactants shown above as examples of the additives for formulating the agricultural or horticultural insecticide, miticide, nematicide, or soil pesticide; cationic surfactants such as cetyltrimethylammonium bromide; solvents such as water, acetone, acetonitrile, N-methylacetamide, N,N-dimethylacetamide, N,N-dimethylformamide, 2-pyrrolidone, N-methyl-2-pyrrolidone, kerosene, triacetin, methanol, ethanol, isopropanol, benzyl alcohol, ethylene glycol, propylene glycol, polyethylene glycol, liquid polyoxyethylene glycol, butyl diglycol, ethylene glycol monomethyl ether, ethylene glycol monoethyl ether, diethylene glycol monoethyl ether, diethylene glycol n-butyl ether, dipropylene glycol monomethyl ether, and dipropylene glycol n-butyl ether; antioxidants such as butylhydroxyanisole, butylhydroxytoluene, ascorbic acid, sodium hydrogen metasulfite, propyl gallate, and sodium thiosulfate; film-forming agents such as polyvinylpyrrolidone, polyvinyl alcohol, and copolymers of vinyl acetate and vinylpyrrolidone; the vegetable oils and mineral oils shown above as examples of the additives for formulating the agricultural or horticultural insecticide, miticide, nematicide, or soil pesticide; and carriers such as lactose, sucrose, glucose, starch, flour, corn flour, soybean oil cake, de-fatted rice bran, calcium carbonate, and other commercial raw materials for feeds. One or more of these additive ingredients can be suitably selected and used, so long as the use thereof does not depart from the objects of the present invention. It is also possible to use additives suitably selected from additives which are known in this field other than the additives shown above. Furthermore, use can be made of one or more ingredients suitably selected from the various additives mentioned above for use in the agricultural and horticultural fields.

The mixing ratio (weight ratio) of the Invention Compound to such various additives is usually about from 0.1:99.9 to 90:10. When those preparations are actually used, the preparations can be used as such or be used after the preparations are diluted to a given concentration with a diluent such as water, and various spreading agents (surfactants, vegetable oils, mineral oils, or the like) are added thereto according to need.

The Invention Compound is administered to the host animal perorally or parenterally. Examples of methods for the peroral administration may include a method of administering a tablet, liquid formulation, capsule, wafer, biscuit, minced meat, another feed, or the like which comprises the Invention Compound. Examples of methods for the parenteral administration may include: a method in which the Invention Compound is formulated into an adequate preparation and this preparation is introduced into the body by administration by intravenous injection, intramuscular administration, intracutaneous administration, subcutaneous administration, or the like; a method in which the Invention Compound is administrated to the body surface by a spot-on treatment, pour-on treatment, spraying, a chemical bath or the like; and a method in which a resin piece or the like which comprises the Invention Compound is buried under the skin of the host animal.

The amount of the Invention Compound to be administrated to a host animal varies depending on the method of administration, purpose of the administration, condition of the disease, or the like. However, it is adequate to administer the compound in a dose of usually 0.01 mg to 100 g, preferably 0.1 mg to 10 g, per kg of the body weight of the host animal.

Methods for controlling animal ectoparasites, by the method or amount of administration as described above are included in the present invention.

In the present invention, there are cases where by thus controlling noxious animal ectoparasites, the various diseases of the host animals which are attributable to the parasites can be prevented or remedied. Consequently, prophylactic agents for ectoparasitic animal diseases, comprising the Invention Compound as an active ingredient, and methods for preventing or remedying ectoparasitic animal diseases therewith are included in the present invention.

When the Invention Compound is used as an agent for controlling animal ectoparasites, the compound can be used as a mixture or in combination with various kinds of vitamins, minerals, amino acids, nutrients, preparations of ferments, antipyretic agents, sedative agents, anti-inflammatory agents, bactericides, colorants, fragrances, preservatives, or the like, together with additives. The Invention Compound can be used as a mixture or in combination with other various drugs for animals or various agricultural chemicals, such as, for example, anthelminthic agents, anticoccidial agents, insecticides, miticides, agents for killing fleas, nematicides, bactericides, antibacterial agents, or the like, according to need, and there are cases where the Invention Compound shows an even better effect when used in such manner. Compositions for controlling animal ectoparasites, the compositions comprising the Invention Compound as a mixture or in combination with various ingredients such as those shown above, and methods for controlling animal ectoparasites, using the compositions are included in the present invention.

Now, preferred embodiments of the phenoxyalkylbenzamide compound or its salt of the present invention are exemplified, however, the present invention is not limited thereto.

(1) The phenoxyalkylbenzamide compound of the above formula (I) or its salt.

(2) The compound or its salt according to (1), which is represented by the formula (I-1).

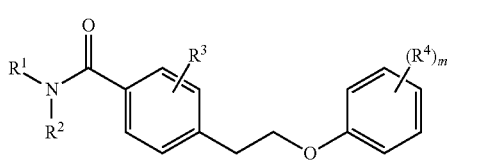

(I-1)

wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl, alkylcarbonylalkyl, Y or alkyl substituted by Y;

Y is a saturated or unsaturated cyclic group which may be substituted by Z, and the cyclic group may contain one or two hetero atoms selected from a nitrogen atom which may be substituted by alkyl, an oxygen atom and a sulfur atom;

Z is halogen, alkyl, haloalkyl, alkoxy, haloalkoxy, cyano, amino, alkoxycarbonylamino or nitro;

$R^2$ is a hydrogen atom, alkyl, alkylcarbonyl or alkylcarbonylalkyl; or $R^1$ and $R^2$ may form, together with the adjacent nitrogen atom, a cyclic structure which may be substituted by Z, and the cyclic structure may further contain one hetero atom selected from a nitrogen atom which may be substituted by alkyl, an oxygen atom and a sulfur atom;

$R^3$ is a hydrogen atom, halogen, alkyl, haloalkyl, alkylcarbonyl, alkoxycarbonyl, alkoxy, amino, monoalkylamino, dialkylamino, cyano or nitro;

$R^4$ is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano, nitro, phenoxy which may be substituted by $R^9$, phenyl which may substituted by $R^9$, or a heterocyclic group which may be substituted by $R^9$;

$R^8$ is hydrogen, alkyl, halogen, alkoxy, alkylcarbonyl, alkoxycarbonyl, amino, monoalkylamino, dialkylamino, trialkylsilyl or Y;

$R^9$ is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano or nitro; and m is an integer of from 0 to 5.

(3) The compound or its salt according to (2), wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl, Y or alkyl substituted by Y;

Y is a saturated or unsaturated cyclic group which may be substituted by Z, and the cyclic group may contain one or two hetero atoms selected from a nitrogen atom which may be substituted by alkyl, an oxygen atom and a sulfur atom;

Z is halogen, alkyl, haloalkyl, alkoxy, haloalkoxy, cyano or nitro;

$R^2$ is a hydrogen atom, alkyl or alkylcarbonyl;

$R^4$ is halogen, alkyl, haloalkyl, alkoxy, haloalkoxy, alkylcarbonyl, alkylthio, haloalkylthio, alkylsulfinyl, haloalkylsulfinyl, alkylsulfonyl, haloalkylsulfonyl, amino, monoalkylamino, dialkylamino, cyano or nitro; and m is an integer of from 0 to 3.

(4) The compound or its salt according to (2), wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl or alkyl substituted by Y;

$R^3$ is a hydrogen atom, halogen, alkyl, haloalkyl, alkoxy, amino, cyano or nitro; and $R^4$ is halogen, alkyl, haloalkyl, alkoxy, haloalkoxy, alkylcarbonyl, alkylthio, haloalkylthio, alkylsulfinyl, haloalkylsulfinyl, alkylsulfonyl, haloalkylsulfonyl, cyano or nitro.

(5) The compound or its salt according to (2), wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl, or alkyl substituted by Y;

Y is a saturated or unsaturated 3- to 7-membered ring, and the 3- to 7-membered ring may contain one or two hetero atoms selected from a nitrogen atom which may be substituted by alkyl, an oxygen atom and a sulfur atom;

$R^3$ is a hydrogen atom, halogen, alkyl, haloalkyl, alkoxy or cyano;

$R^4$ is halogen, alkyl, haloalkyl, alkoxy, haloalkoxy, alkylcarbonyl, alkylthio, haloalkylthio, alkylsulfinyl, haloalkylsulfinyl, alkylsulfonyl, haloalkylsulfonyl, cyano or nitro; and m is an integer of from 0 to 2.

(6) The compound or its salt according to (1) or (2), wherein $R^1$ is a hydrogen atom, alkyl, alkenyl, alkynyl, haloalkyl, alkoxyalkyl, dialkylaminoalkyl, dialkylamino, alkylthioalkyl, cyanoalkyl, alkylcarbonylalkyl, Y or alkyl substituted by Y.

(7) The compound or its salt according to (6), wherein $R^1$ is a hydrogen atom, alkyl, alkenyl, alkynyl, haloalkyl, alkoxyalkyl, dialkylaminoalkyl, alkylthioalkyl, cyanoalkyl, Y or alkyl substituted by Y.

(8) The compound or its salt according to (1) or (2), wherein $R^2$ is a hydrogen atom or alkyl.

(9) The compound or its salt according to (1), (2) or (3), wherein $R^3$ is a hydrogen atom, halogen, alkyl, amino, cyano or nitro.

(10) The compound or its salt according to (1), wherein each of $R^4$ and $R^7$ which are independent of each other, is halogen, alkyl, haloalkyl, alkoxy, haloalkoxy, alkylcarbonyl, alkylthio, haloalkylthio, alkylsulfinyl, alkylsulfonyl, amino, dialkylamino, cyano, nitro or phenoxy which may be substituted by $R^9$.

(11) The compound or its salt according to (1), (2), (3), (4), (5) or (6), wherein $R^4$ is halogen, alkyl, haloalkyl, alkoxy, haloalkoxy, alkylcarbonyl, alkylthio, haloalkylthio, alkylsulfinyl, alkylsulfonyl, amino, dialkylamino, cyano, nitro or phenoxy which may be substituted by $R^9$.

(12) The compound or its salt according to (11), wherein $R^4$ is halogen, alkyl, haloalkyl, alkoxy, haloalkoxy, alkylcarbonyl, dialkylamino or cyano.

(13) The compound or its salt according to (11), wherein $R^4$ is halogen, alkyl, haloalkyl, alkoxy, haloalkoxy, alkylcarbonyl or cyano.

(14) The compound or its salt according to (1), which is represented by the formula (I-2):

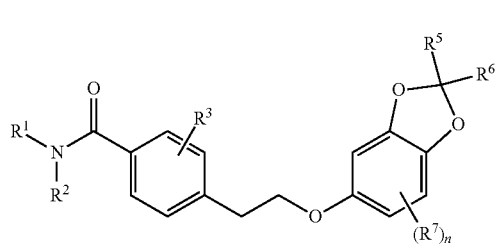

(I-2)

wherein $R^1$, $R^2$, $R^3$, $R^5$, $R^6$, $R^7$ and n are as defined above.

(15) The compound or its salt according to (1), which is represented by the formula (I-3):

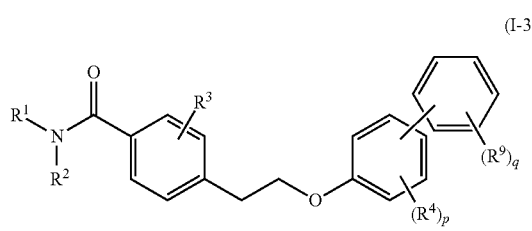

(I-3)

wherein $R^1$, $R^2$, $R^3$, $R^4$, $R^9$, p and q are as defined above.

(16) The compound or its salt according to (15), which is represented by the formula (I-3a):

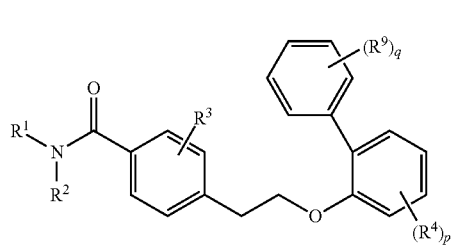

(I-3a)

wherein $R^1$, $R^2$, $R^3$, $R^4$, $R^9$, p and q are as defined above.

(17) The compound or its salt according to (15), which is represented by the formula (I-3b):

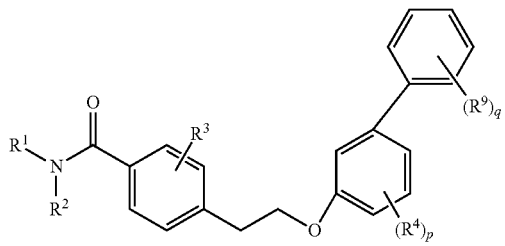

(I-3b)

wherein $R^1$, $R^2$, $R^3$, $R^4$, $R^9$, p and q are as defined above.

(18) The compound or its salt according to (15), which is represented by the formula (I-3c):

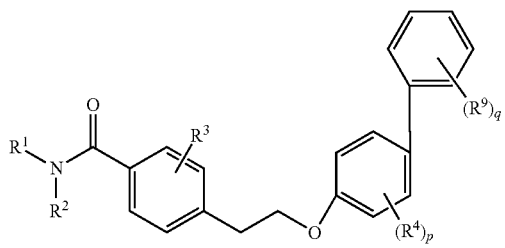

(I-3c)

wherein $R^1$, $R^2$, $R^3$, $R^4$, $R^9$, p and q are as defined above.

(19) The compound or its salt according to (1), which is represented by the formula (I-4):

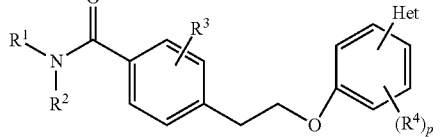

(I-4)

wherein $R^1$, $R^2$, $R^3$, $R^4$, Het and p are as defined above, and r is an integer of from 0 to 4.

(20) The compound or its salt according to (19), which is represented by the formula (I-4a):

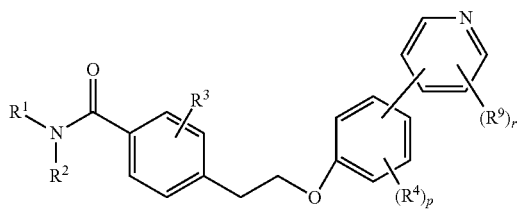

(I-4a)

wherein $R^1$, $R^2$, $R^3$, $R^4$, $R^9$ and p are as defined above, and r is an integer of from 0 to 4.

(21) The compound or its salt according to (20), which is represented by the formula (I-4a-1):

(I-4a-1)

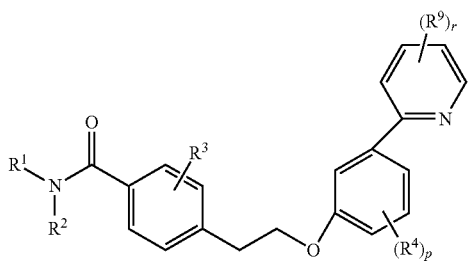

wherein $R^1$, $R^2$, $R^3$, $R^4$, $R^9$, p and r are as defined above.

(22) The compound or its salt according to (20), which is represented by the formula (I-4a-2):

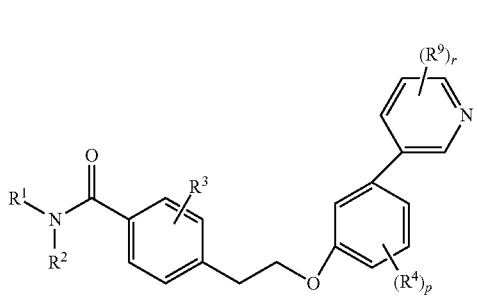

wherein $R^1$, $R^2$, $R^3$, $R^4$, $R^9$, p and r are as defined above.

(23) The compound or its salt according to (19), which is represented by the formula (I-4b):

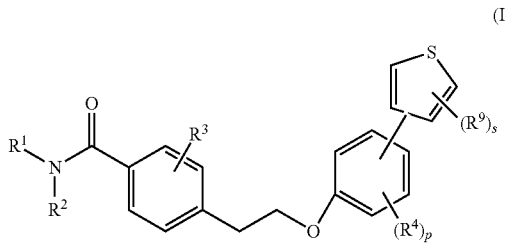

wherein $R^1$, $R^2$, $R^3$, $R^4$, $R^9$ and p are as defined above, and s is an integer of from 0 to 3.

(24) The compound or its salt according to (23), which is represented by the formula (I-4b-1):

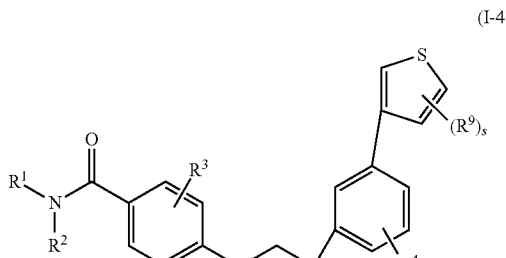

wherein $R^1$, $R^2$, $R^3$, $R^4$, $R^9$, p and s are as defined above.

(25) The compound or its salt according to (23), which is represented by the formula (I-4b-2):

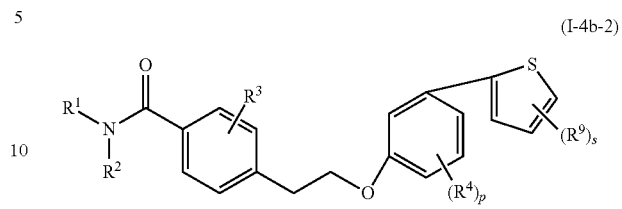

wherein $R^1$, $R^2$, $R^3$, $R^4$, $R^9$, p and s are as defined above.

(26) The compound or its salt according to (1), which is represented by the formula (I-5):

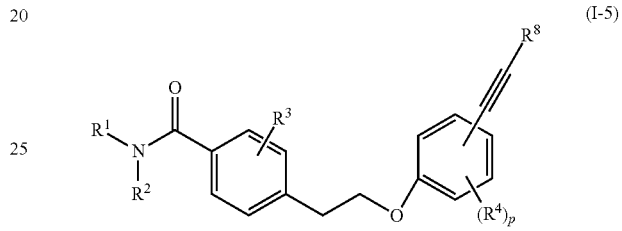

wherein $R^1$, $R^2$, $R^3$, $R^4$ and $R^8$ are as defined above, and p is an integer of from 0 to 4.

(27) The compound or its salt according to (26), which is represented by the formula (I-5a):

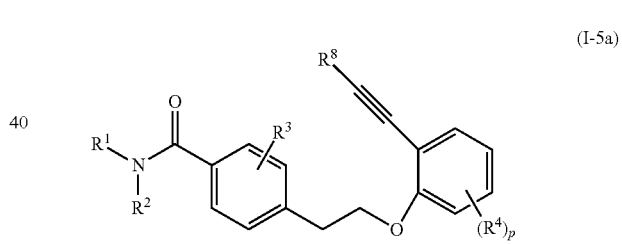

wherein $R^1$, $R^2$, $R^3$, $R^4$, $R^8$ and p are as defined above.

(28) The compound or its salt according to (26), which is represented by the formula (I-5b):

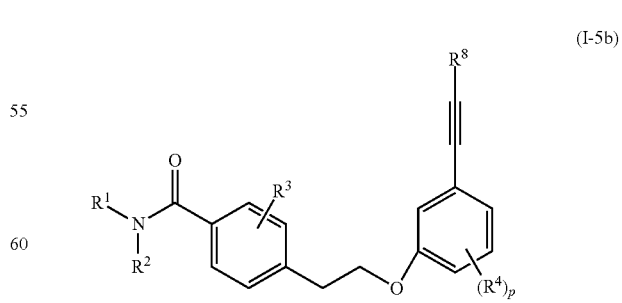

wherein $R^1$, $R^2$, $R^3$, $R^4$, Fe and p are as defined above.

(29) The compound or its salt according to (26), which is represented by the formula (I-5c):

(I-5c)

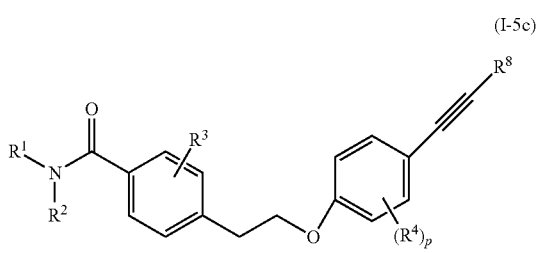

wherein $R^1$, $R^2$, $R^3$, $R^4$, $R^8$ and p are as defined above.
(30) The compound or its salt according to (11) or (15) to (29), wherein $R^4$ is halogen, alkyl, haloalkyl, alkoxy or haloalkoxy.
(31) The compound or its salt according to (15) to (25), wherein $R^4$ is halogen.
(32) The compound or its salt according to (1) or (14), wherein each of $R^5$ and $R^6$ which are independent of each other, is a hydrogen atom or halogen.
(33) The compound or its salt according to (1) or (14), wherein $R^7$ is halogen or alkyl.

EXAMPLES

Now, the present invention will be described in further detail with reference to Examples, but it should be understood that the present invention is by no means thereby restricted. Firstly, Preparation Examples for the Invention Compound will be described.

Preparation Example 1

Preparation of N-isobutyl-4-(2-(3-(trifluoromethoxy)phenoxy)ethyl)benzamide (Compound No. 1-24)

(1) 17.42 g (66.42 mmol) of triphenylphosphine was added at room temperature to a solution having 9.21 g (45.81 mmol) of 2-(4-bromophenyl)ethanol and 8.61 g (48.34 mmol) of 3-(trifluoromethoxy)phenol dissolved in 160 ml of THF, followed by stirring for 10 minutes. Then, 31.23 ml (68.41 mmol) of DEAD (2.2 M toluene solution) was dropwise added over a period of 20 minutes, followed by stirring further for 15 hours. The solvent was distilled off under reduced pressure, and the obtained crude product was purified by silica gel column chromatography (developing solvent: heptane/ethyl acetate=98/2 to 95/5, volume ratio, the same applies hereinafter) to obtain 14.10 g (yield: 85.2%) of 1-(4-bromophenethyloxy)-3-(trifluoromethoxy)benzene as a colorless oil. $^1$H-NMR(300 MHz, CDCl$_3$, δppm): 7.44(d, 2H, J=8.1Hz), 7.26(dd, 1H, J=8.1Hz, 8.1Hz), 7.16(d, 2H, J=8.1Hz), 6.81(d, 1H, J=8.1Hz), 6.80(d, 1H, J=8.1Hz), 6.75-6.71(br, 1H), 4.14(t, 2H, J=6.9Hz), 3.05(t, 2H, J=6.9Hz)

(2) A solution having 4.00 g (11.08 mmol) of 1-(4-bromophenethyloxy)-3-(trifluoromethoxy)benzene obtained in the above (1) dissolved in 100 ml of THF was cooled to −78° C. in a nitrogen atmosphere, and 13.9 ml of n-butyllithium (1.6 M hexane solution) was dropwise added over a period of 5 minutes, followed by stirring for 10 minutes. An excess amount of dry ice was added to the reaction solution, followed by stirring for 1 hour, and by stirring further for 1 hour while the temperature was naturally increased to room temperature. A 1M aqueous sodium hydroxide solution was dropwise added, THF was distilled off under reduced pressure, and then ethyl acetate was added. The organic layer was extracted twice with a 1M aqueous sodium hydroxide solution, and the aqueous layer was acidified with concentrated hydrochloric acid and extracted three times with ethyl acetate. The organic layer was washed with a saturated aqueous sodium chloride solution, dried over anhydrous sodium sulfate and subjected to filtration, and the solvent was distilled off under reduced pressure to obtain 3.34 g (yield: 92.4%) of 4-(2-(3-trifluoromethoxy)phenoxy)ethyl)benzoic acid as a white solid.

$^1$H-NMR(300 MHz, CDCl$_3$, δppm): 8.07(d, 2H, J=8.4Hz), 7.40(d, 2H, J=8.4Hz), 7.27(dd, 1H, J=8.4Hz, 8.1Hz), 6.82(d, 1H, J=8.1Hz), 6.81(d, 1H, J=8.4Hz), 6.75-6.71(br, 1H), 4.21(t, 2H, J=6.9Hz), 3.18(t, 2H, J=6.9Hz)

(3) 0.96 ml (9.62 mmol) of isobutylamine, 1.59 ml (14.44 mmol) of 4-methylmorpholine, 1.84 g (9.62 mmol) of 1-ethyl-3-(3-dimethylaminopropyl)carbodiimide hydrochloride and 1.47 g (9.62 mmol) of 1-hydroxybenzotriazole monohydrate were added to a solution having 1.57 g (4.81 mmol) of 4-(2-(3-(trifluoromethoxy)phenoxy)ethyl)benzoic acid obtained in the above (2) dissolved in 20 ml of DMF, followed by stirring at room temperature for 3 days. A saturated aqueous ammonium chloride solution and ethyl acetate were added, and the aqueous layer was extracted three times with ethyl acetate. The organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20 to 70/30) to obtain 1.83 g (yield: 99%) of the desired product as a pale yellow solid.

Preparation Example (Another Process) for Intermediate (4-(2-(3-(trifluoromethoxy)phenoxy)ethyl) benzoic acid in Preparation Example 1

(1) 4.65 ml (33.36 mmol) of triethylamine, 1.23 g (2.22 mmol) of 1,1'-bis(diphenylphosphino)ferrocene and 0.25 g (1.11 mmol) of palladium(II) acetate were added to a solution having 4.00 g (11.08 mmol) of 1-(4-bromophenethyloxy)-3-(trifluoromethoxy)benzene dissolved in 40 ml of methanol and 25 ml of DMF in a nitrogen atmosphere, and the system in the reactor was replaced with carbon monoxide, followed by stirring at 80° C. for 17 hours. A saturated aqueous ammonium chloride solution was added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=95/5 to 90/10) to obtain 1.97 g (yield: 52.3%) of methyl 4-(2-(3-(trifluoromethoxy)phenoxy)ethyl)benzoate as a pale yellow oil.

1H-NMR(300 MHz, CDCl$_3$, δppm): 8.00(d, 2H, J=8.1Hz), 7.35(d, 2H, J=8.1Hz), 7.26(dd, 1H, J=8.4Hz, 8.1Hz), 6.81(d, 1H, J=8.1Hz), 6.80(d, 1H, J=8.4Hz), 6.75-6.71(br, 1H), 4.19(t, 2H, J=6.9Hz), 3.91(s, 3H), 3.15(t, 2H, J=6.9Hz)

(2) An aqueous solution having 0.77 g (19.25 mmol) of sodium hydroxide dissolved in 20 ml of water was added to a solution having 1.75 g (5.14 mmol) of methyl 4-(2-(3-(trifluoromethoxy)phenoxy)ethyl)benzoate obtained in the above (1) dissolved in 10 ml of ethanol, followed by stirring at 100° C. for 1 hour. The reaction solution was acidified with a 1M hydrochloric acid to precipitate a solid. The solid was subjected to filtration, washed with water and dried to obtain 1.68 g (yield: 93.6%) of 4-(2-(3-(trifluoromethoxy)phenoxy)ethyl)benzoic acid as a white solid.

Preparation Example 2

Preparation of N-isobutyl-4-(2-(4-(trifluoromethoxy)phenoxy)ethyl)benzamide (Compound No. 1-25)

(1) 2.86 ml (28.53 mmol) of isobutylamine, 4.70 ml (42.79 mmol) of 4-methylmorpholine, 5.47 g (28.53 mmol) of 1-ethyl-3-(3-dimethylaminopropyl)carbodiimide hydrochloride and 4.37 g (28.53 mmol) of 1-hydroxybenzotriazole monohydrate were added to a solution having 4.0 g (14.26 mmol) of 4-(2-((tert-butyldimethylsilyl)oxy)ethyl) benzoic acid dissolved in 30 ml of DMF, followed by stirring at room temperature for 2 days. A saturated aqueous ammonium chloride solution and ethyl acetate were added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20 to 70/30) to obtain 2.74 g (yield: 57.3%) of N-isobutyl-4-(2-((tert-butyldimethylsilyl)oxy)ethyl)benzamide as a brown oil.

1H-NMR(500 MHz, CDCl$_3$, δppm): 7.68(d, 2H, J=8.5Hz), 7.27(d, 2H, J=8.5Hz), 6.19-6.01(br, 1H), 3.82(t, 2H, J=6.5Hz), 3.29(t, 2H, J=6.5Hz), 2.85(t, 2H, J=6.5Hz), 1.94-1.86(m, 1H), 0.98(d, 6H, J=6.0Hz), 0.86(s, 9H), −0.025 (s, 6H)

(2) 19 ml of water and 37 ml of acetic acid were added at room temperature to a solution having 2.74 g (8.17 mmol) of N-isobutyl-4-(2-((tert-butyldimethylsilyl)oxy)ethyl) benzamide obtained in the above (1) dissolved in 19 ml of THF, followed by stirring overnight. The solvent was distilled off under reduced pressure, ethyl acetate and a saturated aqueous sodium hydrogencarbonate solution were added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=50/50 to 20/80) to obtain 1.60 g (yield: 88.5%) of N-isobutyl-4-(2-hydroxyethyl)benzamide as a white solid.

[1] H-NMR(500 MHz, CDCl$_3$, δppm): 7.71(d, 2H, J=8.0Hz), 7.30(d, 2H, J=8.0Hz), 7.25-6.05(br, 1H), 3.89(t, 2H, J=6.5Hz), 3.29(t, 2H, J=6.5Hz), 2.92(t, 2H, J=6.5Hz), 1.93-1.86(m, 1H), 0.98(d, 6H, J=6.5Hz)

(3) 0.10 g (0.45 mmol) of N-isobutyl-4-(2-hydroxyethyl) benzamide obtained in the above (2), 0.12 g (0.68 mmol) of 4-(trifluoromethoxy)phenol and 0.24 g (0.90 mmol) of diphenyl(2-pyridyl)phosphine were dissolved in 4.5 ml of THF. Then, 0.18 g (0.90 mmol) of DBAD was added, followed by stirring overnight. 0.10 ml of water and 2.34 ml of trifluoroacetic acid were added, followed by stirring at room temperature for 2 hours. 0.5M hydrochloric acid and ethyl acetate were added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20 to 70/30) to obtain 0.17 g (yield: 98%) of the desired product as a brown solid.

Preparation Example (Another Process) for Intermediate (N-isobutyl-4-(2-hydroxyethyl)benzamide in Preparation Example 2

0.23 ml (2.25 mmol) of isobutylamine and 0.62 g (2.25 mmol) of DMT-MM were added to a solution having 0.34 g (2.05 mmol) of 4-(2-hydroxyethyl)benzoic acid dissolved in 8.0 ml of THF, followed by stirring at room temperature overnight. 0.5M hydrochloric acid and ethyl acetate were added, the aqueous layer was extracted three times with ethyl acetate, the organic layer was washed with a saturated aqueous sodium hydrogencarbonate solution and a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=50/50 to 20/80) to obtain 0.27 g (yield: 59.6%) of N-isobutyl-4-(2-hydroxyethyl)benzamide as a white solid.

Preparation Example 3

Preparation of N-isobutyl-4-(2-(3,4-(difluoromethylenedioxy)phenoxy)ethyl)benzamide (Compound No. 2-1)

(1) 3.79 ml (27.16 mmol) of triethylamine, 2.51 g (4.53 mmol) of 1,1'-bis(diphenylphosphino)ferrocene and 0.51 g (2.26 mmol) of palladium(II) acetate were added in a nitrogen atmosphere to a solution having 4.55 g (22.63 mmol) of 2-(4-bromophenyl)ethanol dissolved in 160 ml of ethanol and 100 ml of DMSO, and the system in the reactor was replaced with carbon monoxide, followed by stirring under normal pressure at 80° C. for 17 hours. A saturated aqueous ammonium chloride solution was added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=70/30) to obtain 4.62 g (yield: 82.4%) of ethyl 4-(2-hydroxyethyl)benzoate as a pale yellow oil.

$^1$H-NMR(300 MHz, CDCl$_3$, δppm): 8.00(d, 2H, J=8.4Hz), 7.31(d, 2H, J=8.4Hz), 4.37(q, 2H, J=7.2Hz), 3.93-3.86(m, 2H), 2.93(t, 2H, J=6.6Hz), 1.39(t, 3H, J=7.2Hz)

(2) 0.97 g (17.22 mmol) of potassium hydroxide, 0.20 g (0.42 mmol) of di-t-butyl(2',4',6'-triisopropyl-3,4,5,6-tetramethyl-(1,1'-biphenyl)-2-yl)phosphine and 0.09 g (0.10 mmol) of tris(dibenzylideneacetone)dipalladium(0) were added in a nitrogen atmosphere to a solution having 2.04 g (8.61 mmol) of 2,2-difluoro-5-bromobenzodioxolane dissolved in 5 ml of 1,4-dioxane and 5 ml of water, followed by stirring at 100° C. for 17 hours. 22 ml of 1M hydrochloric acid was added, and then ethyl acetate was added. The aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20) to obtain 1.42 g (yield: 94.8%) of 2,2-difluoro-5-hydroxybenzodioxolane as a pale yellow oil.
$^1$H-NMR(300 MHz, CDCl$_3$, δppm): 6.88(d, 1 H, J=8.7Hz), 6.62(d, 1H, J=2.4Hz), 6.48(dd, 1H, J=8.7Hz, 2.4Hz)

(3) 2.87 g (10.94 mmol) of triphenylphosphine was added to a solution having 1.50 g (7.72 mmol) of ethyl 4-(2-hydroxyethyl)benzoate obtained in the above (1) and 1.38 g (7.95 mmol) of 2,2-difluoro-5-hydroxybenzodioxolane obtained in the above (2) dissolved in 30 ml of THF, followed by stirring for 5 minutes. Then, 4.88 ml (10.73 mmol) of DEAD (2.2 M toluene solution) was added, followed by stirring further for 3 days. The solvent was distilled off under reduced pressure, the obtained crude product was purified by silica gel column chromatography (developing solvent: heptane/ethyl acetate=90/10) to obtain 1.79 g (yield: 66.1%) of ethyl 4-(2-(3,4-(difluoromethylenedioxy)phenoxy)ethyl)benzoate as a pale yellow solid.
$^1$H-NMR(300 MHz, CDCl$_3$, δppm): 8.01(d, 2H, J=8.4Hz), 7.35(d, 2H, J=8.4Hz), 6.92(dd, 1H, J=8.7Hz, 2.1Hz), 6.65(d, 1H, J=2.1Hz), 6.54(d, 1H, J=8.7Hz), 4.40-4.30(m, 2H), 4.18-4.05(m, 2H), 3.18-3.08(m, 2H), 1.44-1.30 (m, 3H)

(4) An aqueous solution having 0.80 g (20.10 mmol) of sodium hydroxide dissolved in 20 ml of water was added to a solution having 1.76 g (5.02 mmol) of ethyl 4-(2-(3,4-(difluoromethylenedioxy)phenoxy)ethyl)benzoate obtained in the above (3) dissolved in 20 ml of ethanol, followed by stirring at 100° C. for 1 hour. The reaction solution was acidified with 1M hydrochloric acid to precipitate a solid. The solid was subjected to filtration, washed with water and dried to obtain 1.52 g (yield: 93.9%) of 4-(2-(3,4-(difluoromethylenedioxy)phenoxy) ethyl)benzoic acid as a white solid.
$^1$H-NMR(300 MHz, CDCl$_3$, δppm): 8.07(d, 2H, J=8.4Hz), 7.39(d, 2H, J=8.4Hz), 6.93(d, 1H, J=8.7Hz), 6.66(d, 1H, J=2.4Hz), 6.54(dd, 1H, J=8.7Hz, 2.4Hz), 4.16(t, 2H, J=6.6Hz), 3.16(t, 2H, J=6.6Hz)

(5) 0.09 g (1.24 mmol) of isobutylamine, 0.20 ml (1.86 mmol) of 4-methylmorpholine, 0.24 g (1.24 mmol) of 1-ethyl-3-(3-dimethylaminopropyl)carbodiimide hydrochloride and 0.19 g (1.24 mmol) of 1-hydroxybenzotriazole monohydrate were added to a solution having 0.20 g (0.62 mmol) of 4-(2-(3,4-(difluoromethylenedioxy)phenoxy)ethyl)benzoic acid obtained in the above (4) dissolved in 4 ml of DMF, followed by stirring at room temperature for 3 days. A saturated aqueous ammonium chloride solution and ethyl acetate were added, the aqueous layer was extracted three times with ethyl acetate, the organic solvent was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20 to 70/30) to obtain 0.20 g (yield: 85.4%) of the desired product as a white solid.

Preparation Example 4

Preparation of N-isobutyl-4-(2-(4-fluoro-3-phenylphenoxy)ethyl)benzamide (Compound No. 4-6)

(1) 0.21 g (1.73 mmol) of phenylboronic acid, 0.48 g (3.46 mmol) of potassium carbonate and 0.18 g (0.16 mmol) of tetrakis(triphenylphosphine) palladium(0) were added to a solution having 0.30 g (1.57 mmol) of 3-bromo-4-fluorophenol dissolved in 2.8 ml of 1,4-dioxane and 0.7 ml of water, followed by stirring at 110° C. for 4 hours. A saturated aqueous ammonium chloride solution was added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=90/10 to 80/20) to obtain 0.29 g (yield: 98%) of 4-fluoro-3-phenylphenol as a pale yellow oil.
$^1$H-NMR(500 MHz, acetone-d6, δppm): 7.53(d, 2H, J=8.5Hz), 7.45(t, 2H, J=6.5Hz), 7.37(t, 2H, J=7.5Hz), 7.07-7.03(m, 1H), 6.93-6.91(m, 1H), 6.84-6.81(m, 1H)

(2) 0.14 g (0.52 mmol) of triphenylphosphine was added at room temperature to a solution having 70 mg (0.38 mmol) of 4-fluoro-3-phenylphenol obtained in the above (1) and 80 mg (0.36 mmol) of N-isobutyl-4-(2-hydroxyethyl)benzamide obtained in (2) in Preparation Example 3 dissolved in 1.5 ml of THF, followed by stirring for 10 minutes. Then, 0.25 ml (0.54 mmol) of DEAD (2.2 M toluene solution) was dropwise added, followed by stirring further for 15 hours. The solvent was distilled off under reduced pressure, and the obtained crude product was purified by silica gel column chromatography (developing solvent: heptane/ethyl acetate=75/25 to 65/35) to obtain 20 mg (yield: 14.1%) of the desired product as a white solid.

Preparation Example 5

Preparation of N-isobutyl-4-(2-(3-(2,4-dichlorophenyl)phenoxy)ethyl)benzamide (Compound No. 4-187)

50 mg (0.28 mmol) of 2,4-dichlorphenylboronic acid, 70 mg (0.53 mmol) of potassium carbonate and 20 mg (0.02 mmol) of tetrakis(triphenylphosphine)palladium(0) were added to a solution having 80 mg (0.21 mmol) of N-isobutyl-4-(2-(3-bromophenoxy)ethyl)benzamide (Compound No. 1-9) dissolved in 4.0 ml of 1,4-dioxane and 1.0 ml of water, followed by stirring in a nitrogen atmosphere at 90° C. for 12 hours. A saturated aqueous ammonium chloride solution was added, the aqueous layer was extracted three times with ethyl acetate, and the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=80/20 to 70/30) to obtain 80 mg (yield: 85%) of the desired product as a colorless oil.

Preparation Example 6

Preparation of N-isobutyl-4-(2-(4-chloro-3-(4-chlorophenyl)phenoxy)ethyl)benzamide (Compound No. 4-115)

0.13 g (0.85 mmol) of 4-chlorophenylboronic acid, 0.27 g (1.95 mmol) of potassium carbonate and 0.08 g (0.07 mmol)

of tetrakis(triphenylphosphine)palladium(0) were added in a nitrogen atmosphere to a solution having 0.30 g (0.66 mmol) of N-isobutyl-4-(2-(4-chloro-3-iodophenoxy)ethyl)benzamide (Compound No. 1-326) dissolved in 8 ml of 1,4-dioxane and 2 ml of water, followed by stirring at 90° C. for 12 hours. A saturated aqueous ammonium chloride solution was added, the aqueous layer was extracted three times with ethyl acetate, the organic layer was washed with a saturated aqueous sodium chloride solution, dried over anhydrous sodium sulfate and subjected to filtration, and the solvent was distilled off under reduced pressure. The obtained crude product was purified by silica gel column chromatography (developing solvent: heptane/ethyl acetate=70/30) to obtain 0.28 g (yield: 96.6%) of the desired product as a pale yellow oil.

Preparation Example 7

Preparation of N-isobuty-4-(2-(3-(trimethylsilyl-ethynyl)phenoxy)ethyl)benzamide (Compound No. 11-1)

0.30 g (0.80 mmol) of N-isobutyl-4-(2-(3-bromophenoxy)ethyl)benzamide (Compound No. 1-9), 0.33 ml (2.39 mmol) of trimethylsilylacetylene, 20 mg (0.080 mmol) of copper(I) iodide, 90 mg (0.080 mmol) of tetrakis(triphenylphosphine)palladium(0) and 0.67 ml (4.78 mmol) of triethylamine were dissolved in 3.2 ml of DMF, followed by stirring at 80° C. for 6 hours. The reaction solution was left to cool to room temperature, water was added to the reaction solution, and the reaction solution was extracted with ethyl acetate. The organic layer was washed with water and a saturated aqueous sodium chloride solution and dried over anhydrous sodium sulfate. Anhydrous sodium sulfate was removed by filtration, the solvent was distilled off under reduced pressure, and the residue was purified by flush chromatography (eluent: n-heptane/ethyl acetate=80/20 to 70/30) to obtain 0.27 g (yield: 86.0%) of the desired product as a yellow solid.

Then, among the Invention Compounds represented by the above formula (I), representative examples of the compound represented by the above formula (I-1) are shown in Table 1, representative examples of the compound represented by the formula above (I-2) are shown in Table 2, representative examples of the compound represented by the above formula (I-3) are shown in Tables 3 and 4, representative examples of the compound represented by the above formula (I-4) are shown in Tables 5 to 9, and representative examples of the compound represented by the above formula (I-5) are shown in Tables 10 to 12.

In Tables 1 to 12, the numerical value shown as physical properties is the melting point (° C.). A compound represented as "Oil" is an oil, the compound represented as "Solid" is a solid, and a compound represented as "Gum" is a rubber-like substance. These compounds may be prepared in accordance with the above Preparation Example or the above process for the Invention Compound. In Tables 1 to 12, Me represents methyl, Et ethyl, n-Pr n-propyl, i-Pr isopropyl, n-Bu n-butyl, i-Bu isobutyl, t-Bu tert-butyl, and s-Bu sec-butyl. The substitution positions of $R^3$ and $R^4$ on the benzene ring are in accordance with the numbers in the chemical structural formulae in Tables. The compound represented as "-" in the columns for $R^4$, $R^7$ and $R^9$ means that the compound is not substituted by each substituent. Further, the moiety represented by "● (black solid circle)" in $R^1$ means that $R^1$ is bonded to the nitrogen atom at said moiety. p in Tables is the number of $R^4$, and q, r and s are the number of $R^9$. In a case where $R^1$ and $R^2$ form, together with the adjacent nitrogen atom, a cyclic structure which may be substituted by Z, the moiety where the cyclic structure is bonded to the carbonyl group is represented by a wavy line as follows:

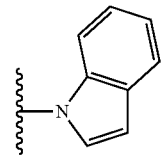 [SMILES: *n1ccc2ccccc21]

Further, in a case where $R^4$ is a phenoxy group on the 3-position of the phenyl ring, it may sometimes be represented as:

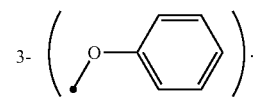

TABLE 1

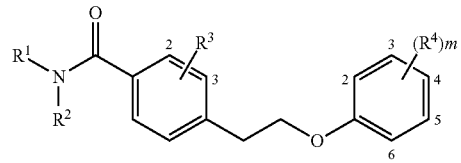

| No. | $R^1$ | $R^2$ | $R^3$ | $R^4$ | m | PP |
|---|---|---|---|---|---|---|
| 1-1 | i-Bu | H | H | — | 0 | 84.2 |
| 1-2 | i-Bu | H | H | 2-F | 1 | 56.5 |
| 1-3 | i-Bu | H | H | 3-F | 1 | 88.0 |
| 1-4 | i-Bu | H | H | 4-F | 1 | 96.9 |
| 1-5 | i-Bu | H | H | 2-Cl | 1 | Oil |
| 1-6 | i-Bu | H | H | 3-Cl | 1 | Oil |
| 1-7 | i-Bu | H | H | 4-Cl | 1 | 71.3 |
| 1-8 | i-Bu | H | H | 2-Br | 1 | Solid |
| 1-9 | i-Bu | H | H | 3-Br | 1 | 76.5 |
| 1-10 | i-Bu | H | H | 4-Br | 1 | 98.7 |

TABLE 1-continued

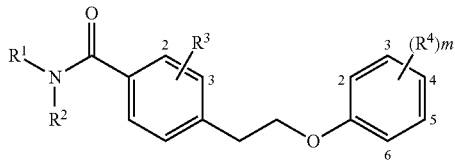

(I-1)

| No. | R¹ | R² | R³ | R⁴ | m | PP |
|---|---|---|---|---|---|---|
| 1-11 | i-Bu | H | H | 2-Me | 1 | |
| 1-12 | i-Bu | H | H | 3-Me | 1 | Solid |
| 1-13 | i-Bu | H | H | 4-Me | 1 | 89.5 |
| 1-14 | i-Bu | H | H | 2-Et | 1 | |
| 1-15 | i-Bu | H | H | 3-Et | 1 | 188.0 |
| 1-16 | i-Bu | H | H | 4-Et | 1 | |
| 1-17 | i-Bu | H | H | 2-CF₃ | 1 | Oil |
| 1-18 | i-Bu | H | H | 3-CF₃ | 1 | Oil |
| 1-19 | i-Bu | H | H | 4-CF₃ | 1 | 108.0 |
| 1-20 | i-Bu | H | H | 2-OMe | 1 | |
| 1-21 | i-Bu | H | H | 3-OMe | 1 | Oil |
| 1-22 | i-Bu | H | H | 4-OMe | 1 | |
| 1-23 | i-Bu | H | H | 2-OCF₃ | 1 | Oil |
| 1-24 | i-Bu | H | H | 3-OCF₃ | 1 | 65.2 |
| 1-25 | i-Bu | H | H | 4-OCF₃ | 1 | Solid |
| 1-26 | i-Bu | H | H | 2-COMe | 1 | |
| 1-27 | i-Bu | H | H | 3-COMe | 1 | Solid |
| 1-28 | i-Bu | H | H | 4-COMe | 1 | |
| 1-29 | i-Bu | H | H | 2-SMe | 1 | |
| 1-30 | i-Bu | H | H | 3-SMe | 1 | Oil |
| 1-31 | i-Bu | H | H | 4-SMe | 1 | |
| 1-32 | i-Bu | H | H | 2-SCF₃ | 1 | |
| 1-33 | i-Bu | H | H | 3-SCF₃ | 1 | |
| 1-34 | i-Bu | H | H | 4-SCF₃ | 1 | |
| 1-35 | i-Bu | H | H | 2-SOMe | 1 | |
| 1-36 | i-Bu | H | H | 3-SOMe | 1 | Oil |
| 1-37 | i-Bu | H | H | 4-SOMe | 1 | |
| 1-38 | i-Bu | H | H | 2-SOCF₃ | 1 | |
| 1-39 | i-Bu | H | H | 3-SOCF₃ | 1 | |
| 1-40 | i-Bu | H | H | 4-SOCF₃ | 1 | |
| 1-41 | i-Bu | H | H | 2-SO₂Me | 1 | |
| 1-42 | i-Bu | H | H | 3-SO₂Me | 1 | 117.0 |
| 1-43 | i-Bu | H | H | 4-SO₂Me | 1 | |
| 1-44 | i-Bu | H | H | 2-SO₂CF₃ | 1 | |
| 1-45 | i-Bu | H | H | 3-SO₂CF₃ | 1 | |
| 1-46 | i-Bu | H | H | 4-SO₂CF₃ | 1 | |
| 1-47 | i-Bu | H | H | 2-CN | 1 | |
| 1-48 | i-Bu | H | H | 3-CN | 1 | 83.0 |
| 1-49 | i-Bu | H | H | 4-CN | 1 | |
| 1-50 | i-Bu | H | H | 2-NO₂ | 1 | |
| 1-51 | i-Bu | H | H | 3-NO₂ | 1 | 95.0 |
| 1-52 | i-Bu | H | H | 4-NO₂ | 1 | |
| 1-53 | i-Bu | H | H | 2-OCF₃, 3-F | 2 | |
| 1-54 | i-Bu | H | H | 2-OCF₃, 3-Cl | 2 | |
| 1-55 | i-Bu | H | H | 2-OCF₃, 3-Br | 2 | |
| 1-56 | i-Bu | H | H | 2-OCF₃, 4-F | 2 | |
| 1-57 | i-Bu | H | H | 2-OCF₃, 4-Cl | 2 | |
| 1-58 | i-Bu | H | H | 2-OCF₃, 4-Br | 2 | |
| 1-59 | i-Bu | H | H | 2-OCF₃, 5-F | 2 | |
| 1-60 | i-Bu | H | H | 2-OCF₃, 5-Cl | 2 | |
| 1-61 | i-Bu | H | H | 2-OCF₃, 5-Br | 2 | |
| 1-62 | i-Bu | H | H | 2-OCF₃, 6-F | 2 | |
| 1-63 | i-Bu | H | H | 2-OCF₃, 6-Cl | 2 | |
| 1-64 | i-Bu | H | H | 2-OCF₃, 6-Br | 2 | |
| 1-65 | i-Bu | H | H | 3-OCF₃, 2-F | 2 | |
| 1-66 | i-Bu | H | H | 3-OCF₃, 2-Cl | 2 | |
| 1-67 | i-Bu | H | H | 3-OCF₃, 2-Br | 2 | |
| 1-68 | i-Bu | H | H | 3-OCF₃, 4-F | 2 | 50.0 |
| 1-69 | i-Bu | H | H | 3-OCF₃, 4-Cl | 2 | Oil |
| 1-70 | i-Bu | H | H | 3-OCF₃, 4-Br | 2 | 79.0 |
| 1-71 | i-Bu | H | H | 3-OCF₃, 5-F | 2 | |
| 1-72 | i-Bu | H | H | 3-OCF₃, 5-Cl | 2 | Solid |
| 1-73 | i-Bu | H | H | 3-OCF₃, 5-Br | 2 | Oil |
| 1-74 | i-Bu | H | H | 3-OCF₃, 6-F | 2 | 77.9 |
| 1-75 | i-Bu | H | H | 3-OCF₃, 6-Cl | 2 | 87.9 |
| 1-76 | i-Bu | H | H | 3-OCF₃, 6-Br | 2 | 101.2 |
| 1-77 | i-Bu | H | H | 4-OCF₃, 2-F | 2 | |
| 1-78 | i-Bu | H | H | 4-OCF₃, 2-Cl | 2 | |

TABLE 1-continued (I-1)

| No. | R¹ | R² | R³ | R⁴ | m | PP |
|---|---|---|---|---|---|---|
| 1-79 | i-Bu | H | H | 4-OCF$_3$, 2-Br | 2 | |
| 1-80 | i-Bu | H | H | 4-OCF$_3$, 3-F | 2 | 101.3 |
| 1-81 | i-Bu | H | H | 4-OCF$_3$, 3-Cl | 2 | |
| 1-82 | i-Bu | H | H | 4-OCF$_3$, 3-Br | 2 | 93.2 |
| 1-83 | i-Bu | H | H | 2-CF$_3$, 3-F | 2 | |
| 1-84 | i-Bu | H | H | 2-CF$_3$, 3-Cl | 2 | |
| 1-85 | i-Bu | H | H | 2-CF$_3$, 3-Br | 2 | |
| 1-86 | i-Bu | H | H | 2-CF$_3$, 4-F | 2 | |
| 1-87 | i-Bu | H | H | 2-CF$_3$, 4-Cl | 2 | |
| 1-88 | i-Bu | H | H | 2-CF$_3$, 4-Br | 2 | 103.4 |
| 1-89 | i-Bu | H | H | 2-CF$_3$, 5-F | 2 | |
| 1-90 | i-Bu | H | H | 2-CF$_3$, 5-Cl | 2 | |
| 1-91 | i-Bu | H | H | 2-CF$_3$, 5-Br | 2 | |
| 1-92 | i-Bu | H | H | 2-CF$_3$, 6-F | 2 | |
| 1-93 | i-Bu | H | H | 2-CF$_3$, 6-Cl | 2 | |
| 1-94 | i-Bu | H | H | 2-CF$_3$, 6-Br | 2 | |
| 1-95 | i-Bu | H | H | 3-CF$_3$, 2-F | 2 | 72.2 |
| 1-96 | i-Bu | H | H | 3-CF$_3$, 2-Cl | 2 | |
| 1-97 | i-Bu | H | H | 3-CF$_3$, 2-Br | 2 | 93.2 |
| 1-98 | i-Bu | H | H | 3-CF$_3$, 4-F | 2 | 76.4 |
| 1-99 | i-Bu | H | H | 3-CF$_3$, 4-Cl | 2 | Oil |
| 1-100 | i-Bu | H | H | 3-CF$_3$, 4-Br | 2 | Oil |
| 1-101 | i-Bu | H | H | 3-CF$_3$, 5-F | 2 | Oil |
| 1-102 | i-Bu | H | H | 3-CF$_3$, 5-Cl | 2 | Oil |
| 1-103 | i-Bu | H | H | 3-CF$_3$, 5-Br | 2 | Oil |
| 1-104 | i-Bu | H | H | 3-CF$_3$, 6-F | 2 | |
| 1-105 | i-Bu | H | H | 3-CF$_3$, 6-Cl | 2 | |
| 1-106 | i-Bu | H | H | 3-CF$_3$, 6-Br | 2 | |
| 1-107 | i-Bu | H | H | 4-CF$_3$, 2-F | 2 | |
| 1-108 | i-Bu | H | H | 4-CF$_3$, 2-Cl | 2 | |
| 1-109 | i-Bu | H | H | 4-CF$_3$, 2-Br | 2 | |
| 1-110 | i-Bu | H | H | 4-CF$_3$, 3-F | 2 | |
| 1-111 | i-Bu | H | H | 4-CF$_3$, 3-Cl | 2 | |
| 1-112 | i-Bu | H | H | 4-CF$_3$, 3-Br | 2 | |
| 1-113 | i-Bu | H | 2-F | 3-OCF$_3$ | 1 | Oil |
| 1-114 | i-Bu | H | 2-Cl | 3-OCF$_3$ | 1 | |
| 1-115 | i-Bu | H | 2-Br | 3-OCF$_3$ | 1 | Solid |
| 1-116 | i-Bu | H | 2-CF$_3$ | 3-OCF$_3$ | 1 | |
| 1-117 | i-Bu | H | 2-Me | 3-OCF$_3$ | 1 | |
| 1-118 | i-Bu | H | 2-OMe | 3-OCF$_3$ | 1 | |
| 1-119 | i-Bu | H | 2-CN | 3-OCF$_3$ | 1 | |
| 1-120 | i-Bu | H | 3-F | 3-OCF$_3$ | 1 | Oil |
| 1-121 | i-Bu | H | 3-Cl | 3-OCF$_3$ | 1 | Oil |
| 1-122 | i-Bu | H | 3-Br | 3-OCF$_3$ | 1 | 66.2 |
| 1-123 | i-Bu | H | 3-CF$_3$ | 3-OCF$_3$ | 1 | |
| 1-124 | i-Bu | H | 3-Me | 3-OCF$_3$ | 1 | Oil |
| 1-125 | i-Bu | H | 3-OMe | 3-OCF$_3$ | 1 | |
| 1-126 | i-Bu | H | 3-CN | 3-OCF$_3$ | 1 | 82.2 |
| 1-127 | H | H | H | 3-OCF$_3$ | 1 | 98.5 |
| 1-128 | n-Pr | H | H | 3-OCF$_3$ | 1 | 54.0 |
| 1-129 | n-Bu | H | H | 3-OCF$_3$ | 1 | Oil |
| 1-130 | s-Bu | H | H | 3-OCF$_3$ | 1 | Oil |
| 1-131 | CH$_2$CH$_2$CH(CH$_3$)$_2$ | H | H | 3-OCF$_3$ | 1 | 42.4 |
| 1-132 | CH$_2$CH(CH$_3$)CH$_2$CH$_3$ | H | H | 3-OCF$_3$ | 1 | Oil |
| 1-133 | CH$_2$C(CH$_3$)$_3$ | H | H | 3-OCF$_3$ | 1 | Oil |
| 1-134 | CH$_2$CH$_2$CN | H | H | 3-OCF$_3$ | 1 | 88.8 |
| 1-135 | CH$_2$C(CH$_3$)$_2$CH$_2$N(CH$_3$)$_2$ | H | H | 3-OCF$_3$ | 1 | Oil |
| 1-136 | CH$_2$CH(OCH$_3$)$_2$ | H | H | 3-OCF$_3$ | 1 | Oil |
| 1-137 | CH$_2$CH$_2$CH$_2$OCH$_3$ | H | H | 3-OCF$_3$ | 1 | 79.8 |
| 1-138 | CH$_2$CH$_2$SCH$_3$ | H | H | 3-OCF$_3$ | 1 | 62.1 |
| 1-139 | CH$_2$C≡CH | H | H | 3-OCF$_3$ | 1 | 101.8 |
| 1-140 | CH$_2$CF$_3$ | H | H | 3-OCF$_3$ | 1 | 123.4 |
| 1-141 | CH$_2$OCH$_3$ | H | H | 3-OCF$_3$ | 1 | |
| 1-142 | CH$_2$C(CH$_3$)=CH$_2$ | H | H | 3-OCF$_3$ | 1 | 51.5 |
| 1-143 | CH$_2$C(CH$_3$)$_2$CH$_2$NH$_2$ | H | H | 3-OCF$_3$ | 1 | |
| 1-144 | CH$_2$C(CH$_3$)$_2$CH$_2$NHCH$_3$ | H | H | 3-OCF$_3$ | 1 | |
| 1-145 | NHCH(CH$_3$)$_2$ | H | H | 3-OCF$_3$ | 1 | Oil |
| 1-146 | NHCH$_3$ | H | H | 3-OCF$_3$ | 1 | |

TABLE 1-continued (I-1)

| No. | R¹ | R² | R³ | R⁴ | m | PP |
|---|---|---|---|---|---|---|
| 1-147 | N(CH₃)₂ | H | H | 3-OCF₃ | 1 | |
| 1-148 | CH₂CH₂OH | H | H | 3-OCF₃ | 1 | |
| 1-149 | CH₂CH₂SH | H | H | 3-OCF₃ | 1 | |
| 1-150 | CH₂CH₂NH₂ | H | H | 3-OCF₃ | 1 | |
| 1-151 | CH₂-cyclopropyl | H | H | 3-OCF₃ | 1 | 98.0 |
| 1-152 | CH₂-(tetrahydropyran-4-yl, O) | H | H | 3-OCF₃ | 1 | Oil |
| 1-153 | CH₂-(tetrahydrothiopyran-4-yl, S) | H | H | 3-OCF₃ | 1 | 100.6 |
| 1-154 | CH₂-(N-methylpiperidin-4-yl) | H | H | 3-OCF₃ | 1 | Oil |
| 1-155 | CH₂C₆H₅ | H | H | 3-OCF₃ | 1 | 96.7 |
| 1-156 | i-Bu | Me | H | 3-OCF₃ | 1 | Oil |
| 1-157 | i-Bu | COMe | H | 3-OCF₃ | 1 | |
| 1-158 | i-Bu | Me | H | 4-CF₃ | 1 | |
| 1-159 | i-Bu | COMe | H | 4-CF₃ | 1 | |
| 1-160 | CH(CH₃)-cyclohexyl | H | H | 3-OCF₃ | 1 | 95.9 |
| 1-161 | CH(CH₃)-cyclopropyl | H | H | 3-OCF₃ | 1 | Oil |
| 1-162 | CH(CH₃)CH₂CH₂CH₃ | H | H | 3-OCF₃ | 1 | Oil |
| 1-163 | CH(CH₃)CH₂CH(CH₃)₂ | H | H | 3-OCF₃ | 1 | Oil |
| 1-164 | i-Pr | H | H | 3-OCF₃ | 1 | Oil |
| 1-165 | CH(CH₃)CH(CH₃)₂ | H | H | 3-OCF₃ | 1 | 88.2 |
| 1-166 | CH(CH₃)CH₂CH₂CH₃ | H | H | 3-OCF₃ | 1 | Oil |
| 1-167 | t-Bu | H | H | 3-OCF₃ | 1 | Oil |
| 1-168 | CH(CH₃)C₆H₅ | H | H | 3-OCF₃ | 1 | 105.7 |
| 1-169 | CH(CH₂CH₃)CH₂CH₃ | H | H | 3-OCF₃ | 1 | |
| 1-170 | C(CH₃)₂CH₂CH₃ | H | H | 3-OCF₃ | 1 | Oil |
| 1-171 | CH₂-cyclohexyl | H | H | 3-OCF₃ | 1 | 62.0 |
| 1-172 | CH₂-(tetrahydrofuran-2-yl) | H | H | 3-OCF₃ | 1 | 83.1 |
| 1-173 | CH₂-(N-ethylpyrrolidin-2-yl) | H | H | 3-OCF₃ | 1 | Oil |

TABLE 1-continued

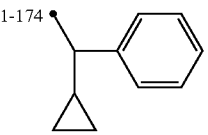

(I-1)

| No. | R¹ | R² | R³ | R⁴ | m | PP |
|---|---|---|---|---|---|---|
| 1-174 | 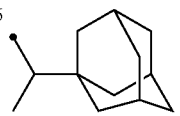 | H | H | 3-OCF₃ | 1 | Oil |
| 1-175 | C(CH₃)₂CH₂C(CH₃)₃ | H | H | 3-OCF₃ | 1 | Oil |
| 1-176 | 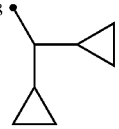 | H | H | 3-OCF₃ | 1 | Oil |
| 1-177 | CH(CH₃)C(CH₃)₃ | H | H | 3-OCF₃ | 1 | Oil |
| 1-178 | 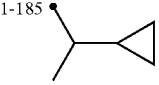 | H | H | 3-OCF₃ | 1 | 92.6 |
| 1-179 | i-Bu | H | H | 2-OCF₂H | 1 | |
| 1-180 | i-Bu | H | H | 3-OCF₂H | 1 | Oil |
| 1-181 | i-Bu | H | H | 4-OCF₂H | 1 | |
| 1-182 | i-Bu | H | H | 3-CF₃, 5-CF₃ | 2 | Oil |
| 1-183 | i-Bu | H | 3-NH₂ | 3-OCF₃ | 1 | 96.0 |
| 1-184 | i-Bu | H | 3-NO₂ | 3-OCF₃ | 1 | 93.0 |
| 1-185 | 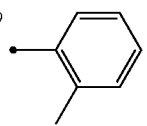 | H | H | 3-OCF₃, 4-Br | 2 | 85.4 |
| 1-186 | CH(CH₃)CH(CH₃)₂ | H | H | 3-OCF₃, 4-Br | 2 | 122.3 |
| 1-187 | i-Bu | H | H | 2-Br, 4-Br | 2 | 100.4 |
| 1-188 | i-Bu | H | H | 4-Br, 2-F | 2 | 81.1 |
| 1-189 | i-Bu | H | H | 4-Br, 2-Cl | 2 | 107.3 |
| 1-190 | i-Bu | H | H | 3-F, 5-F | 2 | 90.5 |
| 1-191 | i-Bu | H | H | 4-Cl, 2-F | 2 | 67.6 |
| 1-192 | i-Bu | H | H | 2-Br, 4-Cl | 2 | 65.7 |
| 1-193 | i-Bu | H | H | 3-Br, 5-F | 2 | 88.5 |
| 1-194 | i-Bu | H | H | 2-Cl, 4-Cl | 2 | 88.6 |
| 1-195 | i-Bu | H | H | 2-F, 3-F | 2 | 76.1 |
| 1-196 | i-Bu | H | H | 3-Br, 2-F | 2 | 102.5 |
| 1-197 | i-Bu | H | H | 5-Br, 2-F | 2 | 100.0 |
| 1-198 | i-Bu | H | H | 3-Br, 5-Br | 2 | 115.9 |
| 1-199 | i-Bu | H | H | 5-Br, 2-Cl | 2 | 85.0 |
| 1-200 | i-Bu | H | H | 4-Cl, 3-F | 2 | 86.3 |
| 1-201 | i-Bu | H | H | 3-Cl, 4-Cl | 2 | 84.9 |
| 1-202 | i-Bu | H | H | 3-F, 4-F | 2 | 93.3 |
| 1-203 | i-Bu | H | H | 4-Br, 3-Cl | 2 | 82.7 |
| 1-204 | i-Bu | H | H | 2-F, 4-F | 2 | 47.8 |
| 1-205 | i-Bu | H | H | 4-Br, 3-F | 2 | 74.3 |
| 1-206 | i-Bu | H | H | 3-F, 4-Me | 2 | 125.9 |
| 1-207 | i-Bu | H | H | 3-F, 4-COCH₃ | 2 | 115.2 |
| 1-208 | i-Bu | H | H | 3-F, 4-F, 5-F | 3 | 107.7 |
| 1-209 |  | H | H | 3-OCF₃, 4-Br | 2 | 101.2 |

TABLE 1-continued (I-1)

| No. | R¹ | R² | R³ | R⁴ | m | PP |
|---|---|---|---|---|---|---|
| 1-210 | t-Bu | H | H | 3-OCF₃, 4-Br | 2 | 87.0 |
| 1-211 | CH₂CH(CH₃)CH₂CH₃ | H | H | 3-OCF₃, 4-Br | 2 | 91.9 |
| 1-212 | CH₂C(CH₃)₃ | H | H | 3-OCF₃, 4-Br | 2 | 137.3 |
| 1-213 | s-Bu | H | H | 3-OCF₃, 4-Br | 2 | 80.7 |
| 1-214 | CH(CH₃)C(CH₃)₃ | H | H | 3-OCF₃, 4-Br | 2 | Oil |
| 1-215 | cyclobutylmethyl | H | H | 3-OCF₃ | 1 | 64.5 |
| 1-216 | cyclopropyl | H | H | 3-OCF₃ | 1 | 79.4 |
| 1-217 | cyclohexyl | H | H | 3-OCF₃ | 1 | 110.2 |
| 1-218 | indanyl | H | H | 3-OCF₃ | 1 | Oil |
| 1-219 | cycloheptyl | H | H | 3-OCF₃ | 1 | 104.1 |
| 1-220 | 2-methylcyclohexyl | H | H | 3-OCF₃ | 1 | 129.5 |
| 1-221 | quinuclidinyl | H | H | 3-OCF₃ | 1 | Oil |
| 1-222 | 2-methylphenyl | H | H | 3-OCF₃ | 1 | 94.4 |
| 1-223 | 3-methylphenyl | H | H | 3-OCF₃ | 1 | 63.1 |
| 1-224 | 4-methylphenyl | H | H | 3-OCF₃ | 1 | 99.7 |
| 1-225 | 4-fluorophenyl | H | H | 3-OCF₃ | 1 | 111.0 |

TABLE 1-continued (I-1)

| No. | R¹ | R² | R³ | R⁴ | m | PP |
|---|---|---|---|---|---|---|
| 1-226 | cyclopentyl | H | H | 3-OCF₃ | 1 | 62.1 |
| 1-227 | 2-ethylphenyl | H | H | 3-OCF₃ | 1 | 63.4 |
| 1-228 | 2-isopropylphenyl | H | H | 3-OCF₃ | 1 | 79.3 |
| 1-229 | 2-(trifluoromethyl)phenyl | H | H | 3-OCF₃ | 1 | 74.7 |
| 1-230 | 2-bromophenyl | H | H | 3-OCF₃ | 1 | 78.7 |
| 1-231 | 2-methoxyphenyl | H | H | 3-OCF₃ | 1 | Oil |
| 1-232 | 3-(trifluoromethyl)pyridin-2-yl | H | H | 3-OCF₃ | 1 | 61.3 |
| 1-233 | 2-chlorophenyl | H | H | 3-OCF₃ | 1 | Oil |
| 1-234 | phenyl | H | H | 3-OCF₃ | 1 | 99.4 |

TABLE 1-continued (I-1)

| No. | R¹ | R² | R³ | R⁴ | m | PP |
|---|---|---|---|---|---|---|
| 1-235 | 2-fluorophenyl | H | H | 3-OCF₃ | 1 | 80.4 |
| 1-236 | 2-nitrophenyl | H | H | 3-OCF₃ | 1 | 91.1 |
| 1-237 | 2,3-dimethylphenyl | H | H | 3-OCF₃ | 1 | 110.5 |
| 1-238 | 2,5-dimethylphenyl | H | H | 3-OCF₃ | 1 | 140.8 |
| 1-239 | 2,4-dimethylphenyl | H | H | 3-OCF₃ | 1 | 94.1 |
| 1-240 | 2,3-dimethylphenyl | H | H | 3-OCF₃ | 1 | 66.3 |
| 1-241 | 1-methyl-1H-pyrazol-5-yl | H | H | 3-OCF₃ | 1 | Oil |
| 1-242 | 3-methylpyridin-2-yl | H | H | 3-OCF₃ | 1 | Oil |
| 1-243 | 5-methylpyridin-3-yl | H | H | 3-OCF₃ | 1 | 95.0 |

TABLE 1-continued (I-1)

[Structure: R¹R²N-C(=O)-phenyl(R³)-CH₂CH₂-O-phenyl(R⁴)ₘ]

| No. | R¹ | R² | R³ | R⁴ | m | PP |
|---|---|---|---|---|---|---|
| 1-244 | 4-pyridyl, 3-methyl | H | H | 3-OCF₃ | 1 | |
| 1-245 | 3-pyridyl, 2-methyl | H | H | 3-OCF₃ | 1 | Oil |
| 1-246 | i-Bu | H | H | 2-Br, 3-F | 2 | 127.6 |
| 1-247 | i-Bu | H | H | 2-Br, 5-F | 2 | 97.2 |
| 1-248 | i-Bu | H | H | 5-Cl, 3-F | 2 | 81.3 |
| 1-249 | i-Bu | H | H | 3-Br, 4-Br | 2 | Oil |
| 1-250 | i-Bu | H | H | 3-Br, 4-F | 2 | 69.7 |
| 1-251 | i-Bu | H | H | 3-Br, 4-Cl | 2 | 83.6 |
| 1-252 | i-Bu | H | H | 3-Br, 5-Cl | 2 | 103.4 |
| 1-253 | i-Bu | H | H | 3-N(CH₃)₂ | 1 | 106.0 |
| 1-254 | i-Bu | H | H | 2-N(CH₃)₂ | 1 | |
| 1-255 | i-Bu | H | H | 4-N(CH₃)₂ | 1 | |
| 1-256 | i-Bu | H | H | 3-Cl, 4-OCF₃ | 2 | 106.1 |
| 1-257 | i-Bu | H | H | 3-F, 4-Br, 5-F | 3 | 121.2 |
| 1-258 | i-Bu | H | H | 4-I | 1 | 108.9 |
| 1-259 | i-Bu | H | H | 2-Me, 4-Br | 2 | 101.6 |
| 1-260 | i-Bu | H | H | 3-Me, 4-Br | 2 | 69.5 |
| 1-261 | CH(CH₃)CH(CH₃)₂ | H | H | 3-CF₃, 4-Br | 2 | Oil |
| 1-262 | 2-methylphenyl | H | H | 3-CF₃, 4-Br | 2 | Oil |
| 1-263 | CH(CH₃)CH(CH₃)₂ | H | H | 3-OCF₃, 4-F | 2 | Oil |
| 1-264 | 2-methylphenyl | H | H | 3-OCF₃, 4-F | 2 | 74.1 |
| 1-265 | CH(CH₃)CH(CH₃)₂ | H | H | 4-Br | 1 | 87.1 |
| 1-266 | 2-methylphenyl | H | H | 4-Br | 1 | 135.1 |
| 1-267 | i-Bu | H | H | 2-F, 3-F, 4-Br | 3 | 112.4 |
| 1-268 | i-Bu | H | H | 3-F, 4-Br, 6-F | 3 | Oil |
| 1-269 | i-Bu | H | H | 3-t-Bu | 1 | Oil |
| 1-270 | i-Bu | H | H | 3-i-Pr | 1 | 46.3 |
| 1-271 | i-Bu | H | H | 3-NH₂ | 1 | Oil |
| 1-272 | CH₂C(CH₃)₃ | H | H | 3-CF₃, 4-Br | 2 | 140.2 |
| 1-273 | CH₂C(CH₃)₃ | H | H | 3-OCF₃, 4-F | 2 | 73.3 |
| 1-274 | CH₂C(CH₃)₃ | H | H | 4-Br | 1 | 94.4 |
| 1-275 | CH₂CH(CH₃)CH₂CH₃ | H | H | 3-CF₃, 4-Br | 2 | 91.7 |
| 1-276 | CH₂CH(CH₃)CH₂CH₃ | H | H | 3-OCF₃, 4-F | 2 | Oil |
| 1-277 | CH₂CH(CH₃)CH₂CH₃ | H | H | 4-Br | 1 | Oil |
| 1-278 | i-Bu | H | H | 3-CN, 4-Br | 2 | Oil |
| 1-279 | CH(CH₃)CH(CH₃)₂ | H | 2-F | 3-OCF₃ | 1 | Oil |

TABLE 1-continued
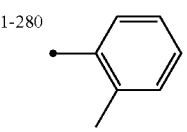
(I-1)
| No. | R¹ | R² | R³ | R⁴ | m | PP |
|---|---|---|---|---|---|---|
| 1-280 | 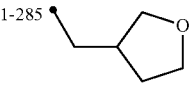 | H | 2-F | 3-OCF₃ | 1 | 57.8 |
| 1-281 | i-Bu | COMe | H | 3-OCF₃ | 1 | Oil |
| 1-282 | Me | COMe | H | 3-OCF₃ | 1 | Oil |
| 1-283 | H | CO-i-Pr | H | 3-OCF₃ | 1 | 72.4 |
| 1-284 | H | COMe | H | 3-OCF₃ | 1 | 93.8 |
| 1-285 | 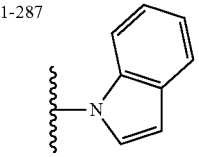 | H | H | 3-OCF₃ | 1 | Oil |
| 1-286 | i-Bu | | H | H | 3-SF₅ | 1 | Gum |
| 1-287 | 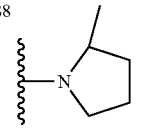 | | H | 3-OCF₃ | 1 | Oil |
| 1-288 | 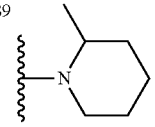 | | H | 3-OCF₃ | 1 | Oil |
| 1-289 | 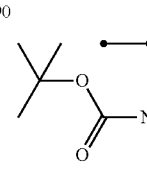 | | H | 3-OCF₃ | 1 | Oil |
| 1-290 | 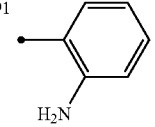 | H | H | 3-OCF₃ | 1 | Gum |
| 1-291 | 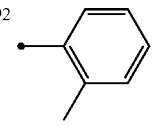 | H | H | 3-OCF₃ | 1 | Oil |
| 1-292 | 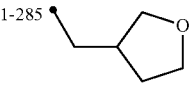 | Me | H | 3-OCF₃ | 1 | Oil |
| 1-293 | CH(CH₃)COCH₃ | H | H | 3-OCF₃ | 1 | Oil |

TABLE 1-continued (I-1)

R¹R²N-C(=O)-[benzene(2,3-R³)]-CH₂CH₂-O-[benzene(2,3,4,5,6)-(R⁴)m]

| No. | R¹ | R² | R³ | R⁴ | m | PP |
|---|---|---|---|---|---|---|
| 1-294 | methylcyclopropyl | H | H | 3-OCF₃ | 1 | 67.0 |
| 1-295 | 2,2-dimethylcyclopropyl | H | H | 3-OCF₃ | 1 | 85.6 |
| 1-296 | oxetanyl | H | H | 3-OCF₃ | 1 | Oil |
| 1-297 | 2-methylphenyl | COMe | H | 3-OCF₃ | 1 | Oil |
| 1-298 | 4-methylthien-3-yl | H | H | 3-OCF₃ | 1 | 88.5 |
| 1-299 | i-Bu | H | 3-COMe | 3-OCF₃ | 1 | |
| 1-300 | i-Bu | H | 3-CO₂Me | 3-OCF₃ | 1 | |
| 1-301 | i-Bu | H | 3-NHMe | 3-OCF₃ | 1 | |
| 1-302 | i-Bu | H | 3-N(Me)₂ | 3-OCF₃ | 1 | |
| 1-303 | i-Bu | H | H | 2-CO₂Me | 1 | |
| 1-304 | i-Bu | H | H | 3-CO₂Me | 1 | |
| 1-305 | i-Bu | H | H | 4-CO₂Me | 1 | |
| 1-306 | i-Bu | H | H | 2-CF(CF₃)₂ | 1 | |
| 1-307 | i-Bu | H | H | 3-CF(CF₃)₂ | 1 | |
| 1-308 | i-Bu | H | H | 4-CF(CF₃)₂ | 1 | |
| 1-309 | i-Bu | H | H | 3-(CH=CH₂) | 1 | |
| 1-310 | i-Bu | H | H | 3-(CH=CHCH₃) | 1 | Solid |
| 1-311 | i-Bu | H | H | 3-(CH=CHCH₃, cis) | 1 | |
| 1-312 | i-Bu | H | H | 3-(CH=CHCH₂CH₃) | 1 | |
| 1-313 | i-Bu | H | H | 3-(CH=CHCH₂CH₂CH₃) | 1 | |
| 1-314 | i-Bu | H | H | 3-(CH=C(CH₃)₂) | 1 | |
| 1-315 | i-Bu | H | H | 3-(CH=CHC(CH₃)₃) | 1 | |

TABLE 1-continued
(I-1)
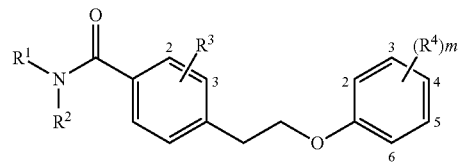
| No. | R¹ | R² | R³ | R⁴ | m | PP |
|---|---|---|---|---|---|---|
| 1-316 | i-Bu | H | H | 3-(•-O-C₆H₅) (phenoxy) | 1 | Oil |
| 1-317 | i-Bu | H | H | 3-(•-O-C₆H₄-2-F) | 1 | |
| 1-318 | i-Bu | H | H | 3-(•-O-C₆H₄-3-F) | 1 | |
| 1-319 | i-Bu | H | H | 3-(•-O-C₆H₄-4-F) | 1 | |
| 1-320 | i-Bu | H | H | 3-(•-O-C₆H₄-2-Cl) | 1 | |
| 1-321 | i-Bu | H | H | 3-(•-O-C₆H₄-3-Cl) | 1 | |
| 1-322 | i-Bu | H | H | 3-(•-O-C₆H₄-4-Cl) | 1 | |
| 1-323 | i-Bu | H | H | 2-I | 1 | |
| 1-324 | i-Bu | H | H | 3-I | 1 | 77.6 |
| 1-325 | i-Bu | H | H | 4-F, 3-I | 2 | |
| 1-326 | i-Bu | H | H | 4-Cl, 3-I | 2 | Oil |
| 1-327 | i-Bu | H | H | 4-Br, 3-I | 2 | Oil |
| 1-328 | i-Bu | H | H | 3-CF(CF₃)₂, 4-F | 2 | |
| 1-329 | i-Bu | H | H | 3-CF(CF₃)₂, 4-Cl | 2 | |
| 1-330 | i-Bu | H | H | 3-CF(CF₃)₂, 4-Br | 2 | |
| 1-331 | CH(CH₃)CH(CH₃)₂ | H | H | 3-CF(CF₃)₂, 4-F | 2 | |
| 1-332 | 2-methylphenyl | H | H | 3-CF(CF₃)₂, 4-F | 2 | |
| 1-333 | CH(CH₃)CH(CH₃)₂ | H | H | 3-CF(CF₃)₂, 4-Cl | 2 | |

TABLE 1-continued

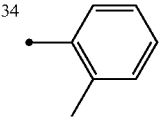
(I-1)

| No. | R¹ | R² | R³ | R⁴ | m | PP |
|---|---|---|---|---|---|---|
| 1-334 | o-tolyl | H | H | 3-CF(CF₃)₂, 4-Cl | 2 | |
| 1-335 | CH(CH₃)CH(CH₃)₂ | H | H | 3-CF(CF₃)₂, 4-Br | 2 | |
| 1-336 | o-tolyl | H | H | 3-CF(CF₃)₂, 4-Br | 2 | |

PP: Physical properties

TABLE 2

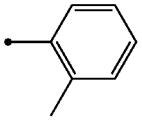
(I-2)

| No. | R¹ | R² | R³ | R⁵ | R⁶ | $(R^7)_q$ | PP |
|---|---|---|---|---|---|---|---|
| 2-1 | i-Bu | H | H | F | F | — | 90.4 |
| 2-2 | CH(CH₃)CH(CH₃)₂ | H | H | F | F | — | 93.5 |
| 2-3 | CH₂C(CH₃)₃ | H | H | F | F | — | 82.6 |
| 2-4 | o-tolyl | H | H | F | F | — | 121.8 |
| 2-5 | i-Bu | H | H | H | H | — | 112.7 |
| 2-6 | CH(CH₃)CH(CH₃)₂ | H | H | H | H | — | 116.0 |
| 2-7 | i-Bu | H | H | Cl | Cl | — | |
| 2-8 | CH(CH₃)CH(CH₃)₂ | H | H | Cl | Cl | — | |
| 2-9 | CH₂C(CH₃)₃ | H | H | Cl | Cl | — | |
| 2-10 | o-tolyl | H | H | Cl | Cl | — | |
| 2-11 | i-Bu | H | H | Me | Me | — | |
| 2-12 | CH(CH₃)CH(CH₃)₂ | H | H | Me | Me | — | |
| 2-13 | CH₂C(CH₃)₃ | H | H | Me | Me | — | |
| 2-14 | o-tolyl | H | H | Me | Me | — | |

TABLE 2-continued

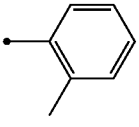
(I-2)

| No. | R¹ | R² | R³ | R⁵ | R⁶ | $(R^7)_q$ | PP |
|---|---|---|---|---|---|---|---|
| 2-15 | i-Bu | H | H | F | F | 5-F | |
| 2-16 | i-Bu | H | H | F | F | 5-Cl | |
| 2-17 | i-Bu | H | H | F | F | 5-Br | |
| 2-18 | i-Bu | H | H | F | F | 5-Me | |
| 2-19 | CH₂C(CH₃)₃ | H | H | F | F | 5-F | |
| 2-20 | CH₂C(CH₃)₃ | H | H | F | F | 5-Cl | |
| 2-21 | CH₂C(CH₃)₃ | H | H | F | F | 5-Br | |
| 2-22 | CH₂C(CH₃)₃ | H | H | F | F | 5-Me | |

PP: Physical properties

TABLE 3

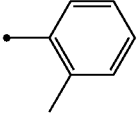
(I-3a)

| No. | R¹ | R² | R³ | $(R^4)_p$ | $(R^9)_q$ | PP |
|---|---|---|---|---|---|---|
| 3-1 | i-Bu | H | H | — | — | 128.7 |
| 3-2 | i-Bu | H | H | — | 2-F | |
| 3-3 | i-Bu | H | H | — | 3-F | |

TABLE 3-continued (I-3a)

[Structure: R¹R²N-C(=O)-phenyl(R³)-CH₂CH₂-O-phenyl(R⁴)ₚ-phenyl(R⁹)q biaryl ether with 2-substitution]

| No. | R¹ | R² | R³ | (R⁴)ₚ | (R⁹)q | PP |
|---|---|---|---|---|---|---|
| 3-4 | i-Bu | H | H | — | 4-F | |
| 3-5 | i-Bu | H | H | — | 2-Cl | |
| 3-6 | i-Bu | H | H | — | 3-Cl | |
| 3-7 | i-Bu | H | H | — | 4-Cl | |
| 3-8 | i-Bu | H | H | — | 2-F, 3-F | |
| 3-9 | i-Bu | H | H | — | 2-F, 4-F | |
| 3-10 | i-Bu | H | H | — | 2-F, 5-F | |
| 3-11 | i-Bu | H | H | — | 2-F, 6-F | |
| 3-12 | i-Bu | H | H | — | 3-F, 4-F | |
| 3-13 | i-Bu | H | H | — | 3-F, 5-F | |
| 3-14 | CH(CH₃)CH(CH₃)₂ | H | H | — | — | |
| 3-15 | o-tolyl (CH₂-2-methylphenyl) | H | H | — | — | |
| 3-16 | i-Bu | H | H | 3-F | — | |
| 3-17 | i-Bu | H | H | 3-Cl | — | |
| 3-18 | i-Bu | H | H | 3-Br | — | |
| 3-19 | i-Bu | H | H | 3-I | — | |
| 3-20 | i-Bu | H | H | 3-CF₃ | — | |
| 3-21 | i-Bu | H | H | 3-OCF₃ | — | |
| 3-22 | i-Bu | H | H | 4-F | — | |
| 3-23 | i-Bu | H | H | 4-Cl | — | |
| 3-24 | i-Bu | H | H | 4-Br | — | |
| 3-25 | i-Bu | H | H | 4-I | — | |
| 3-26 | i-Bu | H | H | 4-CF₃ | — | |
| 3-27 | i-Bu | H | H | 4-OCF₃ | — | |

PP: Physical properties

TABLE 4

(I-3b)

[Structure: R¹R²N-C(=O)-phenyl(R³)-CH₂CH₂-O-phenyl(R⁴)ₚ-phenyl(R⁹)q biaryl ether with 3-substitution]

| No. | R¹ | R² | R³ | (R⁴)ₚ | (R⁹)q | PP |
|---|---|---|---|---|---|---|
| 4-1 | i-Bu | H | H | — | — | 99.3 |
| 4-2 | CH(CH₃)CH(CH₃)₂ | H | H | — | — | |
| 4-3 | CH₂C(CH₃)₃ | H | H | — | — | |
| 4-4 | CH(cyclopropyl)- | H | H | — | — | |
| 4-5 | 2-methylphenyl-CH- | H | H | — | — | |
| 4-6 | i-Bu | H | H | 4-F | — | 98.1 |
| 4-7 | i-Bu | H | H | 4-Cl | — | Solid |
| 4-8 | i-Bu | H | H | 4-Br | — | Oil |
| 4-9 | i-Bu | H | H | 5-F | — | |
| 4-10 | i-Bu | H | H | 5-Cl | — | 116.2 |
| 4-11 | i-Bu | H | H | 5-Br | — | |
| 4-12 | CH(CH₃)CH(CH₃)₂ | H | H | 4-F | — | |
| 4-13 | 2-methylphenyl-CH- | H | H | 4-F | — | |
| 4-14 | CH(CH₃)CH(CH₃)₂ | H | H | 4-Cl | — | |
| 4-15 | 2-methylphenyl-CH- | H | H | 4-Cl | — | |
| 4-16 | CH(CH₃)CH(CH₃)₂ | H | H | 4-Br | — | |
| 4-17 | 2-methylphenyl-CH- | H | H | 4-Br | — | |
| 4-18 | i-Bu | H | H | — | 2-F | Oil |
| 4-19 | i-Bu | H | H | — | 3-F | Solid |
| 4-20 | i-Bu | H | H | — | 4-F | Solid |
| 4-21 | i-Bu | H | H | — | 2-Cl | Oil |
| 4-22 | i-Bu | H | H | — | 3-Cl | 118.3 |
| 4-23 | i-Bu | H | H | — | 4-Cl | 107.9 |
| 4-24 | i-Bu | H | H | — | 2-Br | |
| 4-25 | i-Bu | H | H | — | 3-Br | 86.3 |
| 4-26 | i-Bu | H | H | — | 4-Br | 128.5 |
| 4-27 | i-Bu | H | H | — | 2-I | |
| 4-28 | i-Bu | H | H | — | 3-I | |
| 4-29 | i-Bu | H | H | — | 4-I | |
| 4-30 | i-Bu | H | H | — | 2-Me | Oil |
| 4-31 | i-Bu | H | H | — | 3-Me | Oil |
| 4-32 | i-Bu | H | H | — | 4-Me | 122.5 |
| 4-33 | i-Bu | H | H | — | 2-CF₃ | Oil |
| 4-34 | i-Bu | H | H | — | 3-CF₃ | 88.0 |
| 4-35 | i-Bu | H | H | — | 4-CF₃ | Solid |
| 4-36 | i-Bu | H | H | — | 2-OMe | Oil |
| 4-37 | i-Bu | H | H | — | 3-OMe | Oil |
| 4-38 | i-Bu | H | H | — | 4-OMe | 109.8 |
| 4-39 | i-Bu | H | H | — | 2-OCF₃ | Oil |
| 4-40 | i-Bu | H | H | — | 3-OCF₃ | 75.3 |
| 4-41 | i-Bu | H | H | — | 4-OCF₃ | 132.7 |
| 4-42 | i-Bu | H | H | — | 2-COMe | |
| 4-43 | i-Bu | H | H | — | 3-COMe | |

TABLE 4-continued

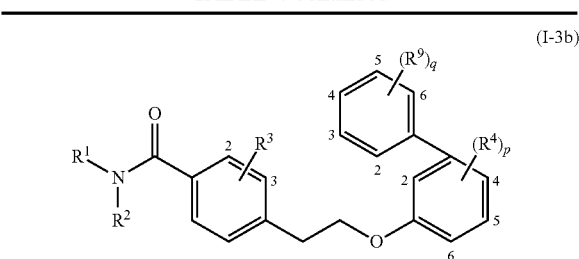
(I-3b)

| No. | R¹ | R² | R³ | (R⁴)ₚ | (R⁹)_q | PP |
|---|---|---|---|---|---|---|
| 4-44 | i-Bu | H | H | — | 4-COMe | |
| 4-45 | i-Bu | H | H | — | 2-CO₂Me | |
| 4-46 | i-Bu | H | H | — | 3-CO₂Me | |
| 4-47 | i-Bu | H | H | — | 4-CO₂Me | |
| 4-48 | i-Bu | H | H | — | 2-SMe | |
| 4-49 | i-Bu | H | H | — | 3-SMe | |
| 4-50 | i-Bu | H | H | — | 4-SMe | |
| 4-51 | i-Bu | H | H | — | 2-SCF₃ | |
| 4-52 | i-Bu | H | H | — | 3-SCF₃ | |
| 4-53 | i-Bu | H | H | — | 4-SCF₃ | |
| 4-54 | i-Bu | H | H | — | 2-SOMe | |
| 4-55 | i-Bu | H | H | — | 3-SOMe | |
| 4-56 | i-Bu | H | H | — | 4-SOMe | |
| 4-57 | i-Bu | H | H | — | 2-SOCF₃ | |
| 4-58 | i-Bu | H | H | — | 3-SOCF₃ | |
| 4-59 | i-Bu | H | H | — | 4-SOCF₃ | |
| 4-60 | i-Bu | H | H | — | 2-SO₂Me | |
| 4-61 | i-Bu | H | H | — | 3-SO₂Me | |
| 4-62 | i-Bu | H | H | — | 4-SO₂Me | |
| 4-63 | i-Bu | H | H | — | 2-SO₂CF₃ | |
| 4-64 | i-Bu | H | H | — | 3-SO₂CF₃ | |
| 4-65 | i-Bu | H | H | — | 4-SO₂CF₃ | |
| 4-66 | i-Bu | H | H | — | 2-NH₂ | |
| 4-67 | i-Bu | H | H | — | 3-NH₂ | |
| 4-68 | i-Bu | H | H | — | 4-NH₂ | |
| 4-69 | i-Bu | H | H | — | 2-NHMe | |
| 4-70 | i-Bu | H | H | — | 3-NHMe | |
| 4-71 | i-Bu | H | H | — | 4-NHMe | |
| 4-72 | i-Bu | H | H | — | 2-NMe₂ | |
| 4-73 | i-Bu | H | H | — | 3-NMe₂ | |
| 4-74 | i-Bu | H | H | — | 4-NMe₂ | |
| 4-75 | i-Bu | H | H | — | 2-CN | Oil |
| 4-76 | i-Bu | H | H | — | 3-CN | 112.2 |
| 4-77 | i-Bu | H | H | — | 4-CN | 129.3 |
| 4-78 | i-Bu | H | H | — | 2-NO₂ | |
| 4-79 | i-Bu | H | H | — | 3-NO₂ | |
| 4-80 | i-Bu | H | H | — | 4-NO₂ | |
| 4-81 | CH(CH₃)CH(CH₃)₂ | H | H | — | 2-F | |
| 4-82 | o-tolyl | H | H | — | 2-F | |
| 4-83 | CH(CH₃)CH(CH₃)₂ | H | H | — | 3-F | |
| 4-84 | o-tolyl | H | H | — | 3-F | |
| 4-85 | CH(CH₃)CH(CH₃)₂ | H | H | — | 4-F | |
| 4-86 | o-tolyl | H | H | — | 4-F | |
| 4-87 | CH(CH₃)CH(CH₃)₂ | H | H | — | 2-Cl | |
| 4-88 | o-tolyl | H | H | — | 2-Cl | |
| 4-89 | CH(CH₃)CH(CH₃)₂ | H | H | — | 3-Cl | |
| 4-90 | o-tolyl | H | H | — | 3-Cl | |
| 4-91 | CH(CH₃)CH(CH₃)₂ | H | H | — | 4-Cl | |
| 4-92 | o-tolyl | H | H | — | 4-Cl | |
| 4-93 | CH(CH₃)CH(CH₃)₂ | H | H | — | 2-Br | |
| 4-94 | o-tolyl | H | H | — | 2-Br | |
| 4-95 | CH(CH₃)CH(CH₃)₂ | H | H | — | 3-Br | |
| 4-96 | o-tolyl | H | H | — | 3-Br | |
| 4-97 | CH(CH₃)CH(CH₃)₂ | H | H | — | 4-Br | |
| 4-98 | o-tolyl | H | H | — | 4-Br | |
| 4-99 | i-Bu | H | H | 4-F | 2-F | |
| 4-100 | i-Bu | H | H | 4-Cl | 2-F | Oil |
| 4-101 | i-Bu | H | H | 4-Br | 2-F | |
| 4-102 | i-Bu | H | H | 4-F | 3-F | |
| 4-103 | i-Bu | H | H | 4-Cl | 3-F | |
| 4-104 | i-Bu | H | H | 4-Br | 3-F | |
| 4-105 | i-Bu | H | H | 4-F | 4-F | |
| 4-106 | i-Bu | H | H | 4-Cl | 4-F | Oil |
| 4-107 | i-Bu | H | H | 4-Br | 4-F | |
| 4-108 | i-Bu | H | H | 4-F | 2-Cl | |
| 4-109 | i-Bu | H | H | 4-Cl | 2-Cl | Oil |
| 4-110 | i-Bu | H | H | 4-Br | 2-Cl | |
| 4-111 | i-Bu | H | H | 4-F | 3-Cl | |
| 4-112 | i-Bu | H | H | 4-Cl | 3-Cl | |
| 4-113 | i-Bu | H | H | 4-Br | 3-Cl | |

TABLE 4-continued

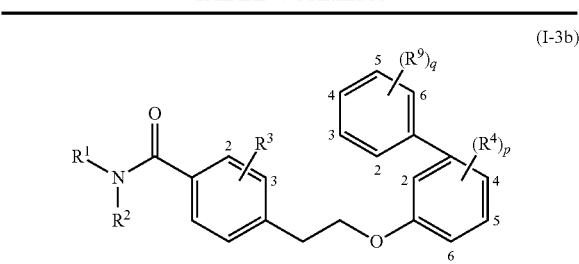
(I-3b)

| No. | R¹ | R² | R³ | (R⁴)ₚ | (R⁹)q | PP |
|---|---|---|---|---|---|---|
| 4-114 | i-Bu | H | H | 4-F | 4-Cl | |
| 4-115 | i-Bu | H | H | 4-Cl | 4-Cl | Oil |
| 4-116 | i-Bu | H | H | 4-Br | 4-Cl | |
| 4-117 | i-Bu | H | H | 4-F | 2-Br | |
| 4-118 | i-Bu | H | H | 4-Cl | 2-Br | |
| 4-119 | i-Bu | H | H | 4-Br | 2-Br | |
| 4-120 | i-Bu | H | H | 4-F | 3-Br | |
| 4-121 | i-Bu | H | H | 4-Cl | 3-Br | |
| 4-122 | i-Bu | H | H | 4-Br | 3-Br | |
| 4-123 | i-Bu | H | H | 4-F | 4-Br | |
| 4-124 | i-Bu | H | H | 4-Cl | 4-Br | |
| 4-125 | i-Bu | H | H | 4-Br | 4-Br | |
| 4-126 | CH(CH₃)CH(CH₃)₂ | H | H | 4-F | 2-F | |
| 4-127 | o-tolyl | H | H | 4-F | 2-F | |
| 4-128 | CH(CH₃)CH(CH₃)₂ | H | H | 4-Cl | 2-F | |
| 4-129 | o-tolyl | H | H | 4-Cl | 2-F | |
| 4-130 | CH(CH₃)CH(CH₃)₂ | H | H | 4-Br | 2-F | |
| 4-131 | o-tolyl | H | H | 4-Br | 2-F | |
| 4-132 | CH(CH₃)CH(CH₃)₂ | H | H | 4-F | 3-F | |
| 4-133 | o-tolyl | H | H | 4-F | 3-F | |
| 4-134 | CH(CH₃)CH(CH₃)₂ | H | H | 4-Cl | 3-F | |
| 4-135 | o-tolyl | H | H | 4-Cl | 3-F | |
| 4-136 | CH(CH₃)CH(CH₃)₂ | H | H | 4-Br | 3-F | |
| 4-137 | o-tolyl | H | H | 4-Br | 3-F | |
| 4-138 | CH(CH₃)CH(CH₃)₂ | H | H | 4-F | 4-F | |
| 4-139 | o-tolyl | H | H | 4-F | 4-F | |
| 4-140 | CH(CH₃)CH(CH₃)₂ | H | H | 4-Cl | 4-F | |
| 4-141 | o-tolyl | H | H | 4-Cl | 4-F | |
| 4-142 | CH(CH₃)CH(CH₃)₂ | H | H | 4-Br | 4-F | |
| 4-143 | o-tolyl | H | H | 4-Br | 4-F | |
| 4-144 | CH(CH₃)CH(CH₃)₂ | H | H | 4-F | 2-Cl | |
| 4-145 | o-tolyl | H | H | 4-F | 2-Cl | |
| 4-146 | CH(CH₃)CH(CH₃)₂ | H | H | 4-Cl | 2-Cl | |
| 4-147 | o-tolyl | H | H | 4-Cl | 2-Cl | |
| 4-148 | CH(CH₃)CH(CH₃)₂ | H | H | 4-Br | 2-Cl | |
| 4-149 | o-tolyl | H | H | 4-Br | 2-Cl | |
| 4-150 | CH(CH₃)CH(CH₃)₂ | H | H | 4-F | 3-Cl | |
| 4-151 | o-tolyl | H | H | 4-F | 3-Cl | |
| 4-152 | CH(CH₃)CH(CH₃)₂ | H | H | 4-Cl | 3-Cl | |

TABLE 4-continued (I-3b)

| No. | R¹ | R² | R³ | (R⁴)ₚ | (R⁹)_q | PP |
|---|---|---|---|---|---|---|
| 4-153 | 2-methylphenyl | H | H | 4-Cl | 3-Cl | |
| 4-154 | CH(CH₃)CH(CH₃)₂ | H | H | 4-Br | 3-Cl | |
| 4-155 | 2-methylphenyl | H | H | 4-Br | 3-Cl | |
| 4-156 | CH(CH₃)CH(CH₃)₂ | H | H | 4-F | 4-Cl | |
| 4-157 | 2-methylphenyl | H | H | 4-F | 4-Cl | |
| 4-158 | CH(CH₃)CH(CH₃)₂ | H | H | 4-Cl | 4-Cl | |
| 4-159 | 2-methylphenyl | H | H | 4-Cl | 4-Cl | |
| 4-160 | CH(CH₃)CH(CH₃)₂ | H | H | 4-Br | 4-Cl | |
| 4-161 | 2-methylphenyl | H | H | 4-Br | 4-Cl | |
| 4-162 | CH(CH₃)CH(CH₃)₂ | H | H | 4-F | 2-Br | |
| 4-163 | 2-methylphenyl | H | H | 4-F | 2-Br | |
| 4-164 | CH(CH₃)CH(CH₃)₂ | H | H | 4-Cl | 2-Br | |
| 4-165 | 2-methylphenyl | H | H | 4-Cl | 2-Br | |
| 4-166 | CH(CH₃)CH(CH₃)₂ | H | H | 4-Br | 2-Br | |
| 4-167 | 2-methylphenyl | H | H | 4-Br | 2-Br | |
| 4-168 | CH(CH₃)CH(CH₃)₂ | H | H | 4-F | 3-Br | |
| 4-169 | 2-methylphenyl | H | H | 4-F | 3-Br | |
| 4-170 | CH(CH₃)CH(CH₃)₂ | H | H | 4-Cl | 3-Br | |
| 4-171 | 2-methylphenyl | H | H | 4-Cl | 3-Br | |
| 4-172 | CH(CH₃)CH(CH₃)₂ | H | H | 4-Br | 3-Br | |
| 4-173 | 2-methylphenyl | H | H | 4-Br | 3-Br | |
| 4-174 | CH(CH₃)CH(CH₃)₂ | H | H | 4-F | 4-Br | |
| 4-175 | 2-methylphenyl | H | H | 4-F | 4-Br | |
| 4-176 | CH(CH₃)CH(CH₃)₂ | H | H | 4-Cl | 4-Br | |
| 4-177 | 2-methylphenyl | H | H | 4-Cl | 4-Br | |
| 4-178 | CH(CH₃)CH(CH₃)₂ | H | H | 4-Br | 4-Br | |
| 4-179 | 2-methylphenyl | H | H | 4-Br | 4-Br | |
| 4-180 | i-Bu | H | H | — | 2-F, 3-F | Oil |
| 4-181 | i-Bu | H | H | — | 2-F, 4-F | 79.4 |
| 4-182 | i-Bu | H | H | — | 2-F, 5-F | Oil |
| 4-183 | i-Bu | H | H | — | 2-F, 6-F | Oil |
| 4-184 | i-Bu | H | H | — | 3-F, 4-F | 98.6 |
| 4-185 | i-Bu | H | H | — | 3-F, 5-F | Solid |

TABLE 4-continued

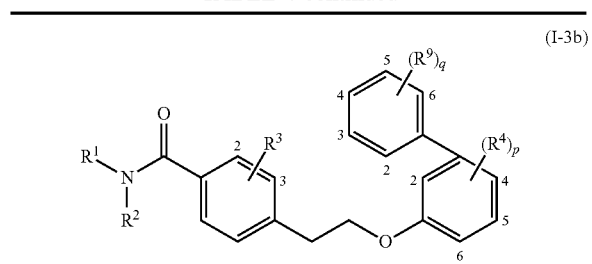

(I-3b)

| No. | R¹ | R² | R³ | $(R^4)_p$ | $(R^9)_q$ | PP |
|---|---|---|---|---|---|---|
| 4-186 | i-Bu | H | H | — | 2-Cl, 3-Cl | Oil |
| 4-187 | i-Bu | H | H | — | 2-Cl, 4-Cl | Oil |
| 4-188 | i-Bu | H | H | — | 2-Cl, 5-Cl | |
| 4-189 | i-Bu | H | H | — | 2-Cl, 6-Cl | |
| 4-190 | i-Bu | H | H | — | 3-Cl, 4-Cl | |
| 4-191 | i-Bu | H | H | — | 3-Cl, 5-Cl | Solid |
| 4-192 | i-Bu | H | H | — | 2-Br, 3-Br | |
| 4-193 | i-Bu | H | H | — | 2-Br, 4-Br | |
| 4-194 | i-Bu | H | H | — | 2-Br, 5-Br | |
| 4-195 | i-Bu | H | H | — | 2-Br, 6-Br | |
| 4-196 | i-Bu | H | H | — | 3-Br, 4-Br | |
| 4-197 | i-Bu | H | H | — | 3-Br, 5-Br | |
| 4-198 | CH(CH₃)CH(CH₃)₂ | H | H | — | 2-F, 3-F | |
| 4-199 | CH₂C(CH₃)₃ | H | H | — | 2-F, 3-F | |
| 4-200 | cyclopropylmethyl | H | H | — | 2-F, 3-F | |
| 4-201 | o-tolyl | H | H | — | 2-F, 3-F | |
| 4-202 | CH(CH₃)CH(CH₃)₂ | H | H | — | 2-F, 4-F | |
| 4-203 | CH₂C(CH₃)₃ | H | H | — | 2-F, 4-F | |
| 4-204 | cyclopropylmethyl | H | H | — | 2-F, 4-F | |
| 4-205 | o-tolyl | H | H | — | 2-F, 4-F | |
| 4-206 | CH(CH₃)CH(CH₃)₂ | H | H | — | 2-F, 5-F | |
| 4-207 | CH₂C(CH₃)₃ | H | H | — | 2-F, 5-F | |
| 4-208 | cyclopropylmethyl | H | H | — | 2-F, 5-F | |
| 4-209 | o-tolyl | H | H | — | 2-F, 5-F | |
| 4-210 | CH(CH₃)CH(CH₃)₂ | H | H | — | 2-F, 6-F | |
| 4-211 | CH₂C(CH₃)₃ | H | H | — | 2-F, 6-F | |
| 4-212 | cyclopropylmethyl | H | H | — | 2-F, 6-F | |
| 4-213 | o-tolyl | H | H | — | 2-F, 6-F | |
| 4-214 | CH(CH₃)CH(CH₃)₂ | H | H | — | 3-F, 4-F | |
| 4-215 | CH₂C(CH₃)₃ | H | H | — | 3-F, 4-F | |
| 4-216 | cyclopropylmethyl | H | H | — | 3-F, 4-F | |
| 4-217 | o-tolyl | H | H | — | 3-F, 4-F | |
| 4-218 | CH(CH₃)CH(CH₃)₂ | H | H | — | 3-F, 5-F | |
| 4-219 | CH₂C(CH₃)₃ | H | H | — | 3-F, 5-F | |
| 4-220 | cyclopropylmethyl | H | H | — | 3-F, 5-F | |
| 4-221 | o-tolyl | H | H | — | 3-F, 5-F | |
| 4-222 | i-Bu | H | H | 4-F | 2-F, 3-F | |
| 4-223 | i-Bu | H | H | 4-Cl | 2-F, 3-F | Oil |
| 4-224 | i-Bu | H | H | 4-Br | 2-F, 3-F | |
| 4-225 | i-Bu | H | H | 4-F | 2-F, 4-F | |
| 4-226 | i-Bu | H | H | 4-Cl | 2-F, 4-F | Oil |
| 4-227 | i-Bu | H | H | 4-Br | 2-F, 4-F | |
| 4-228 | i-Bu | H | H | 4-F | 2-F, 5-F | |
| 4-229 | i-Bu | H | H | 4-Cl | 2-F, 5-F | Oil |
| 4-230 | i-Bu | H | H | 4-Br | 2-F, 5-F | |
| 4-231 | i-Bu | H | H | 4-F | 2-F, 6-F | |
| 4-232 | i-Bu | H | H | 4-Cl | 2-F, 6-F | |
| 4-233 | i-Bu | H | H | 4-Br | 2-F, 6-F | |
| 4-234 | i-Bu | H | H | 4-F | 3-F, 4-F | |
| 4-235 | i-Bu | H | H | 4-Cl | 3-F, 4-F | Oil |
| 4-236 | i-Bu | H | H | 4-Br | 3-F, 4-F | |
| 4-237 | i-Bu | H | H | 4-F | 3-F, 5-F | |
| 4-238 | i-Bu | H | H | 4-Cl | 3-F, 5-F | |
| 4-239 | i-Bu | H | H | 4-Br | 3-F, 5-F | |
| 4-240 | CH(CH₃)CH(CH₃)₂ | H | H | 4-F | 2-F, 3-F | |
| 4-241 | CH₂C(CH₃)₃ | H | H | 4-F | 2-F, 3-F | |
| 4-242 | cyclopropylmethyl | H | H | 4-F | 2-F, 3-F | |

TABLE 4-continued (I-3b)

| No. | R¹ | R² | R³ | (R⁴)ₚ | (R⁹)q | PP |
|---|---|---|---|---|---|---|
| 4-243 | 2-methylphenyl | H | H | 4-F | 2-F, 3-F | |
| 4-244 | CH(CH₃)CH(CH₃)₂ | H | H | 4-Cl | 2-F, 3-F | |
| 4-245 | CH₂C(CH₃)₃ | H | H | 4-Cl | 2-F, 3-F | |
| 4-246 | 1-cyclopropylethyl | H | H | 4-Cl | 2-F, 3-F | |
| 4-247 | 2-methylphenyl | H | H | 4-Cl | 2-F, 3-F | |
| 4-248 | CH(CH₃)CH(CH₃)₂ | H | H | 4-Br | 2-F, 3-F | |
| 4-249 | CH₂C(CH₃)₃ | H | H | 4-Br | 2-F, 3-F | |
| 4-250 | 1-cyclopropylethyl | H | H | 4-Br | 2-F, 3-F | |
| 4-251 | 2-methylphenyl | H | H | 4-Br | 2-F, 3-F | |
| 4-252 | CH(CH₃)CH(CH₃)₂ | H | H | 4-F | 2-F, 4-F | |
| 4-253 | CH₂C(CH₃)₃ | H | H | 4-F | 2-F, 4-F | |
| 4-254 | 1-cyclopropylethyl | H | H | 4-F | 2-F, 4-F | |
| 4-255 | 2-methylphenyl | H | H | 4-F | 2-F, 4-F | |
| 4-256 | CH(CH₃)CH(CH₃)₂ | H | H | 4-Cl | 2-F, 4-F | |
| 4-257 | CH₂C(CH₃)₃ | H | H | 4-Cl | 2-F, 4-F | |
| 4-258 | 1-cyclopropylethyl | H | H | 4-Cl | 2-F, 4-F | |
| 4-259 | 2-methylphenyl | H | H | 4-Cl | 2-F, 4-F | |
| 4-260 | CH(CH₃)CH(CH₃)₂ | H | H | 4-Br | 2-F, 4-F | |
| 4-261 | CH₂C(CH₃)₃ | H | H | 4-Br | 2-F, 4-F | |
| 4-262 | 1-cyclopropylethyl | H | H | 4-Br | 2-F, 4-F | |
| 4-263 | 2-methylphenyl | H | H | 4-Br | 2-F, 4-F | |
| 4-264 | CH(CH₃)CH(CH₃)₂ | H | H | 4-F | 2-F, 5-F | |
| 4-265 | CH₂C(CH₃)₃ | H | H | 4-F | 2-F, 5-F | |
| 4-266 | 1-cyclopropylethyl | H | H | 4-F | 2-F, 5-F | |
| 4-267 | 2-methylphenyl | H | H | 4-F | 2-F, 5-F | |
| 4-268 | CH(CH₃)CH(CH₃)₂ | H | H | 4-Cl | 2-F, 5-F | |
| 4-269 | CH₂C(CH₃)₃ | H | H | 4-Cl | 2-F, 5-F | |
| 4-270 | 1-cyclopropylethyl | H | H | 4-Cl | 2-F, 5-F | |
| 4-271 | 2-methylphenyl | H | H | 4-Cl | 2-F, 5-F | |
| 4-272 | CH(CH₃)CH(CH₃)₂ | H | H | 4-Br | 2-F, 5-F | |
| 4-273 | CH₂C(CH₃)₃ | H | H | 4-Br | 2-F, 5-F | |
| 4-274 | 1-cyclopropylethyl | H | H | 4-Br | 2-F, 5-F | |
| 4-275 | 2-methylphenyl | H | H | 4-Br | 2-F, 5-F | |
| 4-276 | CH(CH₃)CH(CH₃)₂ | H | H | 4-F | 2-F, 6-F | |
| 4-277 | CH₂C(CH₃)₃ | H | H | 4-F | 2-F, 6-F | |

TABLE 4-continued (I-3b)

| No. | R¹ | R² | R³ | (R⁴)ₚ | (R⁹)_q | PP |
|---|---|---|---|---|---|---|
| 4-278 | CH(CH₃)-cyclopropyl | H | H | 4-F | 2-F, 6-F | |
| 4-279 | 2-methylphenyl | H | H | 4-F | 2-F, 6-F | |
| 4-280 | CH(CH₃)CH(CH₃)₂ | H | H | 4-Cl | 2-F, 6-F | |
| 4-281 | CH₂C(CH₃)₃ | H | H | 4-Cl | 2-F, 6-F | |
| 4-282 | CH(CH₃)-cyclopropyl | H | H | 4-Cl | 2-F, 6-F | |
| 4-283 | 2-methylphenyl | H | H | 4-Cl | 2-F, 6-F | |
| 4-284 | CH(CH₃)CH(CH₃)₂ | H | H | 4-Br | 2-F, 6-F | |
| 4-285 | CH₂C(CH₃)₃ | H | H | 4-Br | 2-F, 6-F | |
| 4-286 | CH(CH₃)-cyclopropyl | H | H | 4-Br | 2-F, 6-F | |
| 4-287 | 2-methylphenyl | H | H | 4-Br | 2-F, 6-F | |
| 4-288 | CH(CH₃)CH(CH₃)₂ | H | H | 4-F | 3-F, 4-F | |
| 4-289 | CH₂C(CH₃)₃ | H | H | 4-F | 3-F, 4-F | |
| 4-290 | CH(CH₃)-cyclopropyl | H | H | 4-F | 3-F, 4-F | |
| 4-291 | 2-methylphenyl | H | H | 4-F | 3-F, 4-F | |
| 4-292 | CH(CH₃)CH(CH₃)₂ | H | H | 4-Cl | 3-F, 4-F | |
| 4-293 | CH₂C(CH₃)₃ | H | H | 4-Cl | 3-F, 4-F | |
| 4-294 | CH(CH₃)-cyclopropyl | H | H | 4-Cl | 3-F, 4-F | |
| 4-295 | 2-methylphenyl | H | H | 4-Cl | 3-F, 4-F | |
| 4-296 | CH(CH₃)CH(CH₃)₂ | H | H | 4-Br | 3-F, 4-F | |
| 4-297 | CH₂C(CH₃)₃ | H | H | 4-Br | 3-F, 4-F | |
| 4-298 | CH(CH₃)-cyclopropyl | H | H | 4-Br | 3-F, 4-F | |
| 4-299 | 2-methylphenyl | H | H | 4-Br | 3-F, 4-F | |
| 4-300 | CH(CH₃)CH(CH₃)₂ | H | H | 4-F | 3-F, 5-F | |
| 4-301 | CH₂C(CH₃)₃ | H | H | 4-F | 3-F, 5-F | |
| 4-302 | CH(CH₃)-cyclopropyl | H | H | 4-F | 3-F, 5-F | |
| 4-303 | 2-methylphenyl | H | H | 4-F | 3-F, 5-F | |
| 4-304 | CH(CH₃)CH(CH₃)₂ | H | H | 4-Cl | 3-F, 5-F | |
| 4-305 | CH₂C(CH₃)₃ | H | H | 4-Cl | 3-F, 5-F | |
| 4-306 | CH(CH₃)-cyclopropyl | H | H | 4-Cl | 3-F, 5-F | |
| 4-307 | 2-methylphenyl | H | H | 4-Cl | 3-F, 5-F | |
| 4-308 | CH(CH₃)CH(CH₃)₂ | H | H | 4-Br | 3-F, 5-F | |
| 4-309 | CH₂C(CH₃)₃ | H | H | 4-Br | 3-F, 5-F | |
| 4-310 | CH(CH₃)-cyclopropyl | H | H | 4-Br | 3-F, 5-F | |
| 4-311 | 2-methylphenyl | H | H | 4-Br | 3-F, 5-F | |

TABLE 4-continued (I-3b)

| No. | R¹ | R² | R³ | (R⁴)ₚ | (R⁹)_q | PP |
|---|---|---|---|---|---|---|
| 4-312 | CH(CH₃)CH(CH₃)₂ | H | H | — | 2-Cl, 3-Cl | |
| 4-313 | 2-methylphenyl | H | H | — | 2-Cl, 3-Cl | |
| 4-314 | CH(CH₃)CH(CH₃)₂ | H | H | — | 2-Cl, 4-Cl | |
| 4-315 | 2-methylphenyl | H | H | — | 2-Cl, 4-Cl | |
| 4-316 | CH(CH₃)CH(CH₃)₂ | H | H | — | 2-Cl, 5-Cl | |
| 4-317 | 2-methylphenyl | H | H | — | 2-Cl, 5-Cl | |
| 4-318 | CH(CH₃)CH(CH₃)₂ | H | H | — | 2-Cl, 6-Cl | |
| 4-319 | 2-methylphenyl | H | H | — | 2-Cl, 6-Cl | |
| 4-320 | CH(CH₃)CH(CH₃)₂ | H | H | — | 3-Cl, 4-Cl | |
| 4-321 | 2-methylphenyl | H | H | — | 3-Cl, 4-Cl | |
| 4-322 | CH(CH₃)CH(CH₃)₂ | H | H | — | 3-Cl, 5-Cl | |
| 4-323 | 2-methylphenyl | H | H | — | 3-Cl, 5-Cl | |
| 4-324 | i-Bu | H | H | 4-F | 2-Cl, 3-Cl | |
| 4-325 | i-Bu | H | H | 4-Cl | 2-Cl, 3-Cl | |
| 4-326 | i-Bu | H | H | 4-Br | 2-Cl, 3-Cl | |
| 4-327 | i-Bu | H | H | 4-F | 2-Cl, 4-Cl | |
| 4-328 | i-Bu | H | H | 4-Cl | 2-Cl, 4-Cl | Oil |
| 4-329 | i-Bu | H | H | 4-Br | 2-Cl, 4-Cl | |
| 4-330 | i-Bu | H | H | 4-F | 2-Cl, 5-Cl | |
| 4-331 | i-Bu | H | H | 4-Cl | 2-Cl, 5-Cl | |
| 4-332 | i-Bu | H | H | 4-Br | 2-Cl, 5-Cl | |
| 4-333 | i-Bu | H | H | 4-F | 2-Cl, 6-Cl | |
| 4-334 | i-Bu | H | H | 4-Cl | 2-Cl, 6-Cl | |
| 4-335 | i-Bu | H | H | 4-Br | 2-Cl, 6-Cl | |
| 4-336 | i-Bu | H | H | 4-F | 3-Cl, 4-Cl | |
| 4-337 | i-Bu | H | H | 4-Cl | 3-Cl, 4-Cl | |
| 4-338 | i-Bu | H | H | 4-Br | 3-Cl, 4-Cl | |
| 4-339 | i-Bu | H | H | 4-F | 3-Cl, 5-Cl | |
| 4-340 | i-Bu | H | H | 4-Cl | 3-Cl, 5-Cl | |
| 4-341 | i-Bu | H | H | 4-Br | 3-Cl, 5-Cl | |
| 4-342 | CH(CH₃)CH(CH₃)₂ | H | H | — | 2-Br, 3-Br | |
| 4-343 | 2-methylphenyl | H | H | — | 2-Br, 3-Br | |
| 4-344 | CH(CH₃)CH(CH₃)₂ | H | H | — | 2-Br, 4-Br | |
| 4-345 | 2-methylphenyl | H | H | — | 2-Br, 4-Br | |
| 4-346 | CH(CH₃)CH(CH₃)₂ | H | H | — | 2-Br, 5-Br | |
| 4-347 | 2-methylphenyl | H | H | — | 2-Br, 5-Br | |
| 4-348 | CH(CH₃)CH(CH₃)₂ | H | H | — | 2-Br, 6-Br | |
| 4-349 | 2-methylphenyl | H | H | — | 2-Br, 6-Br | |
| 4-350 | CH(CH₃)CH(CH₃)₂ | H | H | — | 3-Br, 4-Br | |
| 4-351 | 2-methylphenyl | H | H | — | 3-Br, 4-Br | |
| 4-352 | CH(CH₃)CH(CH₃)₂ | H | H | — | 3-Br, 5-Br | |
| 4-353 | 2-methylphenyl | H | H | — | 3-Br, 5-Br | |
| 4-354 | i-Bu | H | H | 4-F | 2-Br, 3-Br | |
| 4-355 | i-Bu | H | H | 4-Cl | 2-Br, 3-Br | |
| 4-356 | i-Bu | H | H | 4-Br | 2-Br, 3-Br | |
| 4-357 | i-Bu | H | H | 4-F | 2-Br, 4-Br | |
| 4-358 | i-Bu | H | H | 4-Cl | 2-Br, 4-Br | |
| 4-359 | i-Bu | H | H | 4-Br | 2-Br, 4-Br | |
| 4-360 | i-Bu | H | H | 4-F | 2-Br, 5-Br | |
| 4-361 | i-Bu | H | H | 4-Cl | 2-Br, 5-Br | |

TABLE 4-continued

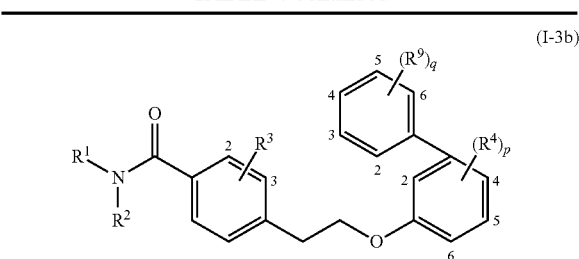
(I-3b)

| No. | R¹ | R² | R³ | (R⁴)ₚ | (R⁹)_q | PP |
|---|---|---|---|---|---|---|
| 4-362 | i-Bu | H | H | 4-Br | 2-Br, 5-Br | |
| 4-363 | i-Bu | H | H | 4-F | 2-Br, 6-Br | |
| 4-364 | i-Bu | H | H | 4-Cl | 2-Br, 6-Br | |
| 4-365 | i-Bu | H | H | 4-Br | 2-Br, 6-Br | |
| 4-366 | i-Bu | H | H | 4-F | 3-Br, 4-Br | |
| 4-367 | i-Bu | H | H | 4-Cl | 3-Br, 4-Br | |
| 4-368 | i-Bu | H | H | 4-Br | 3-Br, 4-Br | |
| 4-369 | i-Bu | H | H | 4-F | 3-Br, 5-Br | |
| 4-370 | i-Bu | H | H | 4-Cl | 3-Br, 5-Br | |
| 4-371 | i-Bu | H | H | 4-Br | 3-Br, 5-Br | |
| 4-372 | i-Bu | H | H | — | 2-F, 3-Cl | Oil |
| 4-373 | i-Bu | H | H | — | 2-F, 4-Cl | 101.1 |
| 4-374 | i-Bu | H | H | — | 2-F, 5-Cl | 95.4 |
| 4-375 | i-Bu | H | H | — | 2-F, 6-Cl | |
| 4-376 | i-Bu | H | H | — | 3-F, 4-Cl | Gum |
| 4-377 | i-Bu | H | H | — | 3-F, 5-Cl | Oil |
| 4-378 | i-Bu | H | H | — | 3-F, 6-Cl | Oil |
| 4-379 | i-Bu | H | H | — | 4-F, 5-Cl | 95.7 |
| 4-380 | i-Bu | H | H | — | 4-F, 6-Cl | Oil |
| 4-381 | i-Bu | H | H | — | 5-F, 6-Cl | Oil |
| 4-382 | CH(CH₃)CH(CH₃)₂ | H | H | — | 2-F, 3-Cl | |
| 4-383 | o-tolyl | H | H | — | 2-F, 3-Cl | |
| 4-384 | CH(CH₃)CH(CH₃)₂ | H | H | — | 2-F, 4-Cl | |
| 4-385 | o-tolyl | H | H | — | 2-F, 4-Cl | |
| 4-386 | CH(CH₃)CH(CH₃)₂ | H | H | — | 2-F, 5-Cl | |
| 4-387 | o-tolyl | H | H | — | 2-F, 5-Cl | |
| 4-388 | CH(CH₃)CH(CH₃)₂ | H | H | — | 2-F, 6-Cl | |
| 4-389 | o-tolyl | H | H | — | 2-F, 6-Cl | |
| 4-390 | CH(CH₃)CH(CH₃)₂ | H | H | — | 3-F, 4-Cl | |
| 4-391 | o-tolyl | H | H | — | 3-F, 4-Cl | |
| 4-392 | CH(CH₃)CH(CH₃)₂ | H | H | — | 3-F, 5-Cl | |
| 4-393 | o-tolyl | H | H | — | 3-F, 5-Cl | |
| 4-394 | CH(CH₃)CH(CH₃)₂ | H | H | — | 3-F, 6-Cl | |
| 4-395 | o-tolyl | H | H | — | 3-F, 6-Cl | |
| 4-396 | CH(CH₃)CH(CH₃)₂ | H | H | — | 4-F, 5-Cl | |
| 4-397 | o-tolyl | H | H | — | 4-F, 5-Cl | |
| 4-398 | CH(CH₃)CH(CH₃)₂ | H | H | — | 4-F, 6-Cl | |
| 4-399 | o-tolyl | H | H | — | 4-F, 6-Cl | |
| 4-400 | CH(CH₃)CH(CH₃)₂ | H | H | — | 5-F, 6-Cl | |
| 4-401 | o-tolyl | H | H | — | 5-F, 6-Cl | |
| 4-402 | i-Bu | H | H | 4-F | 2-F, 3-Cl | |
| 4-403 | i-Bu | H | H | 4-Cl | 2-F, 3-Cl | |
| 4-404 | i-Bu | H | H | 4-Br | 2-F, 3-Cl | |
| 4-405 | i-Bu | H | H | 4-F | 2-F, 4-Cl | |
| 4-406 | i-Bu | H | H | 4-Cl | 2-F, 4-Cl | |
| 4-407 | i-Bu | H | H | 4-Br | 2-F, 4-Cl | |
| 4-408 | i-Bu | H | H | 4-F | 2-F, 5-Cl | |
| 4-409 | i-Bu | H | H | 4-Cl | 2-F, 5-Cl | |
| 4-410 | i-Bu | H | H | 4-Br | 2-F, 5-Cl | |
| 4-411 | i-Bu | H | H | 4-F | 2-F, 6-Cl | |
| 4-412 | i-Bu | H | H | 4-Cl | 2-F, 6-Cl | |
| 4-413 | i-Bu | H | H | 4-Br | 2-F, 6-Cl | |
| 4-414 | i-Bu | H | H | 4-F | 3-F, 4-Cl | |
| 4-415 | i-Bu | H | H | 4-Cl | 3-F, 4-Cl | |
| 4-416 | i-Bu | H | H | 4-Br | 3-F, 4-Cl | |
| 4-417 | i-Bu | H | H | 4-F | 3-F, 5-Cl | |
| 4-418 | i-Bu | H | H | 4-Cl | 3-F, 5-Cl | |
| 4-419 | i-Bu | H | H | 4-Br | 3-F, 5-Cl | |
| 4-420 | i-Bu | H | H | 4-F | 3-F, 6-Cl | |
| 4-421 | i-Bu | H | H | 4-Cl | 3-F, 6-Cl | |
| 4-422 | i-Bu | H | H | 4-Br | 3-F, 6-Cl | |
| 4-423 | i-Bu | H | H | 4-F | 4-F, 5-Cl | |
| 4-424 | i-Bu | H | H | 4-Cl | 4-F, 5-Cl | |
| 4-425 | i-Bu | H | H | 4-Br | 4-F, 5-Cl | |

TABLE 4-continued

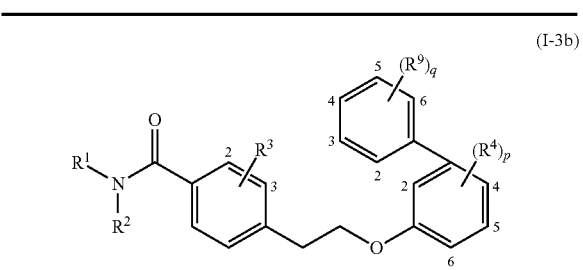

(I-3b)

| No. | R¹ | R² | R³ | (R⁴)$_p$ | (R⁹)$_q$ | PP |
|---|---|---|---|---|---|---|
| 4-426 | i-Bu | H | H | 4-F | 4-F, 6-Cl | |
| 4-427 | i-Bu | H | H | 4-Cl | 4-F, 6-Cl | |
| 4-428 | i-Bu | H | H | 4-Br | 4-F, 6-Cl | |
| 4-429 | i-Bu | H | H | 4-F | 5-F, 6-Cl | |
| 4-430 | i-Bu | H | H | 4-Cl | 5-F, 6-Cl | |
| 4-431 | i-Bu | H | H | 4-Br | 5-F, 6-Cl | |
| 4-432 | CH(CH₃)CH(CH₃)₂ | H | H | 4-F | 2-F, 3-Cl | |
| 4-433 | o-tolyl | H | H | 4-F | 2-F, 3-Cl | |
| 4-434 | CH(CH₃)CH(CH₃)₂ | H | H | 4-Cl | 2-F, 3-Cl | |
| 4-435 | o-tolyl | H | H | 4-Cl | 2-F, 3-Cl | |
| 4-436 | CH(CH₃)CH(CH₃)₂ | H | H | 4-Br | 2-F, 3-Cl | |
| 4-437 | o-tolyl | H | H | 4-Br | 2-F, 3-Cl | |
| 4-438 | CH(CH₃)CH(CH₃)₂ | H | H | 4-F | 2-F, 4-Cl | |
| 4-439 | o-tolyl | H | H | 4-F | 2-F, 4-Cl | |
| 4-440 | CH(CH₃)CH(CH₃)₂ | H | H | 4-Cl | 2-F, 4-Cl | |
| 4-441 | o-tolyl | H | H | 4-Cl | 2-F, 4-Cl | |
| 4-442 | CH(CH₃)CH(CH₃)₂ | H | H | 4-Br | 2-F, 4-Cl | |
| 4-443 | o-tolyl | H | H | 4-Br | 2-F, 4-Cl | |
| 4-444 | CH(CH₃)CH(CH₃)₂ | H | H | 4-F | 2-F, 5-Cl | |

TABLE 4-continued

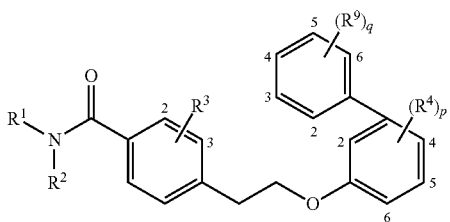

(I-3b)

| No. | R¹ | R² | R³ | (R⁴)$_p$ | (R⁹)$_q$ | PP |
|---|---|---|---|---|---|---|
| 4-445 | o-tolyl | H | H | 4-F | 2-F, 5-Cl | |
| 4-446 | CH(CH₃)CH(CH₃)₂ | H | H | 4-Cl | 2-F, 5-Cl | |
| 4-447 | o-tolyl | H | H | 4-Cl | 2-F, 5-Cl | |
| 4-448 | CH(CH₃)CH(CH₃)₂ | H | H | 4-Br | 2-F, 5-Cl | |
| 4-449 | o-tolyl | H | H | 4-Br | 2-F, 5-Cl | |
| 4-450 | CH(CH₃)CH(CH₃)₂ | H | H | 4-F | 2-F, 6-Cl | |
| 4-451 | o-tolyl | H | H | 4-F | 2-F, 6-Cl | |
| 4-452 | CH(CH₃)CH(CH₃)₂ | H | H | 4-Cl | 2-F, 6-Cl | |
| 4-453 | o-tolyl | H | H | 4-Cl | 2-F, 6-Cl | |
| 4-454 | CH(CH₃)CH(CH₃)₂ | H | H | 4-Br | 2-F, 6-Cl | |
| 4-455 | o-tolyl | H | H | 4-Br | 2-F, 6-Cl | |
| 4-456 | CH(CH₃)CH(CH₃)₂ | H | H | 4-F | 3-F, 4-Cl | |
| 4-457 | o-tolyl | H | H | 4-F | 3-F, 4-Cl | |
| 4-458 | CH(CH₃)CH(CH₃)₂ | H | H | 4-Cl | 3-F, 4-Cl | |

TABLE 4-continued (I-3b)

| No. | R¹ | R² | R³ | (R⁴)ₚ | (R⁹)_q | PP |
|---|---|---|---|---|---|---|
| 4-459 | 2-methylphenyl | H | H | 4-Cl | 3-F, 4-Cl | |
| 4-460 | CH(CH₃)CH(CH₃)₂ | H | H | 4-Br | 3-F, 4-Cl | |
| 4-461 | 3-methylphenyl | H | H | 4-Br | 3-F, 4-Cl | |
| 4-462 | CH(CH₃)CH(CH₃)₂ | H | H | 4-F | 3-F, 5-Cl | |
| 4-463 | 2-methylphenyl | H | H | 4-F | 3-F, 5-Cl | |
| 4-464 | CH(CH₃)CH(CH₃)₂ | H | H | 4-Cl | 3-F, 5-Cl | |
| 4-465 | 3-methylphenyl | H | H | 4-Cl | 3-F, 5-Cl | |
| 4-466 | CH(CH₃)CH(CH₃)₂ | H | H | 4-Br | 3-F, 5-Cl | |
| 4-467 | 2-methylphenyl | H | H | 4-Br | 3-F, 5-Cl | |
| 4-468 | CH(CH₃)CH(CH₃)₂ | H | H | 4-F | 3-F, 6-Cl | |
| 4-469 | 3-methylphenyl | H | H | 4-F | 3-F, 6-Cl | |
| 4-470 | CH(CH₃)CH(CH₃)₂ | H | H | 4-Cl | 3-F, 6-Cl | |
| 4-471 | 2-methylphenyl | H | H | 4-Cl | 3-F, 6-Cl | |
| 4-472 | CH(CH₃)CH(CH₃)₂ | H | H | 4-Br | 3-F, 6-Cl | |
| 4-473 | 3-methylphenyl | H | H | 4-Br | 3-F, 6-Cl | |
| 4-474 | CH(CH₃)CH(CH₃)₂ | H | H | 4-F | 4-F, 5-Cl | |
| 4-475 | 2-methylphenyl | H | H | 4-F | 4-F, 5-Cl | |
| 4-476 | CH(CH₃)CH(CH₃)₂ | H | H | 4-Cl | 4-F, 5-Cl | |
| 4-477 | 3-methylphenyl | H | H | 4-Cl | 4-F, 5-Cl | |
| 4-478 | CH(CH₃)CH(CH₃)₂ | H | H | 4-Br | 4-F, 5-Cl | |
| 4-479 | 2-methylphenyl | H | H | 4-Br | 4-F, 5-Cl | |
| 4-480 | CH(CH₃)CH(CH₃)₂ | H | H | 4-F | 4-F, 6-Cl | |
| 4-481 | 3-methylphenyl | H | H | 4-F | 4-F, 6-Cl | |
| 4-482 | CH(CH₃)CH(CH₃)₂ | H | H | 4-Cl | 4-F, 6-Cl | |
| 4-483 | 2-methylphenyl | H | H | 4-Cl | 4-F, 6-Cl | |
| 4-484 | CH(CH₃)CH(CH₃)₂ | H | H | 4-Br | 4-F, 6-Cl | |
| 4-485 | 3-methylphenyl | H | H | 4-Br | 4-F, 6-Cl | |
| 4-486 | CH(CH₃)CH(CH₃)₂ | H | H | 4-F | 5-F, 6-Cl | |

TABLE 4-continued (I-3b)

[Structure: R¹R²N-C(=O)-phenyl(R³, positions 2,3)-CH₂CH₂-O-phenyl(R⁴)p(positions 2,3,4,5,6)-phenyl(R⁹)q(positions 3,4,5,6)]

| No. | R¹ | R² | R³ | (R⁴)ₚ | (R⁹)q | PP |
|---|---|---|---|---|---|---|
| 4-487 | methylphenyl | H | H | 4-F | 5-F, 6-Cl | |
| 4-488 | CH(CH₃)CH(CH₃)₂ | H | H | 4-Cl | 5-F, 6-Cl | |
| 4-489 | methylphenyl | H | H | 4-Cl | 5-F, 6-Cl | |
| 4-490 | CH(CH₃)CH(CH₃)₂ | H | H | 4-Br | 5-F, 6-Cl | |
| 4-491 | methylphenyl | H | H | 4-Br | 5-F, 6-Cl | |
| 4-492 | i-Bu | H | H | — | 2-F, 3-Br | |
| 4-493 | i-Bu | H | H | — | 2-F, 4-Br | |
| 4-494 | i-Bu | H | H | — | 2-F, 5-Br | |
| 4-495 | i-Bu | H | H | — | 2-F, 6-Br | |
| 4-496 | i-Bu | H | H | — | 3-F, 4-Br | |
| 4-497 | i-Bu | H | H | — | 3-F, 5-Br | |
| 4-498 | i-Bu | H | H | — | 3-F, 6-Br | |
| 4-499 | i-Bu | H | H | — | 4-F, 5-Br | |
| 4-500 | i-Bu | H | H | — | 4-F, 6-Br | |
| 4-501 | i-Bu | H | H | — | 5-F, 6-Br | |
| 4-502 | CH(CH₃)CH(CH₃)₂ | H | H | — | 2-F, 3-Br | |
| 4-503 | methylphenyl | H | H | — | 2-F, 3-Br | |
| 4-504 | CH(CH₃)CH(CH₃)₂ | H | H | — | 2-F, 4-Br | |
| 4-505 | methylphenyl | H | H | — | 2-F, 4-Br | |
| 4-506 | CH(CH₃)CH(CH₃)₂ | H | H | — | 2-F, 5-Br | |
| 4-507 | methylphenyl | H | H | — | 2-F, 5-Br | |
| 4-508 | CH(CH₃)CH(CH₃)₂ | H | H | — | 2-F, 6-Br | |
| 4-509 | methylphenyl | H | H | — | 2-F, 6-Br | |
| 4-510 | CH(CH₃)CH(CH₃)₂ | H | H | — | 3-F, 4-Br | |
| 4-511 | methylphenyl | H | H | — | 3-F, 4-Br | |
| 4-512 | CH(CH₃)CH(CH₃)₂ | H | H | — | 3-F, 5-Br | |
| 4-513 | methylphenyl | H | H | — | 3-F, 5-Br | |
| 4-514 | CH(CH₃)CH(CH₃)₂ | H | H | — | 3-F, 6-Br | |
| 4-515 | methylphenyl | H | H | — | 3-F, 6-Br | |
| 4-516 | CH(CH₃)CH(CH₃)₂ | H | H | — | 4-F, 5-Br | |
| 4-517 | methylphenyl | H | H | — | 4-F, 5-Br | |
| 4-518 | CH(CH₃)CH(CH₃)₂ | H | H | — | 4-F, 6-Br | |
| 4-519 | methylphenyl | H | H | — | 4-F, 6-Br | |
| 4-520 | CH(CH₃)CH(CH₃)₂ | H | H | — | 5-F, 6-Br | |
| 4-521 | methylphenyl | H | H | — | 5-F, 6-Br | |
| 4-522 | i-Bu | H | H | 4-F | 2-F, 3-Br | |
| 4-523 | i-Bu | H | H | 4-Cl | 2-F, 3-Br | |
| 4-524 | i-Bu | H | H | 4-Br | 2-F, 3-Br | |
| 4-525 | i-Bu | H | H | 4-F | 2-F, 4-Br | |
| 4-526 | i-Bu | H | H | 4-Cl | 2-F, 4-Br | |
| 4-527 | i-Bu | H | H | 4-Br | 2-F, 4-Br | |

TABLE 4-continued (I-3b)

| No. | R¹ | R² | R³ | (R⁴)ₚ | (R⁹)_q | PP |
|---|---|---|---|---|---|---|
| 4-528 | i-Bu | H | H | 4-F | 2-F, 5-Br | |
| 4-529 | i-Bu | H | H | 4-Cl | 2-F, 5-Br | |
| 4-530 | i-Bu | H | H | 4-Br | 2-F, 5-Br | |
| 4-531 | i-Bu | H | H | 4-F | 2-F, 6-Br | |
| 4-532 | i-Bu | H | H | 4-Cl | 2-F, 6-Br | |
| 4-533 | i-Bu | H | H | 4-Br | 2-F, 6-Br | |
| 4-534 | i-Bu | H | H | 4-F | 3-F, 4-Br | |
| 4-535 | i-Bu | H | H | 4-Cl | 3-F, 4-Br | |
| 4-536 | i-Bu | H | H | 4-Br | 3-F, 4-Br | |
| 4-537 | i-Bu | H | H | 4-F | 3-F, 5-Br | |
| 4-538 | i-Bu | H | H | 4-Cl | 3-F, 5-Br | |
| 4-539 | i-Bu | H | H | 4-Br | 3-F, 5-Br | |
| 4-540 | i-Bu | H | H | 4-F | 3-F, 6-Br | |
| 4-541 | i-Bu | H | H | 4-Cl | 3-F, 6-Br | |
| 4-542 | i-Bu | H | H | 4-Br | 3-F, 6-Br | |
| 4-543 | i-Bu | H | H | 4-F | 4-F, 5-Br | |
| 4-544 | i-Bu | H | H | 4-Cl | 4-F, 5-Br | |
| 4-545 | i-Bu | H | H | 4-Br | 4-F, 5-Br | |
| 4-546 | i-Bu | H | H | 4-F | 4-F, 6-Br | |
| 4-547 | i-Bu | H | H | 4-Cl | 4-F, 6-Br | |
| 4-548 | i-Bu | H | H | 4-Br | 4-F, 6-Br | |
| 4-549 | i-Bu | H | H | 4-F | 5-F, 6-Br | |
| 4-550 | i-Bu | H | H | 4-Cl | 5-F, 6-Br | |
| 4-551 | i-Bu | H | H | 4-Br | 5-F, 6-Br | |
| 4-552 | CH(CH₃)CH(CH₃)₂ | H | H | 4-F | 2-F, 3-Br | |
| 4-553 | o-tolyl | H | H | 4-F | 2-F, 3-Br | |
| 4-554 | CH(CH₃)CH(CH₃)₂ | H | H | 4-Cl | 2-F, 3-Br | |
| 4-555 | o-tolyl | H | H | 4-Cl | 2-F, 3-Br | |
| 4-556 | CH(CH₃)CH(CH₃)₂ | H | H | 4-Br | 2-F, 3-Br | |
| 4-557 | o-tolyl | H | H | 4-Br | 2-F, 3-Br | |
| 4-558 | CH(CH₃)CH(CH₃)₂ | H | H | 4-F | 2-F, 4-Br | |
| 4-559 | o-tolyl | H | H | 4-F | 2-F, 4-Br | |
| 4-560 | CH(CH₃)CH(CH₃)₂ | H | H | 4-Cl | 2-F, 4-Br | |
| 4-561 | o-tolyl | H | H | 4-Cl | 2-F, 4-Br | |
| 4-562 | CH(CH₃)CH(CH₃)₂ | H | H | 4-Br | 2-F, 4-Br | |
| 4-563 | o-tolyl | H | H | 4-Br | 2-F, 4-Br | |
| 4-564 | CH(CH₃)CH(CH₃)₂ | H | H | 4-F | 2-F, 5-Br | |
| 4-565 | o-tolyl | H | H | 4-F | 2-F, 5-Br | |
| 4-566 | CH(CH₃)CH(CH₃)₂ | H | H | 4-Cl | 2-F, 5-Br | |
| 4-567 | o-tolyl | H | H | 4-Cl | 2-F, 5-Br | |
| 4-568 | CH(CH₃)CH(CH₃)₂ | H | H | 4-Br | 2-F, 5-Br | |
| 4-569 | o-tolyl | H | H | 4-Br | 2-F, 5-Br | |
| 4-570 | CH(CH₃)CH(CH₃)₂ | H | H | 4-F | 2-F, 6-Br | |
| 4-571 | o-tolyl | H | H | 4-F | 2-F, 6-Br | |
| 4-572 | CH(CH₃)CH(CH₃)₂ | H | H | 4-Cl | 2-F, 6-Br | |
| 4-573 | o-tolyl | H | H | 4-Cl | 2-F, 6-Br | |
| 4-574 | CH(CH₃)CH(CH₃)₂ | H | H | 4-Br | 2-F, 6-Br | |

TABLE 4-continued (I-3b)

| No. | R¹ | R² | R³ | (R⁴)ₚ | (R⁹)_q | PP |
|---|---|---|---|---|---|---|
| 4-575 | 2-methylphenyl | H | H | 4-Br | 2-F, 6-Br | |
| 4-576 | CH(CH₃)CH(CH₃)₂ | H | H | 4-F | 3-F, 4-Br | |
| 4-577 | 2-methylphenyl | H | H | 4-F | 3-F, 4-Br | |
| 4-578 | CH(CH₃)CH(CH₃)₂ | H | H | 4-Cl | 3-F, 4-Br | |
| 4-579 | 2-methylphenyl | H | H | 4-Cl | 3-F, 4-Br | |
| 4-580 | CH(CH₃)CH(CH₃)₂ | H | H | 4-Br | 3-F, 4-Br | |
| 4-581 | 2-methylphenyl | H | H | 4-Br | 3-F, 4-Br | |
| 4-582 | CH(CH₃)CH(CH₃)₂ | H | H | 4-F | 3-F, 5-Br | |
| 4-583 | 2-methylphenyl | H | H | 4-F | 3-F, 5-Br | |
| 4-584 | CH(CH₃)CH(CH₃)₂ | H | H | 4-Cl | 3-F, 5-Br | |
| 4-585 | 2-methylphenyl | H | H | 4-Cl | 3-F, 5-Br | |
| 4-586 | CH(CH₃)CH(CH₃)₂ | H | H | 4-Br | 3-F, 5-Br | |
| 4-587 | 2-methylphenyl | H | H | 4-Br | 3-F, 5-Br | |
| 4-588 | CH(CH₃)CH(CH₃)₂ | H | H | 4-F | 3-F, 6-Br | |
| 4-589 | 2-methylphenyl | H | H | 4-F | 3-F, 6-Br | |
| 4-590 | CH(CH₃)CH(CH₃)₂ | H | H | 4-Cl | 3-F, 6-Br | |
| 4-591 | 2-methylphenyl | H | H | 4-Cl | 3-F, 6-Br | |
| 4-592 | CH(CH₃)CH(CH₃)₂ | H | H | 4-Br | 3-F, 6-Br | |
| 4-593 | 2-methylphenyl | H | H | 4-Br | 3-F, 6-Br | |
| 4-594 | CH(CH₃)CH(CH₃)₂ | H | H | 4-F | 4-F, 5-Br | |
| 4-595 | 2-methylphenyl | H | H | 4-F | 4-F, 5-Br | |
| 4-596 | CH(CH₃)CH(CH₃)₂ | H | H | 4-Cl | 4-F, 5-Br | |
| 4-597 | 2-methylphenyl | H | H | 4-Cl | 4-F, 5-Br | |
| 4-598 | CH(CH₃)CH(CH₃)₂ | H | H | 4-Br | 4-F, 5-Br | |
| 4-599 | 2-methylphenyl | H | H | 4-Br | 4-F, 5-Br | |
| 4-600 | CH(CH₃)CH(CH₃)₂ | H | H | 4-F | 4-F, 6-Br | |
| 4-601 | 2-methylphenyl | H | H | 4-F | 4-F, 6-Br | |
| 4-602 | CH(CH₃)CH(CH₃)₂ | H | H | 4-Cl | 4-F, 6-Br | |

TABLE 4-continued (I-3b)

| No. | R¹ | R² | R³ | (R⁴)ₚ | (R⁹)_q | PP |
|---|---|---|---|---|---|---|
| 4-603 | 2-methylphenyl | H | H | 4-Cl | 4-F, 6-Br | |
| 4-604 | CH(CH₃)CH(CH₃)₂ | H | H | 4-Br | 4-F, 6-Br | |
| 4-605 | 2-methylphenyl | H | H | 4-Br | 4-F, 6-Br | |
| 4-606 | CH(CH₃)CH(CH₃)₂ | H | H | 4-F | 5-F, 6-Br | |
| 4-607 | 2-methylphenyl | H | H | 4-F | 5-F, 6-Br | |
| 4-608 | CH(CH₃)CH(CH₃)₂ | H | H | 4-Cl | 5-F, 6-Br | |
| 4-609 | 2-methylphenyl | H | H | 4-Cl | 5-F, 6-Br | |
| 4-610 | CH(CH₃)CH(CH₃)₂ | H | H | 4-Br | 5-F, 6-Br | |
| 4-611 | 2-methylphenyl | H | H | 4-Br | 5-F, 6-Br | |
| 4-612 | i-Bu | H | H | — | 2-Cl, 3-Br | |
| 4-613 | i-Bu | H | H | — | 2-Cl, 4-Br | |
| 4-614 | i-Bu | H | H | — | 2-Cl, 5-Br | |
| 4-615 | i-Bu | H | H | — | 2-Cl, 6-Br | |
| 4-616 | i-Bu | H | H | — | 3-Cl, 4-Br | |
| 4-617 | i-Bu | H | H | — | 3-Cl, 5-Br | |
| 4-618 | i-Bu | H | H | — | 3-Cl, 6-Br | |
| 4-619 | i-Bu | H | H | — | 4-Cl, 5-Br | |
| 4-620 | i-Bu | H | H | — | 4-Cl, 6-Br | |
| 4-621 | i-Bu | H | H | — | 5-Cl, 6-Br | |
| 4-622 | CH(CH₃)CH(CH₃)₂ | H | H | — | 2-Cl, 3-Br | |
| 4-623 | 2-methylphenyl | H | H | — | 2-Cl, 3-Br | |
| 4-624 | CH(CH₃)CH(CH₃)₂ | H | H | — | 2-Cl, 4-Br | |
| 4-625 | 2-methylphenyl | H | H | — | 2-Cl, 4-Br | |
| 4-626 | CH(CH₃)CH(CH₃)₂ | H | H | — | 2-Cl, 5-Br | |
| 4-627 | 2-methylphenyl | H | H | — | 2-Cl, 5-Br | |
| 4-628 | CH(CH₃)CH(CH₃)₂ | H | H | — | 2-Cl, 6-Br | |
| 4-629 | 2-methylphenyl | H | H | — | 2-Cl, 6-Br | |
| 4-630 | CH(CH₃)CH(CH₃)₂ | H | H | — | 3-Cl, 4-Br | |
| 4-631 | 2-methylphenyl | H | H | — | 3-Cl, 4-Br | |
| 4-632 | CH(CH₃)CH(CH₃)₂ | H | H | — | 3-Cl, 5-Br | |
| 4-633 | 2-methylphenyl | H | H | — | 3-Cl, 5-Br | |
| 4-634 | CH(CH₃)CH(CH₃)₂ | H | H | — | 3-Cl, 6-Br | |
| 4-635 | 2-methylphenyl | H | H | — | 3-Cl, 6-Br | |
| 4-636 | CH(CH₃)CH(CH₃)₂ | H | H | — | 4-Cl, 5-Br | |
| 4-637 | 2-methylphenyl | H | H | — | 4-Cl, 5-Br | |
| 4-638 | CH(CH₃)CH(CH₃)₂ | H | H | — | 4-Cl, 6-Br | |

TABLE 4-continued (I-3b)

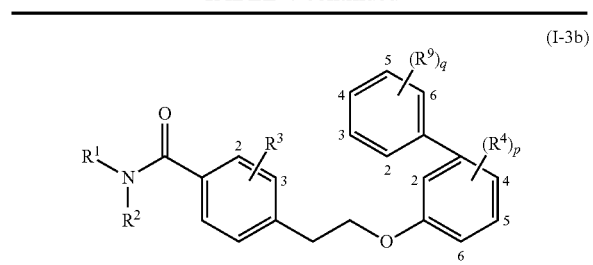

| No. | R¹ | R² | R³ | (R⁴)p | (R⁹)q | PP |
|---|---|---|---|---|---|---|
| 4-639 | (o-tolyl) | H | H | — | 4-Cl, 6-Br | |
| 4-640 | CH(CH₃)CH(CH₃)₂ | H | H | — | 5-Cl, 6-Br | |
| 4-641 | (o-tolyl) | H | H | — | 5-Cl, 6-Br | |
| 4-642 | i-Bu | H | H | 4-F | 2-Cl, 3-Br | |
| 4-643 | i-Bu | H | H | 4-Cl | 2-Cl, 3-Br | |
| 4-644 | i-Bu | H | H | 4-Br | 2-Cl, 3-Br | |
| 4-645 | i-Bu | H | H | 4-F | 2-Cl, 4-Br | |
| 4-646 | i-Bu | H | H | 4-Cl | 2-Cl, 4-Br | |
| 4-647 | i-Bu | H | H | 4-Br | 2-Cl, 4-Br | |
| 4-648 | i-Bu | H | H | 4-F | 2-Cl, 5-Br | |
| 4-649 | i-Bu | H | H | 4-Cl | 2-Cl, 5-Br | |
| 4-650 | i-Bu | H | H | 4-Br | 2-Cl, 5-Br | |
| 4-651 | i-Bu | H | H | 4-F | 2-Cl, 6-Br | |
| 4-652 | i-Bu | H | H | 4-Cl | 2-Cl, 6-Br | |
| 4-653 | i-Bu | H | H | 4-Br | 2-Cl, 6-Br | |
| 4-654 | i-Bu | H | H | 4-F | 3-Cl, 4-Br | |
| 4-655 | i-Bu | H | H | 4-Cl | 3-Cl, 4-Br | |
| 4-656 | i-Bu | H | H | 4-Br | 3-Cl, 4-Br | |
| 4-657 | i-Bu | H | H | 4-F | 3-Cl, 5-Br | |
| 4-658 | i-Bu | H | H | 4-Cl | 3-Cl, 5-Br | |
| 4-659 | i-Bu | H | H | 4-Br | 3-Cl, 5-Br | |
| 4-660 | i-Bu | H | H | 4-F | 3-Cl, 6-Br | |
| 4-661 | i-Bu | H | H | 4-Cl | 3-Cl, 6-Br | |

TABLE 4-continued (I-3b)

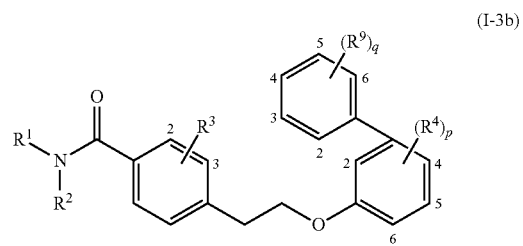

| No. | R¹ | R² | R³ | (R⁴)p | (R⁹)q | PP |
|---|---|---|---|---|---|---|
| 4-662 | i-Bu | H | H | 4-Br | 3-Cl, 6-Br | |
| 4-663 | i-Bu | H | H | 4-F | 4-Cl, 5-Br | |
| 4-664 | i-Bu | H | H | 4-Cl | 4-Cl, 5-Br | |
| 4-665 | i-Bu | H | H | 4-Br | 4-Cl, 5-Br | |
| 4-666 | i-Bu | H | H | 4-F | 4-Cl, 6-Br | |
| 4-667 | i-Bu | H | H | 4-Cl | 4-Cl, 6-Br | |
| 4-668 | i-Bu | H | H | 4-Br | 4-Cl, 6-Br | |
| 4-669 | i-Bu | H | H | 4-F | 5-Cl, 6-Br | |
| 4-670 | i-Bu | H | H | 4-Cl | 5-Cl, 6-Br | |
| 4-671 | i-Bu | H | H | 4-Br | 5-Cl, 6-Br | |
| 4-672 | i-Bu | H | H | — | 2-F, 3-F, 4-F | Oil |
| 4-673 | i-Bu | H | H | — | 2-F, 3-F, 5-F | Oil |
| 4-674 | i-Bu | H | H | — | 2-F, 3-F, 6-F | |
| 4-675 | i-Bu | H | H | — | 2-F, 4-F, 5-F | |
| 4-676 | i-Bu | H | H | — | 2-F, 4-F, 6-F | Oil |
| 4-677 | i-Bu | H | H | — | 3-F, 4-F, 5-F | Oil |
| 4-678 | i-Bu | H | H | — | 2-Cl, 3-F, 4-F | |
| 4-679 | i-Bu | H | H | — | 2-F, 3-Cl, 4-F | |
| 4-680 | i-Bu | H | H | — | 2-F, 3-F, 4-Cl | |
| 4-681 | i-Bu | H | H | — | 2-Cl, 3-F, 5-F | |
| 4-682 | i-Bu | H | H | — | 2-F, 3-Cl, 5-F | |
| 4-683 | i-Bu | H | H | — | 2-F, 3-F, 5-Cl | |
| 4-684 | i-Bu | H | H | — | 2-Cl, 3-F, 6-F | |
| 4-685 | i-Bu | H | H | — | 2-F, 3-Cl, 6-F | |
| 4-686 | i-Bu | H | H | — | 2-F, 3-F, 6-Cl | |
| 4-687 | i-Bu | H | H | — | 2-Cl, 4-F, 5-F | |
| 4-688 | i-Bu | H | H | — | 2-F, 4-Cl, 5-F | |
| 4-689 | i-Bu | H | H | — | 2-Cl, 4-F, 6-F | |
| 4-690 | i-Bu | H | H | — | 2-F, 4-Cl, 6-F | |
| 4-691 | i-Bu | H | H | — | 2-F, 4-F, 6-Cl | |
| 4-692 | i-Bu | H | H | — | 3-Cl, 4-F, 5-F | |
| 4-693 | i-Bu | H | H | — | 3-F, 4-Cl, 5-F | |

PP: Physical properties

TABLE 5

(I-3c)

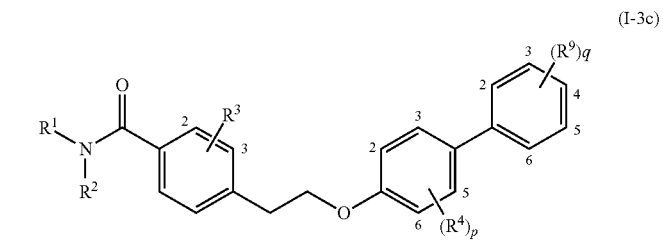

| No. | R¹ | R² | R³ | (R⁴)p | (R⁹)q | PP |
|---|---|---|---|---|---|---|
| 5-1 | i-Bu | H | H | — | — | 159.0 |
| 5-2 | i-Bu | H | H | — | 2-F | |
| 5-3 | i-Bu | H | H | — | 3-F | |
| 5-4 | i-Bu | H | H | — | 4-F | |
| 5-5 | i-Bu | H | H | — | 2-Cl | |
| 5-6 | i-Bu | H | H | — | 3-Cl | |
| 5-7 | i-Bu | H | H | — | 4-Cl | |
| 5-8 | i-Bu | H | H | — | 2-F, 3-F | |
| 5-9 | i-Bu | H | H | — | 2-F, 4-F | |
| 5-10 | i-Bu | H | H | — | 2-F, 5-F | |
| 5-11 | i-Bu | H | H | — | 2-F, 6-F | |

TABLE 5-continued (I-3c)

| No. | R¹ | R² | R³ | (R⁴)$_p$ | (R⁹)$_q$ | PP |
|---|---|---|---|---|---|---|
| 5-12 | i-Bu | H | H | — | 3-F, 4-F | |
| 5-13 | i-Bu | H | H | — | 3-F, 5-F | |
| 5-14 | CH(CH₃)CH(CH₃)₂ | H | H | — | — | |
| 5-15 | *(o-tolyl)* | H | H | — | — | |
| 5-16 | i-Bu | H | H | 3-F | — | |
| 5-17 | i-Bu | H | H | 3-Cl | — | |
| 5-18 | i-Bu | H | H | 3-Br | — | |
| 5-19 | i-Bu | H | H | 3-I | — | |
| 5-20 | i-Bu | H | H | 3-CF₃ | — | |
| 5-21 | i-Bu | H | H | 3-OCF₃ | — | |

PP: Physical properties

TABLE 6

(I-4a-1)

| No. | R¹ | R² | R³ | (R⁴)$_p$ | (R⁹)$_r$ | PP |
|---|---|---|---|---|---|---|
| 6-1 | i-Bu | H | H | — | — | 96.0 |
| 6-2 | CH(CH₃)CH(CH₃)₂ | H | H | — | — | 115.4 |
| 6-3 | i-Bu | H | H | 4-F | — | |
| 6-4 | i-Bu | H | H | 4-Cl | — | |
| 6-5 | i-Bu | H | H | 4-Br | — | |
| 6-6 | CH(CH₃)CH(CH₃)₂ | H | H | 4-F | — | |
| 6-7 | CH(CH₃)CH(CH₃)₂ | H | H | 4-Cl | — | |
| 6-8 | CH(CH₃)CH(CH₃)₂ | H | H | 4-Br | — | |
| 6-9 | i-Bu | H | H | — | 3-F | |
| 6-10 | i-Bu | H | H | — | 3-Cl | |
| 6-11 | i-Bu | H | H | — | 3-CF₃ | |
| 6-12 | i-Bu | H | H | — | 5-F | |
| 6-13 | i-Bu | H | H | — | 5-Cl | |
| 6-14 | i-Bu | H | H | — | 5-CF₃ | |
| 6-15 | i-Bu | H | H | — | 3-F, 5-F | |
| 6-16 | i-Bu | H | H | — | 3-Cl, 5-Cl | |
| 6-17 | i-Bu | H | H | — | 3-CF₃, 5-Cl | |
| 6-18 | CH(CH₃)CH(CH₃)₂ | H | H | — | 3-F | |
| 6-19 | CH(CH₃)CH(CH₃)₂ | H | H | — | 3-Cl | |
| 6-20 | CH(CH₃)CH(CH₃)₂ | H | H | — | 3-CF₃ | |
| 6-21 | CH(CH₃)CH(CH₃)₂ | H | H | — | 5-F | |
| 6-22 | CH(CH₃)CH(CH₃)₂ | H | H | — | 5-Cl | |
| 6-23 | CH(CH₃)CH(CH₃)₂ | H | H | — | 5-CF₃ | |
| 6-24 | CH(CH₃)CH(CH₃)₂ | H | H | — | 3-F, 5-F | |
| 6-25 | CH(CH₃)CH(CH₃)₂ | H | H | — | 3-Cl, 5-Cl | |
| 6-26 | CH(CH₃)CH(CH₃)₂ | H | H | — | 3-CF₃, 5-Cl | |
| 6-27 | i-Bu | H | H | 4-F | 3-F | |
| 6-28 | i-Bu | H | H | 4-F | 3-Cl | |
| 6-29 | i-Bu | H | H | 4-F | 3-CF3 | |
| 6-30 | i-Bu | H | H | 4-F | 5-F | |
| 6-31 | i-Bu | H | H | 4-F | 5-Cl | |
| 6-32 | i-Bu | H | H | 4-F | 5-CF₃ | |
| 6-33 | i-Bu | H | H | 4-F | 3-F, 5-F | |
| 6-34 | i-Bu | H | H | 4-F | 3-Cl, 5-Cl | |
| 6-35 | i-Bu | H | H | 4-F | 3-CF₃, 5-Cl | |
| 6-36 | i-Bu | H | H | 4-Cl | 3-F | |
| 6-37 | i-Bu | H | H | 4-Cl | 3-Cl | |
| 6-38 | i-Bu | H | H | 4-Cl | 3-CF₃ | |
| 6-39 | i-Bu | H | H | 4-Cl | 5-F | |
| 6-40 | i-Bu | H | H | 4-Cl | 5-Cl | |
| 6-41 | i-Bu | H | H | 4-Cl | 5-CF₃ | |
| 6-42 | i-Bu | H | H | 4-Cl | 3-F, 5-F | |
| 6-43 | i-Bu | H | H | 4-Cl | 3-Cl, 5-Cl | |
| 6-44 | i-Bu | H | H | 4-Cl | 3-CF₃, 5-Cl | |
| 6-45 | i-Bu | H | H | 4-Br | 3-F | |
| 6-46 | i-Bu | H | H | 4-Br | 3-Cl | |
| 6-47 | i-Bu | H | H | 4-Br | 3-CF₃ | |
| 6-48 | i-Bu | H | H | 4-Br | 5-F | |
| 6-49 | i-Bu | H | H | 4-Br | 5-Cl | |
| 6-50 | i-Bu | H | H | 4-Br | 5-CF₃ | |

TABLE 6-continued (I-4a-1)

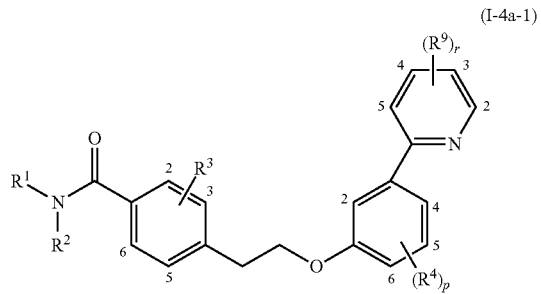

| No. | R¹ | R² | R³ | (R⁴)p | (R⁹)r | PP |
|---|---|---|---|---|---|---|
| 6-51 | i-Bu | H | H | 4-Br | 3-F, 5-F | |
| 6-52 | i-Bu | H | H | 4-Br | 3-Cl, 5-Cl | |
| 6-53 | i-Bu | H | H | 4-Br | 3-CF₃, 5-Cl | |
| 6-54 | CH(CH₃)CH(CH₃)₂ | H | H | 4-F | 3-F | |
| 6-55 | CH(CH₃)CH(CH₃)₂ | H | H | 4-F | 3-Cl | |
| 6-56 | CH(CH₃)CH(CH₃)₂ | H | H | 4-F | 3-CF₃ | |
| 6-57 | CH(CH₃)CH(CH₃)₂ | H | H | 4-F | 5-F | |
| 6-58 | CH(CH₃)CH(CH₃)₂ | H | H | 4-F | 5-Cl | |
| 6-59 | CH(CH₃)CH(CH₃)₂ | H | H | 4-F | 5-CF₃ | |
| 6-60 | CH(CH₃)CH(CH₃)₂ | H | H | 4-F | 3-F, 5-F | |
| 6-61 | CH(CH₃)CH(CH₃)₂ | H | H | 4-F | 3-Cl, 5-Cl | |
| 6-62 | CH(CH₃)CH(CH₃)₂ | H | H | 4-F | 3-CF₃, 5-Cl | |
| 6-63 | CH(CH₃)CH(CH₃)₂ | H | H | 4-Cl | 3-F | |
| 6-64 | CH(CH₃)CH(CH₃)₂ | H | H | 4-Cl | 3-Cl | |
| 6-65 | CH(CH₃)CH(CH₃)₂ | H | H | 4-Cl | 3-CF₃ | |
| 6-66 | CH(CH₃)CH(CH₃)₂ | H | H | 4-Cl | 5-F | |
| 6-67 | CH(CH₃)CH(CH₃)₂ | H | H | 4-Cl | 5-Cl | |
| 6-68 | CH(CH₃)CH(CH₃)₂ | H | H | 4-Cl | 5-CF₃ | |
| 6-69 | CH(CH₃)CH(CH₃)₂ | H | H | 4-Cl | 3-F, 5-F | |
| 6-70 | CH(CH₃)CH(CH₃)₂ | H | H | 4-Cl | 3-Cl, 5-Cl | |
| 6-71 | CH(CH₃)CH(CH₃)₂ | H | H | 4-Cl | 3-CF₃, 5-Cl | |
| 6-72 | CH(CH₃)CH(CH₃)₂ | H | H | 4-Br | 3-F | |
| 6-73 | CH(CH₃)CH(CH₃)₂ | H | H | 4-Br | 3-Cl | |
| 6-74 | CH(CH₃)CH(CH₃)₂ | H | H | 4-Br | 3-CF₃ | |
| 6-75 | CH(CH₃)CH(CH₃)₂ | H | H | 4-Br | 5-F | |
| 6-76 | CH(CH₃)CH(CH₃)₂ | H | H | 4-Br | 5-Cl | |
| 6-77 | CH(CH₃)CH(CH₃)₂ | H | H | 4-Br | 5-CF₃ | |
| 6-78 | CH(CH₃)CH(CH₃)₂ | H | H | 4-Br | 3-F, 5-F | |
| 6-79 | CH(CH₃)CH(CH₃)₂ | H | H | 4-Br | 3-Cl, 5-Cl | |
| 6-80 | CH(CH₃)CH(CH₃)₂ | H | H | 4-Br | 3-CF₃, 5-Cl | |

PP: Physical properties

TABLE 7

(I-4a-2)

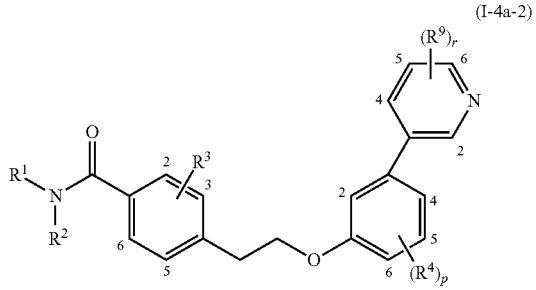

| No. | R¹ | R² | R³ | (R⁴)p | (R⁹)r | PP |
|---|---|---|---|---|---|---|
| 7-1 | i-Bu | H | H | — | — | |
| 7-2 | CH(CH₃)CH(CH₃)₂ | H | H | — | — | |
| 7-3 | i-Bu | H | H | 4-F | — | |
| 7-4 | i-Bu | H | H | 4-Cl | — | |

TABLE 7-continued (I-4a-2)

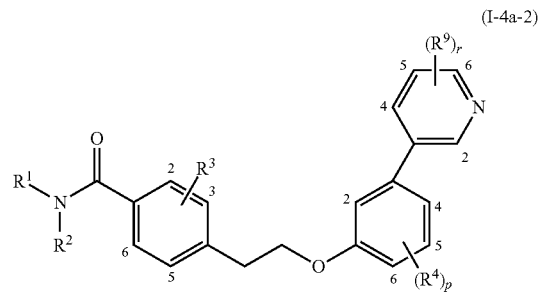

| No. | R¹ | R² | R³ | (R⁴)p | (R⁹)r | PP |
|---|---|---|---|---|---|---|
| 7-5 | i-Bu | H | H | 4-Br | — | |
| 7-6 | CH(CH₃)CH(CH₃)₂ | H | H | 4-F | — | |
| 7-7 | CH(CH₃)CH(CH₃)₂ | H | H | 4-Cl | — | |
| 7-8 | CH(CH₃)CH(CH₃)₂ | H | H | 4-Br | — | |
| 7-9 | i-Bu | H | H | — | 2-F | |
| 7-10 | i-Bu | H | H | — | 2-Cl | |
| 7-11 | i-Bu | H | H | — | 2-CF₃ | |
| 7-12 | i-Bu | H | H | — | 6-F | |
| 7-13 | i-Bu | H | H | — | 6-Cl | |
| 7-14 | i-Bu | H | H | — | 6-CF₃ | |
| 7-15 | i-Bu | H | H | — | 2-F, 6-F | |
| 7-16 | i-Bu | H | H | — | 2-Cl, 6-Cl | |
| 7-17 | i-Bu | H | H | — | 2-CF₃, 6-Cl | |
| 7-18 | CH(CH₃)CH(CH₃)₂ | H | H | — | 2-F | |
| 7-19 | CH(CH₃)CH(CH₃)₂ | H | H | — | 2-Cl | |
| 7-20 | CH(CH₃)CH(CH₃)₂ | H | H | — | 2-CF₃ | |
| 7-21 | CH(CH₃)CH(CH₃)₂ | H | H | — | 6-F | |
| 7-22 | CH(CH₃)CH(CH₃)₂ | H | H | — | 6-Cl | |
| 7-23 | CH(CH₃)CH(CH₃)₂ | H | H | — | 6-CF₃ | |
| 7-24 | CH(CH₃)CH(CH₃)₂ | H | H | — | 2-F, 6-F | |
| 7-25 | CH(CH₃)CH(CH₃)₂ | H | H | — | 2-Cl, 6-Cl | |
| 7-26 | CH(CH₃)CH(CH₃)₂ | H | H | — | 2-CF₃, 6-Cl | |
| 7-27 | i-Bu | H | H | 4-F | 2-F | |
| 7-28 | i-Bu | H | H | 4-F | 2-Cl | |
| 7-29 | i-Bu | H | H | 4-F | 2-CF₃ | |
| 7-30 | i-Bu | H | H | 4-F | 6-F | |
| 7-31 | i-Bu | H | H | 4-F | 6-Cl | |
| 7-32 | i-Bu | H | H | 4-F | 6-CF₃ | |
| 7-33 | i-Bu | H | H | 4-F | 2-F, 6-F | |
| 7-34 | i-Bu | H | H | 4-F | 2-Cl, 6-Cl | |
| 7-35 | i-Bu | H | H | 4-F | 2-CF₃, 6-Cl | |
| 7-36 | i-Bu | H | H | 4-Cl | 2-F | |
| 7-37 | i-Bu | H | H | 4-Cl | 2-Cl | |
| 7-38 | i-Bu | H | H | 4-Cl | 2-CF₃ | |
| 7-39 | i-Bu | H | H | 4-Cl | 6-F | |
| 7-40 | i-Bu | H | H | 4-Cl | 6-Cl | |
| 7-41 | i-Bu | H | H | 4-Cl | 6-CF₃ | |
| 7-42 | i-Bu | H | H | 4-Cl | 2-F, 6-F | |
| 7-43 | i-Bu | H | H | 4-Cl | 2-Cl, 6-Cl | |
| 7-44 | i-Bu | H | H | 4-Cl | 2-CF₃, 6-Cl | |
| 7-45 | i-Bu | H | H | 4-Br | 2-F | |
| 7-46 | i-Bu | H | H | 4-Br | 2-Cl | |
| 7-47 | i-Bu | H | H | 4-Br | 2-CF₃ | |
| 7-48 | i-Bu | H | H | 4-Br | 6-F | |
| 7-49 | i-Bu | H | H | 4-Br | 6-Cl | |
| 7-50 | i-Bu | H | H | 4-Br | 6-CF₃ | |
| 7-51 | i-Bu | H | H | 4-Br | 2-F, 6-F | |
| 7-52 | i-Bu | H | H | 4-Br | 2-Cl, 6-Cl | |
| 7-53 | i-Bu | H | H | 4-Br | 2-CF₃, 6-Cl | |
| 7-54 | CH(CH₃)CH(CH₃)₂ | H | H | 4-F | 2-F | |
| 7-55 | CH(CH₃)CH(CH₃)₂ | H | H | 4-F | 2-Cl | |
| 7-56 | CH(CH₃)CH(CH₃)₂ | H | H | 4-F | 2-CF₃ | |
| 7-57 | CH(CH₃)CH(CH₃)₂ | H | H | 4-F | 6-F | |
| 7-58 | CH(CH₃)CH(CH₃)₂ | H | H | 4-F | 6-Cl | |
| 7-59 | CH(CH₃)CH(CH₃)₂ | H | H | 4-F | 6-CF₃ | |
| 7-60 | CH(CH₃)CH(CH₃)₂ | H | H | 4-F | 2-F, 6-F | |

TABLE 7-continued (I-4a-2)

| No. | R¹ | R² | R³ | (R⁴)ₚ | (R⁹)ᵣ | PP |
|---|---|---|---|---|---|---|
| 7-61 | CH(CH₃)CH(CH₃)₂ | H | H | 4-F | 2-Cl, 6-Cl | |
| 7-62 | CH(CH₃)CH(CH₃)₂ | H | H | 4-F | 2-CF₃, 6-Cl | |
| 7-63 | CH(CH₃)CH(CH₃)₂ | H | H | 4-Cl | 2-F | |
| 7-64 | CH(CH₃)CH(CH₃)₂ | H | H | 4-Cl | 2-Cl | |
| 7-65 | CH(CH₃)CH(CH₃)₂ | H | H | 4-Cl | 2-CF₃ | |
| 7-66 | CH(CH₃)CH(CH₃)₂ | H | H | 4-Cl | 6-F | |
| 7-67 | CH(CH₃)CH(CH₃)₂ | H | H | 4-Cl | 6-Cl | |
| 7-68 | CH(CH₃)CH(CH₃)₂ | H | H | 4-Cl | 6-CF₃ | |
| 7-69 | CH(CH₃)CH(CH₃)₂ | H | H | 4-Cl | 2-F, 6-F | |
| 7-70 | CH(CH₃)CH(CH₃)₂ | H | H | 4-Cl | 2-Cl, 6-Cl | |
| 7-71 | CH(CH₃)CH(CH₃)₂ | H | H | 4-Cl | 2-CF₃, 6-Cl | |
| 7-72 | CH(CH₃)CH(CH₃)₂ | H | H | 4-Br | 2-F | |
| 7-73 | CH(CH₃)CH(CH₃)₂ | H | H | 4-Br | 2-Cl | |
| 7-74 | CH(CH₃)CH(CH₃)₂ | H | H | 4-Br | 2-CF₃ | |
| 7-75 | CH(CH₃)CH(CH₃)₂ | H | H | 4-Br | 6-F | |
| 7-76 | CH(CH₃)CH(CH₃)₂ | H | H | 4-Br | 6-Cl | |
| 7-77 | CH(CH₃)CH(CH₃)₂ | H | H | 4-Br | 6-CF₃ | |
| 7-78 | CH(CH₃)CH(CH₃)₂ | H | H | 4-Br | 2-F, 6-F | |
| 7-79 | CH(CH₃)CH(CH₃)₂ | H | H | 4-Br | 2-Cl, 6-Cl | |
| 7-80 | CH(CH₃)CH(CH₃)₂ | H | H | 4-Br | 2-CF₃, 6-Cl | |

PP: Physical properties

TABLE 8

(I-4b-1)

| No. | R¹ | R² | R³ | (R⁴)ₚ | (R⁹)ₛ | PP |
|---|---|---|---|---|---|---|
| 8-1 | i-Bu | H | H | — | — | 128.0 |
| 8-2 | CH(CH₃)CH(CH₃)₂ | H | H | — | — | 129.1 |
| 8-3 | i-Bu | H | H | — | 2-Cl | |
| 8-4 | i-Bu | H | H | — | 4-Cl | |
| 8-5 | i-Bu | H | H | — | 5-Cl | |
| 8-6 | i-Bu | H | H | — | 2-Cl, 5-Cl | |
| 8-7 | i-Bu | H | H | — | 2-F | |
| 8-8 | i-Bu | H | H | — | 4-F | |
| 8-9 | i-Bu | H | H | — | 5-F | |
| 8-10 | i-Bu | H | H | — | 2-F, 5-F | |
| 8-11 | i-Bu | H | H | 4-Cl | 2-Cl | |
| 8-12 | i-Bu | H | H | 4-Cl | 4-Cl | |
| 8-13 | i-Bu | H | H | 4-Cl | 5-Cl | |
| 8-14 | i-Bu | H | H | 4-Cl | 2-Cl, 5-Cl | |
| 8-15 | i-Bu | H | H | 4-Cl | 2-F | |
| 8-16 | i-Bu | H | H | 4-Cl | 4-F | |
| 8-17 | i-Bu | H | H | 4-Cl | 5-F | |
| 8-18 | i-Bu | H | H | 4-Cl | 2-F, 5-F | |
| 8-19 | i-Bu | H | H | 4-F | 2-Cl | |
| 8-20 | i-Bu | H | H | 4-F | 4-Cl | |
| 8-21 | i-Bu | H | H | 4-F | 5-Cl | |
| 8-22 | i-Bu | H | H | 4-F | 2-Cl, 5-Cl | |
| 8-23 | i-Bu | H | H | 4-F | 2-F | |
| 8-24 | i-Bu | H | H | 4-F | 4-F | |
| 8-25 | i-Bu | H | H | 4-F | 5-F | |
| 8-26 | i-Bu | H | H | 4-F | 2-F, 5-F | |
| 8-27 | i-Bu | H | H | 4-F | 2-F, 5-F | |
| 8-28 | CH(CH₃)CH(CH₃)₂ | H | H | — | 2-Cl | |
| 8-29 | CH(CH₃)CH(CH₃)₂ | H | H | — | 4-Cl | |
| 8-30 | CH(CH₃)CH(CH₃)₂ | H | H | — | 5-Cl | |
| 8-31 | CH(CH₃)CH(CH₃)₂ | H | H | — | 2-Cl, 5-Cl | |
| 8-32 | CH(CH₃)CH(CH₃)₂ | H | H | — | 2-F | |
| 8-33 | CH(CH₃)CH(CH₃)₂ | H | H | — | 4-F | |
| 8-34 | CH(CH₃)CH(CH₃)₂ | H | H | — | 5-F | |
| 8-35 | CH(CH₃)CH(CH₃)₂ | H | H | — | 2-F, 5-F | |
| 8-36 | CH(CH₃)CH(CH₃)₂ | H | H | 4-Cl | 2-Cl | |
| 8-37 | CH(CH₃)CH(CH₃)₂ | H | H | 4-Cl | 4-Cl | |
| 8-38 | CH(CH₃)CH(CH₃)₂ | H | H | 4-Cl | 5-Cl | |
| 8-39 | CH(CH₃)CH(CH₃)₂ | H | H | 4-Cl | 2-Cl, 5-Cl | |
| 8-40 | CH(CH₃)CH(CH₃)₂ | H | H | 4-Cl | 2-F | |
| 8-41 | CH(CH₃)CH(CH₃)₂ | H | H | 4-Cl | 4-F | |
| 8-42 | CH(CH₃)CH(CH₃)₂ | H | H | 4-Cl | 5-F | |
| 8-43 | CH(CH₃)CH(CH₃)₂ | H | H | 4-Cl | 2-F, 5-F | |
| 8-44 | CH(CH₃)CH(CH₃)₂ | H | H | 4-F | 2-Cl | |
| 8-45 | CH(CH₃)CH(CH₃)₂ | H | H | 4-F | 4-Cl | |
| 8-46 | CH(CH₃)CH(CH₃)₂ | H | H | 4-F | 5-Cl | |
| 8-47 | CH(CH₃)CH(CH₃)₂ | H | H | 4-F | 2-Cl, 5-Cl | |
| 8-48 | CH(CH₃)CH(CH₃)₂ | H | H | 4-F | 2-F | |
| 8-49 | CH(CH₃)CH(CH₃)₂ | H | H | 4-F | 4-F | |
| 8-50 | CH(CH₃)CH(CH₃)₂ | H | H | 4-F | 5-F | |
| 8-51 | CH(CH₃)CH(CH₃)₂ | H | H | 4-F | 2-F< 5-F | |

PP: Physical properties

TABLE 9

(I-4b-2)

| No. | R¹ | R² | R³ | (R⁴)ₚ | (R⁹)ₛ | PP |
|---|---|---|---|---|---|---|
| 9-1 | i-Bu | H | H | — | — | 91.8 |
| 9-2 | CH(CH₃)CH(CH₃)₂ | H | H | — | — | 101.1 |

TABLE 9-continued (I-4b-2)

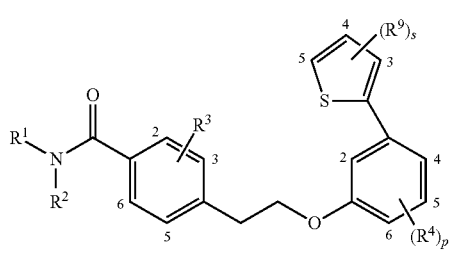

| No. | R¹ | R² | R³ | (R⁴)ₚ | (R⁹)ₛ | PP |
|---|---|---|---|---|---|---|
| 9-3 | i-Bu | H | H | — | 3-Cl | |
| 9-4 | i-Bu | H | H | — | 4-Cl | |
| 9-5 | i-Bu | H | H | — | 5-Cl | |
| 9-6 | i-Bu | H | H | — | 4-Cl, 5-Cl | |
| 9-7 | i-Bu | H | H | — | 3-F | |
| 9-8 | i-Bu | H | H | — | 4-F | |
| 9-9 | i-Bu | H | H | — | 5-F | |
| 9-10 | i-Bu | H | H | — | 4-F, 5-F | |
| 9-11 | i-Bu | H | H | 4-Cl | 3-Cl | |
| 9-12 | i-Bu | H | H | 4-Cl | 4-Cl | |
| 9-13 | i-Bu | H | H | 4-Cl | 5-Cl | |
| 9-14 | i-Bu | H | H | 4-Cl | 4-Cl, 5-Cl | |
| 9-15 | i-Bu | H | H | 4-Cl | 3-F | |
| 9-16 | i-Bu | H | H | 4-Cl | 4-F | |
| 9-17 | i-Bu | H | H | 4-Cl | 5-F | |
| 9-18 | i-Bu | H | H | 4-Cl | 4-F, 5-F | |
| 9-19 | i-Bu | H | H | 4-F | 3-Cl | |
| 9-20 | i-Bu | H | H | 4-F | 4-Cl | |
| 9-21 | i-Bu | H | H | 4-F | 5-Cl | |
| 9-22 | i-Bu | H | H | 4-F | 4-Cl, 5-Cl | |
| 9-23 | i-Bu | H | H | 4-F | 3-F | |
| 9-24 | i-Bu | H | H | 4-F | 4-F | |
| 9-25 | i-Bu | H | H | 4-F | 5-F | |
| 9-26 | i-Bu | H | H | 4-F | 4-F, 5-F | |
| 9-27 | i-Bu | H | H | 4-F | 2-F, 5-F | |
| 9-28 | CH(CH₃)CH(CH₃)₂ | H | H | — | 3-Cl | |
| 9-29 | CH(CH₃)CH(CH₃)₂ | H | H | — | 4-Cl | |
| 9-30 | CH(CH₃)CH(CH₃)₂ | H | H | — | 5-Cl | |
| 9-31 | CH(CH₃)CH(CH₃)₂ | H | H | — | 4-Cl, 5-Cl | |
| 9-32 | CH(CH₃)CH(CH₃)₂ | H | H | — | 3-F | |
| 9-33 | CH(CH₃)CH(CH₃)₂ | H | H | — | 4-F | |
| 9-34 | CH(CH₃)CH(CH₃)₂ | H | H | — | 5-F | |
| 9-35 | CH(CH₃)CH(CH₃)₂ | H | H | — | 4-F, 5-F | |
| 9-36 | CH(CH₃)CH(CH₃)₂ | H | H | 4-Cl | 3-Cl | |
| 9-37 | CH(CH₃)CH(CH₃)₂ | H | H | 4-Cl | 4-Cl | |
| 9-38 | CH(CH₃)CH(CH₃)₂ | H | H | 4-Cl | 5-Cl | |
| 9-39 | CH(CH₃)CH(CH₃)₂ | H | H | 4-Cl | 4-Cl, 5-Cl | |
| 9-40 | CH(CH₃)CH(CH₃)₂ | H | H | 4-Cl | 3-F | |
| 9-41 | CH(CH₃)CH(CH₃)₂ | H | H | 4-Cl | 4-F | |
| 9-42 | CH(CH₃)CH(CH₃)₂ | H | H | 4-Cl | 5-F | |
| 9-43 | CH(CH₃)CH(CH₃)₂ | H | H | 4-Cl | 4-F, 5-F | |
| 9-44 | CH(CH₃)CH(CH₃)₂ | H | H | 4-F | 3-Cl | |
| 9-45 | CH(CH₃)CH(CH₃)₂ | H | H | 4-F | 4-Cl | |
| 9-46 | CH(CH₃)CH(CH₃)₂ | H | H | 4-F | 5-Cl | |
| 9-47 | CH(CH₃)CH(CH₃)₂ | H | H | 4-F | 4-Cl, 5-Cl | |
| 9-48 | CH(CH₃)CH(CH₃)₂ | H | H | 4-F | 3-F | |
| 9-49 | CH(CH₃)CH(CH₃)₂ | H | H | 4-F | 4-F | |
| 9-50 | CH(CH₃)CH(CH₃)₂ | H | H | 4-F | 5-F | |
| 9-51 | CH(CH₃)CH(CH₃)₂ | H | H | 4-F | 4-F, 5-F | |

PP: Physical properties

TABLE 10

(I-5a)

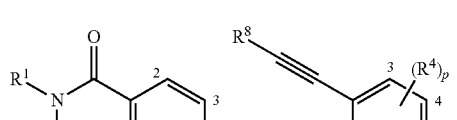

| No. | R¹ | R² | R³ | (R⁴)ₚ | R⁸ | PP |
|---|---|---|---|---|---|---|
| 10-1 | i-Bu | H | H | — | Si(CH₃)₃ | |
| 10-2 | i-Bu | H | H | — | H | |
| 10-3 | CH(CH₃)CH(CH₃)₂ | H | H | — | Si(CH₃)₃ | |
| 10-4 | *o-tolyl* | H | H | — | Si(CH₃)₃ | |
| 10-5 | i-Bu | H | H | 3-F | Si(CH₃)₃ | |
| 10-6 | i-Bu | H | H | 4-F | Si(CH₃)₃ | |
| 10-7 | i-Bu | H | H | 3-Cl | Si(CH₃)₃ | |
| 10-8 | i-Bu | H | H | 4-Cl | Si(CH₃)₃ | |
| 10-9 | i-Bu | H | H | 3-Br | Si(CH₃)₃ | |
| 10-10 | i-Bu | H | H | 4-Br | Si(CH₃)₃ | |
| 10-11 | i-Bu | H | H | 3-I | Si(CH₃)₃ | |
| 10-12 | i-Bu | H | H | 4-I | Si(CH₃)₃ | |
| 10-13 | i-Bu | H | H | 3-CF₃ | Si(CH₃)₃ | |
| 10-14 | i-Bu | H | H | 4-CF₃ | Si(CH₃)₃ | |
| 10-15 | i-Bu | H | H | 3-OCF₃ | Si(CH₃)₃ | |
| 10-16 | i-Bu | H | H | 4-OCF₃ | Si(CH₃)₃ | |
| 10-17 | i-Bu | H | H | — | C(CH₃)₃ | |
| 10-18 | CH(CH₃)CH(CH₃)₂ | H | H | — | C(CH₃)₃ | |
| 10-19 | *m-tolyl* | H | H | — | C(CH₃)₃ | |
| 10-20 | i-Bu | H | H | 3-F | C(CH₃)₃ | |
| 10-21 | i-Bu | H | H | 4-F | C(CH₃)₃ | |
| 10-22 | i-Bu | H | H | 3-Cl | C(CH₃)₃ | |
| 10-23 | i-Bu | H | H | 4-Cl | C(CH₃)₃ | |
| 10-24 | i-Bu | H | H | 3-Br | C(CH₃)₃ | |
| 10-25 | i-Bu | H | H | 4-Br | C(CH₃)₃ | |
| 10-26 | i-Bu | H | H | 3-I | C(CH₃)₃ | |
| 10-27 | i-Bu | H | H | 4-I | C(CH₃)₃ | |
| 10-28 | i-Bu | H | H | 3-CF₃ | C(CH₃)₃ | |
| 10-29 | i-Bu | H | H | 4-CF₃ | C(CH₃)₃ | |
| 10-30 | i-Bu | H | H | 3-OCF | C(CH₃)₃ | |
| 10-31 | i-Bu | H | H | 4-OCF₃ | C(CH₃)₃ | |

PP: Physical properties

TABLE 11

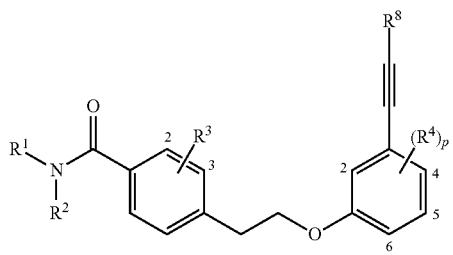
(I-5b)

| No. | R¹ | R² | R³ | (R⁴)ₚ | R⁸ | PP |
|---|---|---|---|---|---|---|
| 11-1 | i-Bu | H | H | — | Si(CH₃)₃ | Solid |
| 11-2 | i-Bu | H | H | — | H | Oil |
| 11-3 | i-Bu | H | H | — | CH₃ | |
| 11-4 | i-Bu | H | H | — | CH₂CH₃ | |
| 11-5 | i-Bu | H | H | — | CH₂CH₂CH₃ | 119.1 |
| 11-6 | i-Bu | H | H | — | CH₂CH₂CH₂CH₃ | |
| 11-7 | i-Bu | H | H | — | CH₂CH₂CH₂CH₂CH₃ | |
| 11-8 | i-Bu | H | H | — | CH₂CH₂CH₂CH₂CH₂CH₃ | |
| 11-9 | i-Bu | H | H | — | CH(CH₃)₂ | |
| 11-10 | i-Bu | H | H | — | CH₂CH(CH₃)₂ | |
| 11-11 | i-Bu | H | H | — | C(CH₃)₃ | Solid |
| 11-12 | i-Bu | H | H | — | CH₂C(CH₃)₃ | |
| 11-13 | i-Bu | H | H | — | COCH₃ | |
| 11-14 | i-Bu | H | H | — | CO₂CH₃ | |
| 11-15 | i-Bu | H | H | — | CH₂NH₂ | |
| 11-16 | i-Bu | H | H | — | CH₂NHCH₃ | |
| 11-17 | i-Bu | H | H | — | CH₂N(CH₃)₂ | |
| 11-18 | i-Bu | H | H | — | cyclopropyl | |
| 11-19 | i-Bu | H | H | — | cyclopentyl | |
| 11-20 | i-Bu | H | H | — | cyclohexyl | Solid |
| 11-21 | i-Bu | H | H | — | phenyl | Solid |
| 11-22 | i-Bu | H | H | — | 2-pyridyl | |
| 11-23 | CH(CH₃)CH(CH₃)₂ | H | H | — | Si(CH₃)₃ | |
| 11-24 | CH₂C(CH₃)₃ | H | H | — | Si(CH₃)₃ | |
| 11-25 | CH(CH₃)(cyclopropyl) | H | H | — | Si(CH₃)₃ | |
| 11-26 | 2-methylphenyl | H | H | — | Si(CH₃)₃ | |
| 11-27 | i-Bu | H | H | 4-F | Si(CH₃)₃ | |
| 11-28 | i-Bu | H | H | 4-F, 5-F | Si(CH₃)₃ | |
| 11-29 | i-Bu | H | H | 4-F, 5-Cl | Si(CH₃)₃ | |
| 11-30 | i-Bu | H | H | 4-F, 5-Br | Si(CH₃)₃ | |

TABLE 11-continued (I-5b)

| No. | R¹ | R² | R³ | (R⁴)$_p$ | R⁸ | PP |
|---|---|---|---|---|---|---|
| 11-31 | i-Bu | H | H | 4-Cl | Si(CH$_3$)$_3$ | Oil |
| 11-32 | i-Bu | H | H | 4-Cl, 5-F | Si(CH$_3$)$_3$ | |
| 11-33 | i-Bu | H | H | 4-Cl, 5-Cl | Si(CH$_3$)$_3$ | |
| 11-34 | i-Bu | H | H | 4-Cl, 5-Br | Si(CH$_3$)$_3$ | |
| 11-35 | i-Bu | H | H | 4-Br | Si(CH$_3$)$_3$ | |
| 11-36 | i-Bu | H | H | 4-Br, 5-F | Si(CH$_3$) | |
| 11-37 | i-Bu | H | H | 4-Br, 5-Cl | Si(CH$_3$)$_3$ | |
| 11-38 | i-Bu | H | H | 4-Br, 5-Br | Si(CH$_3$)$_3$ | |
| 11-39 | i-Bu | H | H | 4-I | Si(CH$_3$)$_3$ | |
| 11-40 | i-Bu | H | H | 4-I, 5-F | Si(CH$_3$)$_3$ | |
| 11-41 | i-Bu | H | H | 4-I, 5-Cl | Si(CH$_3$)$_3$ | |
| 11-42 | i-Bu | H | H | 4-I, 5-Br | Si(CH$_3$)$_3$ | |
| 11-43 | i-Bu | H | H | 4-CH$_3$ | Si(CH$_3$)$_3$ | |
| 11-44 | i-Bu | H | H | 4-CF$_3$ | Si(CH$_3$)$_3$ | |
| 11-45 | i-Bu | H | H | 4-OMe | Si(CH$_3$)$_3$ | |
| 11-46 | i-Bu | H | H | 4-OCF$_3$ | Si(CH$_3$)$_3$ | |
| 11-47 | CH(CH$_3$)CH(CH$_3$)$_2$ | H | H | 4-F | Si(CH$_3$)$_3$ | |
| 11-48 | CH(CH$_3$)CH(CH$_3$)$_2$ | H | H | 4-Cl | Si(CH$_3$)$_3$ | |
| 11-49 | CH(CH$_3$)CH(CH$_3$)$_2$ | H | H | 4-Br | Si(CH$_3$)$_3$ | |
| 11-50 | (2-methylphenyl) | H | H | 4-F | Si(CH$_3$)$_3$ | |
| 11-51 | (2-methylphenyl) | H | H | 4-Cl | Si(CH$_3$)$_3$ | |
| 11-52 | (2-methylphenyl) | H | H | 4-Br | Si(CH$_3$)$_3$ | |
| 11-53 | CH(CH$_3$)CH(CH$_3$)$_2$ | H | H | — | C(CH$_3$)$_3$ | |
| 11-54 | CH$_2$C(CH$_3$) | H | H | — | C(CH$_3$)$_3$ | |
| 11-55 | (1-cyclopropylethyl) | H | H | — | C(CH$_3$)$_3$ | |
| 11-56 | (2-methylphenyl) | H | H | — | C(CH$_3$)$_3$ | |
| 11-57 | i-Bu | H | H | 4-F | C(CH$_3$)$_3$ | |
| 11-58 | i-Bu | H | H | 4-F, 5-F | C(CH$_3$)$_3$ | |
| 11-59 | i-Bu | H | H | 4-F, 5-Cl | C(CH$_3$)$_3$ | |
| 11-60 | i-Bu | H | H | 4-F, 5-Br | C(CH$_3$)$_3$ | |
| 11-61 | i-Bu | H | H | 4-Cl | C(CH$_3$)$_3$ | |
| 11-62 | i-Bu | H | H | 4-Cl, 5-F | C(CH$_3$)$_3$ | |

TABLE 11-continued (I-5b)

| No. | R$^1$ | R$^2$ | R$^3$ | (R$^4$)$_p$ | R$^8$ | PP |
|---|---|---|---|---|---|---|
| 11-63 | i-Bu | H | H | 4-Cl, 5-Cl | C(CH$_3$)$_3$ | |
| 11-64 | i-Bu | H | H | 4-Cl, 5-Br | C(CH$_3$)$_3$ | |
| 11-65 | i-Bu | H | H | 4-Br | C(CH$_3$)$_3$ | |
| 11-66 | i-Bu | H | H | 4-Br, 5-F | C(CH$_3$)$_3$ | |
| 11-67 | i-Bu | H | H | 4-Br, 5-Cl | C(CH$_3$)$_3$ | |
| 11-68 | i-Bu | H | H | 4-Br, 5-Br | C(CH$_3$)$_3$ | |
| 11-69 | i-Bu | H | H | 4-I | C(CH$_3$)$_3$ | |
| 11-70 | i-Bu | H | H | 4-I, 5-F | C(CH$_3$)$_3$ | |
| 11-71 | i-Bu | H | H | 4-I, 5-Cl | C(CH$_3$)$_3$ | |
| 11-72 | i-Bu | H | H | 4-I, 5-Br | C(CH$_3$)$_3$ | |
| 11-73 | i-Bu | H | H | 4-Me | C(CH$_3$)$_3$ | |
| 11-74 | i-Bu | H | H | 4-CF$_3$ | C(CH$_3$)$_3$ | |
| 11-75 | i-Bu | H | H | 4-OMe | C(CH$_3$)$_3$ | |
| 11-76 | i-Bu | H | H | 4-OCF$_3$ | C(CH$_3$)$_3$ | |
| 11-77 | CH(CH$_3$)CH(CH$_3$)$_2$ | H | H | 4-F | C(CH$_3$)$_3$ | |
| 11-78 | CH(CH$_3$)CH(CH$_3$)$_2$ | H | H | 4-Cl | C(CH$_3$)$_3$ | |
| 11-79 | CH(CH$_3$)CH(CH$_3$)$_2$ | H | H | 4-Br | C(CH$_3$)$_3$ | |
| 11-80 | 2-methylphenyl | H | H | 4-F | C(CH$_3$)$_3$ | |
| 11-81 | 2-methylphenyl | H | H | 4-Cl | C(CH$_3$)$_3$ | |
| 11-82 | 2-methylphenyl | H | H | 4-Br | C(CH$_3$)$_3$ | |

PP: Physical properties

TABLE 12

(I-5c)

| No. | R$^1$ | R$^2$ | R$^3$ | (R$^4$)$_p$ | R$^8$ | PP |
|---|---|---|---|---|---|---|
| 12-1 | i-Bu | H | H | — | Si(CH$_3$)$_3$ | |
| 12-2 | i-Bu | H | H | — | H | |
| 12-3 | CH(CH$_3$)CH(CH$_3$)$_2$ | H | H | — | Si(CH$_3$)$_3$ | |
| 12-4 | 3-methylphenyl | H | H | — | Si(CH$_3$)$_3$ | |

TABLE 12-continued (I-5c)

| No. | R¹ | R² | R³ | (R⁴)ₚ | R⁸ | PP |
|---|---|---|---|---|---|---|
| 12-5 | i-Bu | H | H | 3-F | Si(CH₃)₃ | |
| 12-6 | i-Bu | H | H | 3-Cl | Si(CH₃)₃ | |
| 12-7 | i-Bu | H | H | 3-Br | Si(CH₃)₃ | |
| 12-8 | i-Bu | H | H | 3-I | Si(CH₃)₃ | |
| 12-9 | i-Bu | H | H | 3-CF₃ | Si(CH₃)₃ | |
| 12-10 | i-Bu | H | H | 3-OCF₃ | Si(CH₃)₃ | |
| 12-11 | i-Bu | H | H | — | C(CH₃)₃ | |
| 12-12 | CH(CH₃)CH(CH₃)₂ | H | H | — | C(CH₃)₃ | |
| 12-13 | 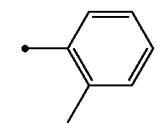 | H | H | — | C(CH₃)₃ | |

TABLE 12-continued (I-5c)

| No. | R¹ | R² | R³ | (R⁴)ₚ | R⁸ | PP |
|---|---|---|---|---|---|---|
| 12-14 | i-Bu | H | H | 3-F | C(CH₃)₃ | |
| 12-15 | i-Bu | H | H | 3-Cl | C(CH₃)₃ | |
| 12-16 | i-Bu | H | H | 3-Br | C(CH₃)₃ | |
| 12-17 | i-Bu | H | H | 3-I | C(CH₃)₃ | |
| 12-18 | i-Bu | H | H | 3-CF₃ | C(CH₃)₃ | |
| 12-19 | i-Bu | H | H | 3-OCF₃ | C(CH₃)₃ | |

PP: Physical properties

With respect to some of the invention compounds, ¹H-NMR data [measured by ¹H-nuclear magnetic resonance spectroscopy, δ is a chemical shift value (ppm)] are shown in Tables 13, 14 and 15.

TABLE 13

| No. | ¹H-NMR δ ppm<br>Measuring instrument: VARIAN MERCURY plus (300 MHz), Solvent: CDCl₃ |
|---|---|
| 1-129 | 7.72(d, 2H, J = 8.1 Hz), 7.34(d, 2H, J = 8.1 Hz), 7.30-7.21(m, 1H), 6.81 (d, 2H, J = 8.4 Hz), 6.80(d, 1H, J = 8.1 Hz), 6.73(s, 1H), 6.12-6.02(br, 1H), 4.18(t, 2H, J = 6.6 Hz), 3.52-3.40(m, 2H), 3.14(t, 2H, J = 6.6 Hz), 1.60-1.22(m, 4H), 0.96(t, 3H, J = 7.2 Hz) |
| 1-130 | 7.72(d, 2H, J = 8.4 Hz), 7.34(d, 2H, J = 8.4 Hz), 7.29-7.23(m, 1H), 6.81 (d, 1H, J = 8.4 Hz), 6.80(d, 1H, J = 8.1 Hz), 6.73(s, 1H), 5.85-5.78(br, 1H), 4.20-4.05(m, 1H), 4.18(t, 2H, J = 6.6 Hz), 3.14(t, 2H, J = 6.6 Hz), 1.62-1.53(m, 2H), 1.23(d, 3H, J = 6.6 Hz), 0.97(t, 3H, J = 7.5 Hz) |
| 1-132 | 7.72(d, 2H, J = 8.1 Hz), 7.35(d, 2H, J = 8.1 Hz), 7.26(dd, 1H, J = 8.4 Hz, 8.4 Hz), 6.81(d, 1H, J = 8.4 Hz), 6.80(d, 1H, J = 8.4 Hz), 6.75-6.71(br, 1H), 6.15-6.05(br, 1H), 4.18(t, 2H, J = 6.9 Hz), 3.45-3.23(m, 2H), 3.14(t, 2H, J = 6.9 Hz), 1.76-1.16(m, 3H), 0.96(d, 3H, J = 6.9 Hz), 0.94(t, 3H, J = 7.2 Hz) |
| 1-133 | 7.73(d, 2H, J = 8.4 Hz), 7.36(d, 2H, J = 8.4 Hz), 7.29-7.23(m, 1H), 6.81 (d, 1H, J = 8.4 Hz), 6.80(d, 1H, J = 8.4 Hz), 6.73(s, 1H), 6.18-6.05(br, 1H), 4.18(t, 2H, J = 6.6 Hz), 3.28(d, 2H, J = 6.6 Hz), 3.14(t, 2H, J = 6.6 Hz), 0.98(s, 9H) |
| 1-135 | 9.26-9.20(br, 1H), 7.75(d, 2H, J = 8.4 Hz), 7.34(d, 2H, J = 8.4 Hz), 7.30-7.24(m, 1H), 6.84-6.78(m, 2H), 6.75-6.70(m, 1H), 4.19(t, 2H, J = 6.9 Hz), 3.37(d, 2H, J = 4.5 Hz), 3.14(t, 2H, J = 6.9 Hz), 2.37(s, 6H), 0.99(s, 6H) |
| 1-136 | 7.74(d, 2H, J = 8.4 Hz), 7.36(d, 2H, J = 8.4 Hz), 7.34-7.23(m, 1H), 6.83-6.78(m, 2H), 6.74-6.72(m, 1H), 6.35-6.25(br, 1H), 4.49(t, 1H, J = 5.4 Hz), 4.18(t, 2H, J = 6.6 Hz), 3.61(dd, 2H, J = 5.4 Hz, 5.4 Hz), 3.44(s, 6H), 3.14(t, 2H, J = 6.6 Hz) |
| 1-145 | 7.40-7.22(m, 5H), 6.85-6.78(m, 2H), 6.77-6.72(m, 1H), 4.18(t, 2H, J = 6.9 Hz), 4.17-3.95(m, 1H), 3.13(t, 2H, J = 6.9 Hz), 1.20(d, 6H, J = 6.6 Hz) |
| 1-152 | 7.72(d, 2H, J = 8.1 Hz), 7.35(d, 2H, J = 8.1 Hz), 7.29-7.24(m, 1H), 6.81 (d, 1H, J = 8.4 Hz), 6.80(d, 1H, J = 8.4 Hz), 6.73(s, 1H), 6.22-6.18(br, 1H), 4.18(t, 2H, J = 6.6 Hz), 4.03-3.95(m, 2H), 3.44-3.32(m, 4H), 3.14(t, 2H, J = 6.6 Hz), 1.97-1.82(m, 1H), 1.72-1.62(m, 2H), 1.46-1.30(m, 2H) |
| 1-154 | 7.72(d, 2H, J = 8.1 Hz), 7.35(d, 2H, J = 8.1 Hz), 7.29-7.23(m, 1H), 6.83-6.78(m, 2H), 6.73(s, 1H), 6.21-6.15(br, 1H), 4.18(t, 2H, J = 6.6 Hz), 3.39-3.34(m, 2H), 3.14(t, 2H, J = 6.6 Hz), 2.90-2.80(m, 2H), 2.27(s, 3H), 1.97-1.85(m, 2H), 1.81-1.70(m, 2H), 1.70-1.55(m, 1H), 1.44-1.31(m, 2H) |
| 1-156 | 7.42-7.21(m, 5H), 6.85-6.77(m, 2H), 6.74(s, 1H), 4.17(t, 2H, J = 6.9 Hz), 3.42-2.89(m, 7H), 2.19-1.81(m, 1H), 1.05-0.70(m, 6H) |
| 1-161 | 7.73(d, 2H, J = 8.4 Hz), 7.35(d, 2H, J = 8.4 Hz), 7.29-7.23(m, 1H), 6.83-6.78(m, 2H), 6.73(s, 1H), 6.10-6.02(br, 1H), 4.18(t, 2H, J = 6.6 Hz), 3.68-3.52(m, 1H), 3.14(t, 2H, J = 6.6 Hz), 1.31(d, 3H, J = 6.6 Hz), 0.96-0.84(m, 1H), 0.60-0.25(m, 4H) |

TABLE 13-continued

| No. | $^1$H-NMR δ ppm<br>Measuring instrument: VARIAN MERCURY plus (300 MHz), Solvent: CDCl$_3$ |
|---|---|
| 1-162 | 7.71(d, 2H, J = 8.1 Hz), 7.34(d, 2H, J = 8.1 Hz), 7.29-7.23(m, 1H), 6.83-6.78(m, 2H), 6.73(s, 1H), 5.86-5.78(br, 1H), 4.25-4.10(m, 1H), 4.18 (t, 2H, J = 6.6 Hz), 3.14(t, 2H, J = 6.6 Hz), 1.57-1.35(m, 4H), 1.23(d, 3 H, J = 6.6 Hz), 0.94(t, 3H, J = 7.2 Hz) |
| 1-163 | 7.71(d, 2H, J = 8.1 Hz), 7.34(d, 2H, J = 8.1 Hz), 7.29-7.23(m, 1H), 6.82-6.78(m, 2H), 6.73(s, 1H), 5.85-5.75(br, 1H), 4.35-4.20(m, 1H), 4.17 (t, 2H, J = 6.6 Hz), 3.14(t, 2H, J = 6.6 Hz), 1.76-1.60(m, 1H), 1.52-1.25 (m, 2H), 1.22(d, 3H, J = 6.6 Hz), 0.95(d, 3H, J = 6.6 Hz), 0.94(d, 3H, J = 6.6 Hz) |
| 1-166 | 7.71(d, 2H, J = 8.1 Hz), 7.34(d, 2H, J = 8.1 Hz), 7.29-7.23(m, 1H), 6.83-6.78(m, 2H), 6.73(s, 1H), 5.86-5.75(br, 1H), 4.24-4.08(m, 1H), 4.18 (t, 2H, J = 6.6 Hz), 3.14(t, 2H, J = 6.6 Hz), 1.56-1.46(m, 2H), 1.43-1.22 (m, 6H), 1.23(d, 3H, J = 6.6 Hz) |
| 1-167 | 7.68(d, 2H, J = 8.1 Hz), 7.33(d, 2H, J = 8.1 Hz), 7.29-7.23(m, 1H), 6.82-6.78(m, 2H), 6.74-6.72(m, 1H), 5.96-5.85(br, 1H), 4.17(t, 2H, J = 6.6 Hz), 3.13(t, 2H, J = 6.6 Hz), 1.47(s, 9H) |
| 1-170 | 7.68(d, 2H, J = 8.1 Hz), 7.33(d, 2H, J = 8.1 Hz), 7.29-7.23(m, 1H), 6.83-6.78(m, 2H), 6.74-6.72(m, 1H), 5.82-5.78(br, 1H), 4.17(t, 2H, J = 6.6 Hz), 3.13(t, 2H, J = 6.6 Hz), 1.85(q, 2H, J = 7.5 Hz), 1.41(s, 6H), 0.90(t, 3H, J = 7.5 Hz) |
| 1-173 | 7.75(d, 2H, J = 8.1 Hz), 7.36(d, 2H, J = 8.1 Hz), 7.29-7.23(m, 1H), 6.92-6.78(m, 3H), 6.74(s, 1H), 4.18(t, 2H, J = 6.6 Hz), 3.77-3.65(m, 1H), 3.37-3.16(m, 2H), 3.14(t, 2H, J = 6.6 Hz), 2.90-2.78(m, 1H), 2.74-2.63(m, 1H), 2.30-2.12(m, 2H), 1.96-1.57(m, 4H), 1.12(t, 3H, J = 7.2 Hz) |
| 1-174 | 7.76(d, 2H, J = 8.1 Hz), 7.40-7.20(m, 7H), 6.82-6.79(m, 2H), 6.73(s, 1 H), 6.53(d, 1H, J = 7.2 Hz), 4.58-4.52(m, 1H), 4.18(t, 2H, J = 6.6 Hz), 3.14(t, 2H, J = 6.6 Hz), 1.26-1.15(m, 1H), 0.74-0.40(m, 4H) |
| 1-175 | 7.66(d, 2H, J = 8.4 Hz), 7.33(d, 2H, J = 8.4 Hz), 7.29-7.23(m, 1H), 6.83-6.78(m, 2H), 6.73(s, 1H), 5.92(s, 1H), 4.17(t, 2H, J = 6.6 Hz), 3.13(t, 2H, J = 6.6 Hz), 1.86(s, 2H), 1.52(s, 6H), 1.04(s, 9H) |
| 1-176 | 7.73(d, 2H, J = 8.1 Hz), 7.36(d, 2H, J = 8.1 Hz), 7.29-7.23(m, 1H), 6.83-6.78(m, 2H), 6.74(s, 1H), 5.96(d, 1H, J = 9.6 Hz), 4.18(t, 2H, J = 6.6 Hz), 4.00-3.89(m, 1H), 3.14(t, 2H, J = 6.6 Hz), 2.05-1.95(br, 2H), 1.74-1.53(m, 12H), 1.13(d, 3H, J = 6.9 Hz) |
| 1-177 | 7.71(d, 2H, J = 8.1 Hz), 7.35(d, 2H, J = 8.1 Hz), 7.29-7.23(m, 1H), 6.83-6.78(m, 2H), 6.73(s, 1H), 5.99(d, 1H, J = 9.6 Hz), 4.18(t, 2H, J = 6.6 Hz), 4.13-4.07(m, 1H), 3.14(t, 2H, J = 6.6 Hz), 1.16(d, 3H, J = 6.6 Hz), 0.97(s, 9H) |
| 1-214 | 7.72(d, 2H, J = 8.4 Hz), 7.48(d, 1H, J = 8.7 Hz), 7.35(d, 2H, J = 8.4 Hz), 6.85-6.83(m, 1H), 6.71(dd, 1H, J = 8.7 Hz, 3.0 Hz), 5.90(d, 1H, J = 9.3 Hz), 4.16(t, 2H, J = 6.6 Hz), 4.16-4.05(m, 1H), 3.14(t, 2H, J = 6.6 Hz), 1.16(d, 3H, J = 6.9 Hz), 0.97(s, 9H) |
| 1-218 | 7.71(d, 2H, J = 8.1 Hz), 7.32(d, 2H, J = 8.1 Hz), 7.29-7.22(m, 1H), 6.82-6.77(m, 2H), 6.72(s, 1H), 6.20-6.04(br, 1H), 4.20-4.05(m, 1H), 4.16 (t, 2H, J = 6.6 Hz), 3.12(t, 2H, J = 6.6 Hz), 2.08-1.95(m, 2H), 1.75-1.42 (m, 10H) |
| 1-221 | 7.74(d, 2H, J = 7.8 Hz), 7.34(d, 2H, J = 7.8 Hz), 7.29-7.23(m, 1H), 6.83-6.78(m, 2H), 6.73(s, 1H), 6.41(d, 1H, J = 6.9 Hz), 4.17(t, 2H, J = 6.6 Hz), 3.46-3.35(m, 1H), 3.13(t, 2H, J = 6.6 Hz), 2.97-2.72(m, 5H), 2.65-2.55(m, 1H), 2.05-1.99(m, 1H), 1.80-1.63(m, 3H), 1.57-1.43(m, 1H) |
| 1-231 | 8.60-8.48(m, 2H), 7.86(d, 2H, J = 8.4 Hz), 7.42(d, 2H, J = 8.4 Hz), 7.31-7.24(m, 1H), 7.11-6.70(m, 6H), 4.21(t, 2H, J = 6.6 Hz), 3.93(s, 3H), 3.18(t, 2H, J = 6.6 Hz) |
| 1-233 | 8.28-8.21(m, 2H), 8.11(d, 1H, J = 8.4 Hz), 7.59-7.42(m, 5H), 7.33-7.25 (m, 1H), 6.87-6.81(m, 2H), 6.76(s, 3H), 4.26(t, 2H, J = 6.6 Hz), 3.25(t, 2H, J = 6.6 Hz) |
| 1-241 | 7.85(d, 2H, J = 8.1 Hz), 7.66(s, 1H), 7.48(d, 1H, J = 1.8 Hz), 7.44(d, 2H, J = 8.1 Hz), 7.32-7.25(m, 1H), 6.84-6.80(m, 2H), 6.74-6.73(m, 1H), 6.29(d, 1H, J = 1.8 Hz), 4.21(t, 2H, J = 6.6 Hz), 3.80(s, 3H), 3.19(t, 2H, J = 6.6 Hz) |
| 1-242 | 8.32-8.16(m, 2H), 7.91(d, 2H, J = 8.1 Hz), 7.64-7.61(m, 1H), 7.41(d, 2 H, J = 8.1 Hz), 7.31-7.25(m, 1H), 7.19-7.11(m, 1H), 6.85-6.74(m, 3H), 4.21(t, 2H, J = 6.9 Hz), 3.18(t, 2H, J = 6.9 Hz), 2.34(s, 3H) |
| 1-245 | 8.39-8.32(m, 2H), 7.86(d, 2H, J = 8.4 Hz), 7.68(s, 1H), 7.44(d, 2H, J = 8.4 Hz), 7.31-7.20(m, 3H), 6.85-6.80(m, 2H), 6.75-6.73(m, 1H), 4.22(t, 2H, J = 6.6 Hz), 3.19(t, 2H, J = 6.6 Hz), 2.60(s, 3H) |
| 1-287 | 7.40-6.90(m, 11H), 6.83-6.71(m, 3H), 4.08(t, 2H, J = 6.6 Hz), 3.02(t, 2H, J = 6.6 Hz) |
| 1-288 | 7.50-7.46(m, 2H), 7.32-7.23(m, 3H), 6.94-6.78(m, 2H), 6.75-6.73(m, 1H), 4.40-4.22(m, 1H), 4.17(t, 2H, J = 6.9 Hz), 3.54-3.36(m, 2H), 3.12(t, 2H, J = 6.9 Hz), 2.20-1.52(m, 4H), 1.36(d, 3H, J = 6.0 Hz) |
| 1-289 | 7.38-7.13(m, 5H), 6.84-6.78(m, 2H), 6.75-6.73(m, 1H), 4.17(t, 2H, J = 6.9 Hz), 3.11(t, 2H, J = 6.9 Hz), 3.11-2.89(m, 1H), 1.76-1.36(m, 8H), 1.24(d, 3H, J = 6.9 Hz) |
| 1-290 | 9.20-9.03(br, 1H), 7.93(d, 2H, J = 8.4 Hz), 7.82-7.78(m, 1H), 7.39(d, 2H, J = 8.4 Hz), 7.31-7.16(m, 3H), 6.84-6.74(m, 4H), 4.20(t, 2H, J = 6.6 Hz), 3.85-3.62(br, 1H), 3.17(t, 2H, J = 6.6 Hz), 1.51(s, 9H) |

TABLE 13-continued

| No. | $^1$H-NMR δ ppm<br>Measuring instrument: VARIAN MERCURY plus (300 MHz), Solvent: CDCl$_3$ |
|---|---|
| 1-291 | 9.14-9.05(br, 1H), 7.93(d, 2H, J = 8.4 Hz), 7.83-7.79(m, 1H), 7.39(d, 2H, J = 8.4 Hz), 7.31-7.17(m, 4H), 6.84-6.71(m, 4H), 4.20(t, 2H, J = 6.6 Hz), 3.79-3.70(br, 1H), 3.17(t, 2H, J = 6.6 Hz) |
| 1-292 | 7.30-7.00(m, 9H), 6.80-6.68(m, 2H), 6.67(s, 1H), 4.06(t, 2H, J = 6.9 Hz), 3.38(s, 3H), 2.98(t, 2H, J = 6.9 Hz), 2.21(s, 3H) |
| 1-293 | 8.05(d, 2H, J = 8.4 Hz), 7.39(d, 2H, J = 8.4 Hz), 7.30-7.24(m, 1H), 6.83-6.79(m, 2H), 6.76-6.71(brs, 1H), 5.32(q, 1H, J = 6.9 Hz), 4.20(t, 2H, J = 6.6 Hz), 3.17(t, 2H, J = 6.6 Hz), 2.24(s, 3H), 1.53(d, 3H, J = 6.9 Hz) |
| 1-296 | 7.75(d, 2H, J = 7.8 Hz), 7.34(d, 2H, J = 7.8 Hz), 7.30-7.23(m, 1H), 6.83-6.70(m, 3H), 6.68-6.55(brs, 1H), 5.30-5.18(m, 1H), 5.06-4.95(m, 2H), 4.65-4.56(m, 2H), 4.19(t, 2H, J = 6.6 Hz), 3.15(t, 2H, J = 6.6 Hz) |
| 1-297 | 7.56(d, 2H, J = 8.4 Hz), 7.31-7.04(m, 6H), 6.83-6.66(m, 4H), 4.14(t, 2 H, J = 6.9 Hz), 3.08(t, 2H, J = 6.9 Hz), 2.32(s, 3H), 2.27(s, 3H) |
| 1-326 | 7.72(d, 2H, J = 8.4 Hz), 7.36-7.26(m, 4H), 6.81(dd, 1H, J = 3.0 Hz, 8.7 Hz), 6.12(brs, 1H), 4.14(t, 2H, J = 6.6 Hz), 3.32-3.26(m, 2H), 3.11(t, 2 H, J = 6.6 Hz), 1.95-1.80(m, 1H), 0.98(d, 6H, J = 6.6 Hz) |
| 1-327 | 7.72(d, 2H, J = 8.4 Hz), 7.45(d, 1H, J = 8.7 Hz), 7.36(d, 1H, J = 3.0 Hz), 7.33(d, 2H, J = 8.4 Hz), 6.74(dd, 1H, J = 3.0 Hz, 8.7 Hz), 6.13(brs, 1H), 4.13(t, 2H, J = 6.9 Hz), 3.32-3.26(m, 2H), 3.11(t, 2H, J = 6.9 Hz), 1.97-1.82(m, 1H), 0.98(d, 6H, J = 6.6 Hz) |
| 4-36 | 7.71(d, 2H, J = 8.1 Hz), 7.37-7.26(m, 4H), 7.12-7.00(m, 4H), 6.87-6.83(m, 2H), 6.11-6.02(br, 1H), 4.22(t, 2H, J = 6.9 Hz), 3.80(s, 3H), 3.28(t, 2H, J = 6.9 Hz), 3.15(t, 2H, J = 6.9 Hz), 1.88-1.80(m, 1H), 0.97(d, 6 H, J = 6.9 Hz) |
| 4-37 | 7.72(d, 2H, J = 8.1 Hz), 7.71-7.31(m, 4H), 7.18-7.09(m, 4H), 6.91-6.85(m, 2H), 6.10-6.06(br, 1H), 4.25(t, 2H, J = 6.9 Hz), 3.86(s, 3H), 3.29(t, 2H, 6.9 Hz), 3.16(t, 2H, 6.9 Hz), 1.92-1.87(m, 1H), 0.97(d, 6H, J = 6.9 Hz) |
| 4-75 | 7.72-7.63(m, 3H), 7.51-7.35(m, 5H), 7.13-7.06(m, 3H), 6.98-6.94(m, 1H), 6.11-6.06(br, 1H), 4.26(t, 2H, J = 6.9 Hz), 3.28(t, 2H, J = 6.9 Hz), 3.17(t, 2H, J = 6.9 Hz), 1.92-1.87(m, 1H), 0.97(d, 6H, J = 6.9 Hz) |
| 4-100 | 7.71(d, 2H, J = 8.4 Hz), 7.40-7.09(m, 7H), 6.86-6.80(m, 2H), 6.12(brs, 1H), 4.18(t, 2H, J = 6.6 Hz), 3.33-3.25(m, 2H), 3.13(t, 2H, J = 6.6 Hz), 1.96-1.82(m, 1H), 0.98(d, 6H, J = 6.9 Hz) |
| 4-106 | 7.71(d, 2H, J = 8.1 Hz), 7.41-7.32(m, 5H), 7.14-7.06(m, 2H), 6.83-6.77(m, 2H), 6.14(brs, 1H), 4.18(t, 2H, J = 6.6 Hz), 3.31-3.25(m, 2H), 3.13(t, 2H, J = 6.6 Hz), 1.96-1.82(m, 1H), 0.98(d, 6H, J = 6.6 Hz) |
| 4-109 | 7.71(d, 2H, J = 8.1 Hz), 7.50-7.45(m, 1H), 7.37-7.20(m, 5H), 6.84(dd, 1H, J = 3.0 Hz), 6.79(d, 1H, J = 3.0 Hz), 6.11(brs, 1H), 4.17(t, 2H, J = 6.9 Hz), 3.28(dd, 2H, J = 6.9 Hz, 6.0 Hz), 3.13(t, 2H, J = 6.9 Hz), 1.98-1.82(m, 1H), 0.98(d, 6H, J = 6.6 Hz) |
| 4-115 | 7.71(d, 2H, J = 8.1 Hz), 7.41-7.32(m, 7H), 6.84-6.80(m, 2H), 6.12(brs, 1H), 4.18(t, 2H J = 6.6 Hz), 3.31-3.26(m, 2H), 3.13(t, 2H, J = 6.6 Hz), 1.96-1.82(m, 1H), 0.98(d, 6H, J = 6.6 Hz) |
| 4-182 | 7.72(d, 2H, J = 6.3 Hz), 7.38-7.32(m, 3H), 7.14-6.89(m, 6H), 6.21-6.12(br, 1H), 4.23(t, 2H, J = 6.6 Hz), 3.28(t, 2H, J = 6.6 Hz), 3.16(t, 2H, J = 6.6 Hz), 2.92-1.87(m, 1H), 0.97(d, 6H, J = 6.6 Hz) |
| 4-186 | 7.71(d, 2H, J = 7.8 Hz), 7.47-7.44(m, 1H), 7.37-7.21(m, 5H), 6.18(m, 3 H), 6.19-6.11(br, 1H), 4.21(t, 2H, J = 6.9 Hz), 3.29(t, 2H, J = 6.9 Hz), 3.15(t, 2H, J = 6.9 Hz), 1.97-1.83(m, 1H), 0.97(d, 6H, J = 6.9 Hz) |
| 4-223 | 7.71(d, 2H, J = 8.1 Hz), 7.39-7.32(m, 3H), 7.26-7.00(m, 3H), 6.89-6.80(m, 2H), 6.12(brs, 1H), 4.18(t, 2H, J = 6.6 Hz), 3.31-3.25(m, 2H), 3.14(t, 2H, J = 6.6 Hz), 1.96-1.82(m, 1H), 0.98(d, 6H, J = 6.6 Hz) |
| 4-226 | 7.71(d, 2H, J = 6.9 Hz), 7.36-7.20(m, 4H), 6.98-6.78(m, 4H), 6.12(brs, 1H), 4.18(t, 2H, J = 6.6 Hz), 3.32-3.25(m, 2H), 3.13(t, 2H, J = 6.6 Hz), 1.97-1.82(m, 1H), 0.98(d, 6H, J = 6.6 Hz) |
| 4-229 | 7.71(d, 2H, J = 8.1 Hz), 7.38-7.32(m, 3H), 7.12-6.96(m, 4H), 6.89-6.82(m, 2H), 6.12(brs, 1H), 4.18(t, 2H, J = 6.6 Hz), 3.32-3.25(m, 2H), 3.13(t, 2H, J = 6.6 Hz), 1.97-1.82(m, 1H), 0.98(d, 6H, J = 6.6 Hz) |
| 4-235 | 7.71(d, 2H, J = 8.4 Hz), 7.34(d, 2H, J = 8.4 Hz), 7.27-7.10(m, 4H), 6.85-6.80(m, 2H), 6.12(brs, 1H), 4.18(t, 2H, J = 6.6 Hz), 3.32-3.25(m, 2H), 3.14(t, 2H, J = 6.6 Hz), 1.97-1.82(m, 1H), 0.98(d, 6H, J = 6.6 Hz) |
| 4-328 | 7.71(d, 2H, J = 8.1 Hz), 7.49(d, 1H, J = 1.8 Hz), 7.37-7.16(m, 5H), 6.87(dd, 1H, J = 3.0 Hz, 8.7 Hz), 6.75(d, 1H, J = 3.0 Hz), 6.11(brs, 1H), 4.17(t, 2H, J = 6.6 Hz), 3.31-3.26(m, 2H), 3.13(t, 2H, J = 6.6 Hz), 1.96-1.82(m, 1H), 0.99(d, 6H, J = 6.6 Hz) |
| 4-672 | 7.73(d, 2H, J = 6.3 Hz), 7.38-7.26(m, 3H), 7.03-6.90(m, 5H), 6.21-6.08(br, 1H), 4.23(t, 2H, J = 6.9 Hz), 3.29(t, 2H, J = 6.9 Hz), 3.18(t, 2H, J = 6.9 Hz), 2.05-1.85(m, 1H), 0.97(d, 6H, J = 6.9 Hz) |
| 4-677 | 7.72(d, 2H, J = 8.1 Hz), 7.39-7.26(m, 3H), 7.18-7.13(m, 2H), 7.08-7.05(m, 1H), 6.98-6.97(m, 1H), 6.92-6.89(m, 1H), 6.22-6.19(br, 1H), 4.24(t, 2H, 6.6 Hz), 3.29(t, 2H, 6.6 Hz), 3.17(t, 2H, 6.6 Hz), 1.92-1.63(m, 1H), 0.98(d, 6H, 6.6 Hz) |
| 11-31 | 7.71(d, 2H, J = 8.1 Hz), 7.33(d, 2H, J = 8.1 Hz), 7.24(d, 1H, J = 8.7 Hz), 6.99(d, 1H, J = 3.0 Hz), 6.77(dd, 1H, J = 3.0 Hz, 8.7 Hz), 6.12(brs, 1H), 4.14(t, 2H, J = 6.6 Hz), 3.32-3.26(m, 2H), 3.11(t, 2H, J = 6.6 Hz), 1.98-1.82(m, 1H), 0.98(d, 6H, J = 6.6 Hz), 0.26(s, 9H) |

TABLE 13-continued

| No. | $^1$H-NMR δ ppm<br>Measuring instrument: VARIAN MERCURY plus (300 MHz), Solvent: CDCl$_3$ |
|---|---|
| 1-164 | 7.71(d, 2H, J = 8.4 Hz), 7.34(d, 2H, J = 8.4 Hz), 7.29-7.23(m, 1H), 6.82-6.78(m, 2H), 6.73(s, 1H), 5.93-5.81(br, 1H), 4.35-4.20(m, 1H), 4.17(t, 2H, J = 6.6 Hz), 3.13(t, 2H, J = 6.6 Hz), 1.26(d, 6H, J = 6.6 Hz) |

TABLE 14

| No. | $^1$H-NMR δ ppm<br>Measuring instrument: JEOL-ECX(500 MHz), Solvent: CDCl$_3$ |
|---|---|
| 1-5 | 7.72(d, 2H, J = 8.0 Hz), 7.41(d, 2H, J = 8.0 Hz), 7.35(dd, 1H, J = 8.5, 1.5 Hz), 7.18(dt, 1H, J = 7.5, 1.5 Hz), 6.90-6.87(m, 2H), 6.22-6.19(br, 1H), 4.23(t, 2H, J = 6.0 Hz), 3.29(t, 2H, J = 6.0 Hz), 3.19(t, 2H, J = 6.0 Hz), 1.94-1.86(m, 1H), 0.98(d, 6H, J = 7.0 Hz) |
| 1-6 | 8.71(d, 2H, J = 9.0 Hz), 7.34(d, 2H, J = 9.0 Hz), 7.18(t, 1H, J = 8.0 Hz), 6.92(d, 1H, J = 8.0 Hz), 6.88(t, 1H, J = 2.0 Hz), 6.76(d, 1H, J = 8.0 Hz), 6.18-6.08(br, 1H), 4.17(t, 2H, J = 7.0 Hz), 3.29(t, 2H, J = 7.0 Hz), 3.13(t, 2H, J = 7.0 Hz), 1.94-1.86(m, 1H), 0.98(d, 6H, J = 6.5 Hz) |
| 1-8 | 7.72(d, 2H, J = 8.5 Hz), 7.53(dd, 1H, J = 8.0, 1.5 Hz), 7.43(d, 2H, J = 8.5 Hz), 7.23(dt, 1H, J = 8.0, 1.5 Hz), 6.86-6.81(m, 2H), 6.18-6.08(br, 1H), 4.22(t, 2H, J = 7.0 Hz), 3.29(t, 2H, J = 7.0 Hz), 3.22(t, 2H, J = 7.0 Hz), 1.94-1.86(m, 1H), 0.98(d, 6H, J = 6.5 Hz) |
| 1-12 | 7.71(d, 2H, J = 8.0 Hz), 7.35(d, 2H, J = 8.0 Hz), 7.15(t, 1H, J = 8.0 Hz), 6.76(d, 1H, J = 7.5 Hz), 6.70-6.68(m, 2H), 6.33-6.19(br, 1H), 4.17(t, 2H, J = 6.0 Hz), 3.29(t, 2H, J = 6.0 Hz), 3.12(t, 2H, J = 6.0 Hz), 2.31(s, 3H), 1.94-1.86(m, 1H), 0.98(d, 6H, J = 5.0 Hz) |
| 1-17 | 7.71(d, 2H, J = 8.5 Hz), 7.55(d, 1H, J = 8.0 Hz), 7.45(t, 1H, J = 6.5 Hz), 7.38(d, 2H, J = 8.5 Hz), 6.99(t, 1H, J = 6.5 Hz), 6.94(d, 1H, J = 8.0 Hz), 6.20-6.09(br, 1H), 4.25(t, 2H, J = 6.5 Hz), 3.29(t, 2H, J = 6.5 Hz), 3.17(t, 2H, J = 6.5 Hz), 1.94-1.86(m, 1H), 0.98(d, 6H, J = 7.0 Hz) |
| 1-18 | 7.72(d, 2H, J = 8.0 Hz), 7.39-7.35(m, 3H), 7.19(d, 1H, J = 7.5 Hz), 7.10(s, 1H), 7.04(d, 1H, J = 7.5 Hz), 6.14-6.09(br, 1H), 4.22(t, 2H, J = 5.5 Hz), 3.29(t, 2H, J = 5.5 Hz), 3.16(t, 2H, J = 5.5 Hz), 1.94-1.86(m, 1H), 0.98(d, 6H, J = 6.0 Hz) |
| 1-21 | 7.71(d, 2H, J = 8.5 Hz), 7.35(d, 2H, J = 8.5 Hz), 7.17(t, 1H, J = 8.0 Hz), 6.52-6.48(m, 2H), 6.45(t, 1H, J = 2.5 Hz), 6.19-6.08(br, 1H), 4.17(t, 2H, J = 7.0 Hz), 3.78(s, 3H), 3.29(t, 2H, J = 7.0 Hz), 3.13(t, 2H, J = 7.0 Hz), 1.94-1.86(m, 1H), 0.98(d, 6H, J = 6.5 Hz) |
| 1-23 | 7.71(d, 2H, J = 8.5 Hz), 7.37(d, 2H, J = 8.5 Hz), 7.23-7.20(m, 2H), 6.95-6.92(m, 2H), 6.19-6.09(br, 1H), 4.21(t, 2H, J = 6.5 Hz), 3.29(t, 2H, J = 6.5 Hz), 3.17(t, 2H, J = 6.5 Hz), 1.94-1.86(m, 1H), 0.98(d, 6H, J = 7.0 Hz) |
| 1-25 | 7.72(d, 2H, J = 8.5 Hz), 7.35(d, 2H, J = 8.5 Hz), 7.12(d, 2H, J = 10.0 Hz), 6.86(d, 2H, J = 10.0 Hz), 6.19-6.11(br, 1H), 4.17(t, 2H, J = 7.0 Hz), 3.29(t, 2H, J = 7.0 Hz), 3.14(t, 2H, J = 7.0 Hz), 1.94-1.86(m, 1H), 0.98(d, 6H, J = 6.5 Hz) |
| 1-27 | 7.72(d, 2H, J = 8.0 Hz), 7.52(d, 2H, J = 8.0 Hz), 7.46(s, 1H), 7.37-7.34(m, 2H), 7.09-7.08(m, 1H), 6.18-6.10(br, 1H), 4.18(t, 2H, J = 7.0 Hz), 3.29(t, 2H, J = 7.0 Hz), 3.16(t, 2H, J = 7.0 Hz), 2.60(s, 3H), 1.93-1.86(m, 1H), 0.98(d, 6H, J = 6.5 Hz) |
| 1-69 | 7.72(d, 2H, J = 8.5 Hz), 7.35-7.32(m, 3H), 6.85-6.84(m, 1H), 6.77(dd, 1H, J = 9.5, 3.0 Hz), 6.23-6.11(br, 1H), 4.16(t, 2H, J = 6.5 Hz), 3.29(t, 2H, J = 6.5 Hz), 3.13(t, 2H, J = 6.5 Hz), 1.94-1.86(m, 1H), 0.98(d, 6H, J = 7.0 Hz) |
| 1-72 | 7.73(d, 2H, J = 8.0 Hz), 7.33(d, 2H, J = 8.0 Hz), 6.83(s, 1H), 6.81(t, 1H, J = 2.0 Hz), 6.63(s, 1H), 6.15-6.10(br, 1H), 4.17(t, 2H, J = 7.0 Hz), 3.29(t, 2H, J = 7.0 Hz), 3.14(t, 2H, J = 7.0 Hz), 1.93-1.86(m, 1H), 0.98(d, 6H, J = 7.0 Hz) |
| 1-73 | 7.73(d, 2H, J = 8.5 Hz), 7.33(d, 2H, J = 8.5 Hz), 6.98-6.96(m, 2H), 6.67(s, 1H), 6.17-6.09(br, 1H), 4.16(t, 2H, J = 7.0 Hz), 3.29(t, 2H, J = 7.0 Hz), 3.13(t, 2H, J = 7.0 Hz), 1.94-1.86(m, 1H), 0.98(d, 6H, J = 6.5 Hz) |
| 1-99 | 7.73(d, 2H, J = 8.0 Hz), 7.37(d, 1H, J = 9.0 Hz), 7.34(d, 2H, J = 8.0 Hz), 7.17(d, 1H, J = 3.0 Hz), 6.96(dd, 1H, J = 8.5, 2.5 Hz), 6.19-6.09(br, 1H), 4.19(t, 2H, J = 6.5 Hz), 3.29(t, 2H, J = 6.5 Hz), 3.15(t, 2H, J = 6.5 Hz), 1.94-1.86(m, 1H), 0.98(d, 6H, J = 6.0 Hz) |
| 1-100 | 7.73(d, 2H, J = 7.5 Hz), 7.65(d, 1H, J = 8.5 Hz), 7.34(d, 2H, J = 7.5 Hz), 7.18(d, 1H, J = 3.0 Hz), 6.88(dd, 1H, J = 8.5, 2.5 Hz), 6.19-6.09(br, 1H), 4.19(t, 2H, J = 7.0 Hz), 3.29(t, 2H, J = 7.0 Hz), 3.15(t, 2H, J = 7.0 Hz), 1.94-1.86(m, 1H), 0.98(d, 6H, J = 7.0 Hz) |
| 1-101 | 7.73(d, 2H, J = 8.0 Hz), 7.34(d, 2H, J = 8.0 Hz), 6.91(s, 2H), 6.77-6.74(m, 1H), 6.21-6.08(br, 1H), 4.20(t, 2H, J = 7.0 Hz), 3.29(t, 2H, J = 7.0 Hz), 3.15(t, 2H, J = 7.0 Hz), 1.94-1.86(m, 1H), 0.98(d, 6H, J = 6.0 Hz) |
| 1-102 | 7.74(d, 2H, J = 8.0 Hz), 7.34(d, 2H, J = 8.0 Hz), 7.19(s, 1H), 7.03(s, 1H), 6.99(s, 1H), 6.19-6.08(br, 1H), 4.21(t, 2H, J = 7.0 Hz), 3.29(t, 2H, J = 7.0 Hz), 3.15(t, 2H, J = 7.0 Hz), 1.94-1.86(m, 1H), 0.98(d, 6H, J = 6.5 Hz) |

TABLE 14-continued

| No. | $^1$H-NMR δ ppm<br>Measuring instrument: JEOL-ECX(500 MHz), Solvent: CDCl$_3$ |
|---|---|
| 1-103 | 7.73(d, 2H, J = 8.5 Hz), 7.38-7.31(m, 3H), 7.19(s, 1H), 7.03(s, 1H), 6.22-6.10(br, 1H), 4.20(t, 2H, J = 6.5 Hz), 3.29(t, 2H, J = 6.5 Hz), 3.15(t, 2H, J = 6.5 Hz), 1.94-1.86(m, 1H), 0.98(d, 6H, J = 6.5 Hz) |
| 1-115 | 7.53-7.52(m, 2H), 7.29-7.26(m, 2H), 6.83-6.80(m, 2H), 6.23(s, 1H), 6.13-6.05(br, 1H), 4.16(t, 2H, J = 7.0 Hz), 3.31(t, 2H, J = 7.0 Hz), 3.08(t, 2H, J = 7.0 Hz), 1.96-1.88(m, 1H), 1.00(d, 6H, J = 6.5 Hz) |
| 1-120 | 7.50-7.46(m, 2H), 7.36(t, 1H, J = 7.5 Hz), 7.27(t, 1H, J = 10.0 Hz), 6.81-6.78(m, 2H), 6.73(s, 1H), 6.20-6.10(br, 1H), 4.19(t, 2H, J = 7.0 Hz), 3.28(t, 2H, J = 7.0 Hz), 3.17(t, 2H, J = 7.0 Hz), 1.94-1.86(m, 1H), 0.98(d, 6H, J = 6.5 Hz) |
| 1-121 | 7.79(d, 1H, J = 2.0 Hz), 7.60(dd, 1H, J = 8.0, 2.0 Hz), 7.39(d, 1H, J = 8.0 Hz), 7.27(t, 1H, J = 5.5 Hz), 6.82-6.80(m, 2H), 6.74(s, 1H), 6.22-6.10(br, 1H), 4.20(t, 2H, J = 6.5 Hz), 3.29-3.26(m, 4H), 1.95-1.86(m, 1H), 0.98(d, 6H, J = 6.0 Hz) |
| 1-124 | 7.61(s, 1H), 7.53(dd, 1H, J = 7.5, 2.0 Hz), 7.28-7.25(m, 2H), 6.82-6.79(m, 2H), 6.73(s, 1H), 6.20-6.09(br, 1H), 4.15(t, 2H, J = 7.0 Hz), 3.28(t, 2H, J = 7.0 Hz), 3.14(t, 2H, J = 7.0 Hz), 2.42(s, 3H), 1.94-1.86(m, 1H), 0.98(d, 6H, J = 6.0 Hz) |
| 1-180 | 7.72(d, 2H, J = 8.5 Hz), 7.35(d, 2H, J = 8.5 Hz), 7.24(t, 1H, J = 10.0 Hz), 6.74-6.69(m, 2H), 6.65-6.63(m, 1H), 6.49(t, 1H, J = 74.5 Hz), 6.21-6.18(br, 1H), 4.17(t, 2H, J = 7.0 Hz), 3.29(t, 2H, J = 7.0 Hz), 3.13(t, 2H, J = 7.0 Hz), 1.94-1.86(m, 1H), 0.98(d, 6H, J = 7.0 Hz) |
| 1-182 | 7.74(d, 2H, J = 8.0 Hz), 7.45(s, 1H), 7.36(d, 2H, J = 8.0 Hz), 7.27(s, 2H), 6.18-6.08(br, 1H), 4.27(t, 2H, J = 6.5 Hz), 3.29(t, 2H, J = 6.5 Hz), 3.18(t, 2H, J = 6.5 Hz), 1.94-1.86(m, 1H), 0.98(d, 6H, J = 6.0 Hz) |
| 1-249 | 7.72(d, 2H, J = 8.0 Hz), 7.46(d, 1H, J = 9.0 Hz), 7.33(d, 2H, J = 8.0 Hz), 7.15(d, 1H, J = 3.0 Hz), 6.71(dd, 1H, J = 9.0, 3.0 Hz), 6.19-6.09(br, 1H), 4.15(t.2H, J = 6.0 Hz), 3.29(t, 2H, J = 6.0 Hz), 3.12(t, 2H, J = 6.0 Hz), 1.94-1.86(m, 1H), 0.98(d, 6H, J = 6.5 Hz) |
| 1-30 | 7.71(d, 2H, J = 8.5 Hz), 7.35(d, 2H, J = 8.5 Hz), 7.18(t, 1H, J = 8.0 Hz), 6.83(d, 1H, J = 7.5 Hz), 6.77(t, 1H, J = 2.0 Hz), 6.65(dd, 1H, J = 7.5, 2.0 Hz), 6.19-6.10(br, 1H), 4.18(t, 2H, J = 6.0 Hz), 3.29(t, 2H, J = 6.0 Hz), 3.13(t, 2H, J = 6.0 Hz), 2.46(s, 3H), 1.94-1.86(m, 1H), 0.98(d, 6H, J = 6.0 Hz) |
| 1-36 | 7.72(d, 2H, J = 8.0 Hz), 7.39(t, 1H, J = 8.0 Hz), 7.35(d, 2H, J = 8.0 Hz), 7.23(s, 1H), 7.10(d, 1H, J = 7.5 Hz), 6.98(dd, 1H, J = 7.5, 3.0 Hz), 6.29-6.15(br, 1H), 4.25(t, 2H, J = 6.5 Hz), 3.29(t, 2H, J = 6.5 Hz), 3.15(t, 2H, J = 6.5 Hz), 2.70(s, 3H), 1.94-1.86(m, 1H), 0.98(d, 2H, J = 7.5 Hz) |
| 1-113 | 8.06(t, 1H, J = 8.0 Hz), 7.27(t, 1H, J = 8.0 Hz), 7.19-7.17(m, 1H), 7.08-7.05(m, 1H), 6.83-6.73(m, 4H), 4.19(t, 2H, J = 6.0 Hz), 3.32(t, 2H, J = 6.0 Hz), 3.13(t, 2H, J = 6.0 Hz), 1.95-1.87(m, 1H), 0.98(d, 6H, J = 6.0 Hz) |
| 1-261 | 7.72(d, 2H, J = 6.0 Hz), 7.75(d, 1H, J = 8.5 Hz), 7.34(d, 2H, J = 6.0 Hz), 7.18(d, 1H, J = 3.5 Hz), 6.88(dd, 1H, J = 8.5, 3.5 Hz), 5.96-5.80(br, 1H), 4.19(t, 2H, J = 7.0 Hz), 4.12-4.05(m, 1H), 3.14(t, 2H, J = 7.0 Hz), 1.86-1.76(m, 1H), 1.18(d, 3H, J = 6.0 Hz), 0.97(t, 6H, J = 6.5 Hz) |
| 1-262 | 7.94(d, 1H, J = 8.0 Hz), 7.85(d, 2H, J = 8.0 Hz), 7.71-7.62(br, 1H), 7.56(d, 1H, J = 9.5 Hz), 7.41(d, 2H, J = 8.0 Hz), 7.28-7.22(m, 2H), 7.20(d, 1H, J = 2.5 Hz), 7.12(t, 1H, J = 7.5 Hz), 6.90(dd, 1H, J = 7.6, 2.5 Hz), 4.22(t, 2H, J = 7.0 Hz), 3.18(t, 2H, J = 7.0 Hz), 2.34(s, 3H) |
| 1-263 | 7.72(d, 2H, J = 6.0 Hz), 7.34(d, 2H, J = 6.0 Hz), 7.09(t, 1H, J = 9.5 Hz), 6.81-6.79(m, 1H), 6.78-6.74(m, 1H), 6.00-5.79(br, 1H), 4.14(t, 2H, J = 8.5 Hz), 4.12-4.05(m, 1H), 3.13(t, 2H, J = 8.5 Hz), 1.86-1.77(m, 1H), 1.18(d, 3H, J = 6.5 Hz), 0.97(t, 6H, J = 6.5 Hz) |
| 1-268 | 7.72(d, 2H, J = 9.0 Hz), 7.35(d, 2H, J = 9.0 Hz), 7.20-7.16(m, 1H), 6.64-6.60(m, 1H), 6.18-6.09(br, 1H), 4.23(t, 2H, J = 6.5 Hz), 3.29(t, 2H, J = 6.5 Hz), 3.17(t, 2H, J = 6.5 Hz), 1.94-1.86(m, 1H), 0.98(d, 2H, J = 6.5 Hz) |
| 1-269 | 7.72(d, 2H, J = 6.5 Hz), 7.36(d, 2H, J = 6.5 Hz), 7.21(t, 1H, J = 8.0 Hz), 6.99-6.97(m, 1H), 6.91(t, 1H, J = 2.5 Hz), 6.69(dd, 1H, J = 10.0, 2.5 Hz), 6.19-6.09(br, 1H), 4.19(t, 2H, J = 7.0 Hz), 3.29(t, 2H, J = 7.0 Hz), 3.14(t, 2H, J = 7.0 Hz), 1.92-1.84(m, 1H), 1.30(s, 9H), 0.98(d, 6H, J = 7.5 Hz) |
| 1-271 | 7.70(d, 2H, J = 7.5 Hz), 7.34(d, 2H, J = 7.5 Hz), 7.04(t, 1H, J = 8.0 Hz), 6.31-6.28(m, 2H), 6.22(t, 1H, J = 3.0 Hz), 6.18-6.10(br, 1H), 4.14(t, 2H, J = 7.0 Hz), 3.71-3.60(br, 2H), 3.28(t, 2H, J = 7.0 Hz), 3.11(t, 2H, J = 7.0 Hz), 1.94-1.86(m, 1H), 0.98(d, 6H, J = 7.0 Hz) |
| 1-276 | 7.72(d, 2H, J = 7.0 Hz), 7.34(d, 2H, J = 7.0 Hz), 7.09(t, 1H, J = 9.5 Hz), 6.82-6.74(m, 2H), 6.14-6.05(br, 1H), 4.14(t, 2H, J = 6.5 Hz), 3.43-3.38(m, 1H), 3.30-3.25(m, 1H), 3.13(t, 2H, J = 7.0 Hz), 1.71-1.64(m, 1H), 1.51-1.43(m, 1H), 1.36-1.15(m, 1H), 0.97-0.92(m, 6H) |
| 1-277 | 7.71(d, 2H, J = 7.0 Hz), 7.37-7.33(m, 4H), 6.77-6.75(m, 2H), 6.19-6.05(br, 1H), 4.15(t, 2H, J = 7.0 Hz), 3.43-3.38(m, 1H), 3.30-3.25(m, 1H), 3.12(t, 2H, J = 7.0 Hz), 1.72-1.63(m, 1H), 1.51-1.43(m, 1H), 1.27-1.15(m, 1H), 0.97-0.93(m, 6H) |
| 1-278 | 7.73(d, 2H, J = 8.0 Hz), 7.52(d, 1H, J = 9.5 Hz), 7.33(d, 2H, J = 8.0 Hz) 7.12(d, 1H, J = 2.5 Hz), 6.97(dd, 1H, J = 8.0, 2.5 Hz), 6.18-6.09(br, 1H), 4.18(t, 2H, J = 6.5 Hz), 3.30(t, 2H, J = 6.5 Hz), 3.15(t, 2H, J = 6.5 Hz), 1.93-1.88(m, 1H), 0.98(d, 6H, J = 6.5 Hz) |

TABLE 14-continued

| No. | $^1$H-NMR δ ppm<br>Measuring instrument: JEOL-ECX(500 MHz), Solvent: CDCl$_3$ |
|---|---|
| 1-279 | 8.05(t, 1H, J = 8.0 Hz), 7.27(t, 1H, J = 8.0 Hz), 7.19-7.17(m, 1H), 7.07-7.04(m, 1H), 6.83-6.79(m, 2H), 6.73(s, 1H), 6.61-6.49(br, 1H), 4.18(t, 2H, J = 6.5 Hz), 4.15-4.10(m, 1H), 3.12(t, 2H, J = 6.5 Hz), 1.84-1.79(m, 1H), 1.18(d, 3H, J = 7.0 Hz), 0.96(t, 6H, J = 5.5 Hz) |
| 1-281 | 7.61(d, 2H, J = 8.0 Hz), 7.39(d, 2H, J = 8.0 Hz), 7.27(t, 1H, J = 8.0 Hz), 6.83-6.80(m, 2H), 6.74(s, 1H), 4.21(t, 2H, J = 9.0 Hz), 3.63(d, 2H, J = 9.0 Hz), 3.17(t, 2H, J = 9.0 Hz), 2.15(s, 3H), 2.05-1.98(m, 1H), 0.86(d, 6H, J = 7.0 Hz) |
| 1-282 | 7.59(d, 2H, J = 8.0 Hz), 7.39(d, 2H, J = 8.0 Hz), 7.28(t, 1H, J = 8.0 Hz), 6.82-6.80(m, 2H), 6.74(s, 1H), 4.20(t, 2H, J = 7.0 Hz), 3.21(s, 3H), 3.17(t, 2H, J = 7.0 Hz), 2.33(s, 3H) |
| 1-285 | 7.71(d, 2H, J = 8.0 Hz), 7.35(d, 2H, J = 8.0 Hz), 7.26(t, 1H, J = 9.5 Hz), 6.82-6.80(m, 2H), 6.73(s, 1H), 6.39-6.29(br, 1H), 4.18(t, 2H, J = 9.0 Hz), 3.95-3.63(m, 4H), 3.49(t, 2H, J = 9.0 Hz), 3.14(t, 2H, J = 9.0 Hz), 2.65-2.59(m, 1H), 2.13-2.06(m, 1H), 1.73-1.67(m, 1H) |
| 1-286 | 7.73(d, 2H, J = 7.5 Hz), 7.36-7.33(m, 4H), 7.25(s, 1H), 7.02-6.99(m, 1H), 6.19-6.09(br, 1H), 4.22(t, 2H, J = 7.0 Hz), 3.29(t, 2H, J = 7.0 Hz), 3.16(t, 2H, J = 7.0 Hz), 1.94-1.86(m, 1H), 0.98(d, 6H, J = 6.5 Hz) |
| 1-310 | 7.71(d, 2H, J = 8.5 Hz), 7.35(d, 2H, J = 8.5 Hz), 7.18(t, 1H, J = 8.0 Hz), 6.91(d, 1H, J = 7.5 Hz), 6.84(s, 1H), 6.72(dd, 1H, J = 8.0, 2.5 Hz), 6.34(dd, 1H, J = 8.0 Hz, 2.5 Hz), 6.25-6.19(m, 1H), 6.19-6.08(br, 1H), 4.18(t, 2H, J = 7.0 Hz), 3.29(t, 2H, J = 7.0 Hz), 3.13(t, 2H, J = 7.0 Hz), 1.91-1.86(m, 4H), 0.98(d, 6H, J = 6.5 Hz) |
| 1-316 | 7.71(d, 2H, J = 8.0 Hz), 7.34-7.32(m, 4H), 7.20(t, 1H, J = 9.0 Hz), 7.10(t, 1H, J = 9.0 Hz), 7.01(d, 2H, J = 9.0 Hz), 6.64-6.54(m, 3H), 6.18-6.10(br, 1H), 4.14(t, 2H, J = 6.0 Hz), 3.29(t, 2H, J = 6.0 Hz), 3.11(t, 2H, J = 6.0 Hz), 1.94-1.86(m, 1H), 0.98(d, 6H, J = 7.0 Hz) |
| 4-8 | 7.71(d, 2H, J = 8.0 Hz), 7.51(d, 1H, J = 9.0 Hz), 7.43-7.36(m, 5H), 7.33(d, 2H, J = 8.0 Hz), 6.85(d, 1H, J = 3.0 Hz), 6.75(dd, 1H, J = 8.0, 3.0 Hz), 6.21-6.11(br, 1H), 4.17(t, 2H, J = 7.0 Hz), 3.28(t, 2H, J = 7.0 Hz), 3.13(t, 2H, J = 7.0 Hz), 1.93-1.85(m, 1H), 0.97(d, 6H, J = 8.5 Hz) |
| 4-19 | 7.72(d, 2H, J = 7.0 Hz), 7.40-7.33(m, 5H), 7.27-7.23(m, 1H), 7.16-7.14(m, 1H), 7.08-7.07(m, 1H), 7.05-7.01(m, 1H), 6.91-6.88(m, 1H), 6.18-6.10(br, 1H), 4.25(t, 2H, J = 7.0 Hz), 3.29(t, 2H, J = 7.0 Hz), 3.17(t, 2H, J = 7.0 Hz), 1.94-1.86(m, 1H), 0.98(d, 6H, J = 7.0 Hz) |
| 4-20 | 7.72(d, 2H, J = 7.0 Hz), 7.53-7.49(m, 2H), 7.36(d, 2H, J = 7.0 Hz), 7.32(t, 1H, J = 8.0 Hz), 7.12-7.08(m, 3H), 7.04-7.03(m, 1H), 6.86(dd, 1H, J = 8.0, 3.0 Hz), 6.18-6.09(br, 1H), 4.24(t, 2H, J = 7.0 Hz), 3.28(t, 2H, J = 7.0 Hz), 3.16(t, 2H, J = 7.0 Hz), 1.93-1.85(m, 1H), 0.97(d, 6H, J = 6.5 Hz) |
| 4-21 | 7.71(d, 2H, J = 8.5 Hz), 7.47-7.45(m, 1H), 7.37-7.27(m, 6H), 7.01(d, 1H, J = 8.0 Hz), 6.96(t, 1H, J = 2.5 Hz), 6.91(dd, 1H, J = 8.0, 2.5 Hz), 6.18-6.09(br, 1H), 4.23(t, 2H, J = 7.0 Hz), 3.29(t, 2H, J = 7.0 Hz), 3.15(t, 2H, J = 7.0 Hz), 1.94-1.85(m, 1H), 0.98(d, 6H, J = 6.5 Hz) |
| 4-31 | 7.72(d, 2H, J = 8.0 Hz), 7.38-7.30(m, 6H), 7.17-7.16(m, 2H), 7.09(t, 1H, J = 2.5 Hz), 6.86(dd, 1H, J = 8.0, 2.5 Hz), 6.19-6.11(br, 1H), 4.25(t, 2H, J = 6.5 Hz), 3.29(t, 2H, J = 6.5 Hz), 3.17(t, 2H, J = 6.5 Hz), 2.41(s, 3H), 1.91-1.87(m, 1H), 0.97(d, 6H, J = 6.5 Hz) |
| 4-35 | 7.73(d, 2H, J = 8.5 Hz), 7.69-7.65(m, 4H), 7.38-7.35(m, 3H), 7.18-7.17(m, 1H), 7.09(t, 1H, J = 1.5 Hz), 6.92(dd, 1H, J = 7.5, 1.5 Hz), 6.19-6.09(br, 1H), 4.26(t, 2H, J = 7.0 Hz), 3.29(t, 2H, J = 7.0 Hz), 3.17(t, 2H, J = 7.0 Hz), 1.93-1.86(m, 1H), 0.97(d, 6H, J = 7.0 Hz) |
| 4-180 | 7.72(d, 2H, J = 8.0 Hz), 7.38-7.33(m, 3H), 7.19-7.09(m, 4H), 7.05(s, 1H), 6.92(dd, 1H, J = 8.0, 2.5 Hz), 6.19-6.10(br, 1H), 4.23(t, 2H, J = 9.0 Hz), 3.29(t, 2H, J = 9.0 Hz), 3.16(t, 2H, J = 9.0 Hz), 1.94-1.86(m, 1H), 0.98(d, 6H, J = 7.0 Hz) |
| 4-185 | 7.73(d, 2H, J = 8.5 Hz), 7.38-7.34(m, 3H), 7.13-7.04(m, 4H), 6.91(dd, 1H, J = 8.0, 2.5 Hz), 6.80-6.76(m, 1H), 6.19-6.08(br, 1H), 4.24(t, 2H, J = 7.0 Hz), 3.29(t, 2H, J = 7.0 Hz), 3.17(t, 2H, J = 7.0 Hz), 1.94-1.86(m, 1H), 0.98(d, 6H, J = 8.5 Hz) |
| 4-187 | 7.71(d, 2H, J = 8.0 Hz), 7.48(d, 1H, J = 1.5 Hz), 7.37-7.24(m, 5H), 6.98-6.96(m, 1H), 6.92-6.90(m, 2H), 6.19-6.08(br, 1H), 4.22(t, 2H, J = 7.0 Hz), 3.29(t, 2H, J = 7.0 Hz), 3.15(t, 2H, J = 7.0 Hz), 1.94-1.86(m, 1H), 0.98(d, 6H, J = 7.0 Hz) |
| 4-191 | 7.73(d, 2H, J = 8.0 Hz), 7.43-7.33(m, 6H), 7.10(d, 1H, J = 7.5 Hz), 7.03-7.02(m, 1H), 6.91(dd, 1H, J = 8.5, 2.5 Hz), 6.18-6.08(br, 1H), 4.24(t, 2H, J = 7.0 Hz), 3.29(t, 2H, J = 7.0 Hz), 3.17(t, 2H, J = 7.0 Hz), 1.94-1.86(m, 1H), 0.98(d, 6H, J = 7.0 Hz) |
| 11-1 | 7.69(d, 2H, J = 8.0 Hz), 7.43-7.30(m, 2H), 7.16(t, 1H, J = 8.0 Hz), 7.03(d, 1H, J = 7.5 Hz), 6.95(s, 1H), 6.82(d, 1H, J = 9.0 Hz), 6.14-6.06(br, 1H), 4.15(t, 2H, J = 6.0 Hz), 3.27(t, 2H, J = 6.0 Hz), 3.10(t, 2H, J = 6.0 Hz), 1.91-1.85(m, 1H), 0.96(d, 6H, J = 4.5 Hz), 0.22(s, 9H) |
| 11-2 | 7.71(d, 2H, J = 7.5 Hz), 7.34(d, 2H, J = 7.5 Hz), 7.21(t, 1H, J = 8.0 Hz), 7.08(d, 1H, J = 8.0 Hz), 7.00(t, 1H, J = 1.5 Hz), 6.87(dd, 1H, J = 8.0, 1.5 Hz), 6.21-6.06(br, 1H), 4.17(t, 2H, J = 7.0 Hz), 3.29(t, 2H, J = 7.0 Hz), 3.13(t, 2H, J = 7.0 Hz), 3.05(s, 1H), 1.93-1.86(m, 1H), 0.98(d, 6H, J = 7.0 Hz) |
| 11-11 | 7.71(d, 2H, J = 7.5 Hz), 7.34(d, 2H, J = 7.5 Hz), 7.16(t, 1H, J = 8.0 Hz), 6.98-6.96(m, 1H), 6.90-6.89(m, 1H), 6.80-6.78(m, 1H), 6.19-6.09(br, 1H), |

TABLE 14-continued

| No. | ¹H-NMR δ ppm<br>Measuring instrument: JEOL-ECX(500 MHz), Solvent: CDCl₃ |
|---|---|
|  | 4.17(t, 2H, J = 6.0 Hz), 3.29(t, 2H, J = 6.0 Hz), 3.12(t, 2H J = 6.0 Hz), 1.93-1.86(m, 1H), 1.30(s, 9H), 0.98(d, 6H, J = 6.0 Hz) |
| 11-20 | 7.70(d, 2H, J = 8.0 Hz), 7.33(d, 2H, J = 8.0 Hz), 7.16(t, 1H, J = 8.0 Hz), 6.97(d, 1H, J = 7.0 Hz), 6.91-6.90(m, 1H), 6.80-6.77(m, 1H), 6.18-6.07(br, 1H), 4.16(t, 2H, J = 6.5 Hz), 3.28(t, 2H, J = 6.5 Hz), 3.13(t, 2H, J = 6.5 Hz), 2.58-2.53(m, 1H), 1.93-1.85(m, 3H), 1.75-1.73(m, 3H), 1.54-1.48 (m, 3H), 1.39-1.30(m, 3H), 0.97(d, 6H, J = 6.0 Hz) |
| 4-183 | 7.71(d, 2H, J = 8.0 Hz), 7.37-7.25(m, 4H), 7.05-6.92(m, 5H), 6.17-6.08(br, 1H), 4.22(t, 2H, J = 6.0 Hz), 3.28(t, 2H, J = 6.0 Hz), 3.15(t, 2H, J = 6.0 Hz), 1.94-1.85(m, 1H), 0.98(d, 6H, J = 6.0 Hz) |
| 4-372 | 7.72(d, 2H, J = 7.0 Hz), 7.39-7.28(m, 5H), 7.15-7.09(m, 2H), 7.05-7.03(m, 1H), 6.92(dd, 1H, J = 7.0, 2.5 Hz), 6.16-6.06(br, 1H), 4.23(t, 2H, J = 7.5 Hz), 3.29(t, 2H, J = 7.5 Hz), 3.16(t, 2H, J = 7.5 Hz), 1.94-1.86(m, 1H), 0.98(d, 6H, J = 7.0 Hz) |
| 4-376 | 7.72(d, 2H, J = 8.0 Hz), 7.45-7.27(m, 6H), 7.12-7.10(m, 1H), 7.05-7.03(m, 1H), 6.90(dd, 1H, J = 8.0, 2.5 Hz), 6.18-6.07(br, 1H), 4.24(t,2H, J = 7.0 Hz), 3.29(t, 2H, J = 7.0 Hz), 3.17(t, 2H, J = 7.0 Hz), 1.94-1.86(m, 1H), 0.98(d, 6H, J = 6.5 Hz) |
| 4-377 | 7.73(d, 2H, J = 8.0 Hz), 7.38-7.33(m, 4H), 7.17-7.10(m, 1H), 7.11(d, 1H, J = 8.0 Hz), 7.07-7.05(m, 1H), 7.04-7.03(m, 1H), 6.91(dd, 1H, J = 8.0, 2.5 Hz), 6.19-6.08(br, 1H), 4.24(t, 2H, J = 7.0 Hz), 3.29(t, 2H, J = 7.0 Hz), 3.17(t, 2H, J = 7.0 Hz), 1.94-1.86(m, 1H), 0.98(d, 6H, J = 7.0 Hz) |
| 4-378 | 7.71(d, 2H, J = 8.0 Hz), 7.42-7.32(m, 4H), 7.07-6.91(m, 5H), 6.18-6.09(br, 1H), 4.22(t, 2H, J = 7.0 Hz), 3.29(t, 2H, J = 7.0 Hz), 3.16(t, 2H, J = 7.0 Hz), 1.94-1.86(m, 1H), 0.98(d, 6H, J = 7.0 Hz) |
| 4-380 | 7.71(d, 2H, J = 7.5 Hz), 7.36(d, 2H, J = 7.5 Hz), 7.33-7.24(m, 2H), 7.21(dd, 1H, J = 7.5, 2.5 Hz), 7.04-6.90(m, 1H), 6.19-6.09(br, 4H), 4.22(t, 2H, J = 7.0 Hz), 3.29(t, 2H, J = 7.0 Hz), 3.15(t, 2H, J = 7.0 Hz), 1.94-1.85(m, 1H), 0.97(d, 6H, J = 7.0 Hz) |
| 4-381 | 7.71(d, 2H, J = 7.0 Hz), 7.37-7.32(m, 3H), 7.28-7.24(m, 1H), 7.16-7.11(m, 2H), 7.00(d, 1H, J = 8.5 Hz), 6.95-6.92(m, 2H), 6.17-6.07(br, 1H), 4.23(t, 2H, J = 6.5 Hz), 3.29(t, 2H, J = 6.5 Hz), 3.16(t, 2H, J = 6.5 Hz), 1.94-1.86(m, 1H), 0.98(d, 6H, J = 6.5 Hz) |
| 4-673 | 7.72(d, 2H, J = 7.5 Hz), 7.38-7.32(m, 3H), 7.09(d, 1H. J = 7.5 Hz), 7.03(s, 1H), 6.96-6.89(m, 3H), 6.18-6.07(br, 1H), 4.23(t, 2H, J = 8.0 Hz), 3.29(t, 2H, J = 8.0 Hz), 3.16(t, 2H, J = 8.0 Hz), 1.94-1.86(m, 1H), 0.98(d, 6H, J = 8.0 Hz) |
| 4-676 | 7.71(d, 2H, J = 7.5 Hz), 7.37-7.33(m, 3H), 6.99(d, 1H, J = 7.5 Hz), 6.94-6.92(m, 2H), 6.78-6.72(m, 2H), 6.18-6.07(br, 1H), 4.21(t, 2H, J = 7.0 Hz), 3.29(t, 2H, J = 7.0 Hz), 3.15(t, 2H, J = 7.0 Hz), 1.94-1.86(m, 1H), 0.98 (d, 6H, J = 7.0 Hz) |

TABLE 15

| No. | ¹H-NMR δ ppm<br>Measuring instrument: JEOL-ECX(500 MHz), Solvent: acetone-d6 |
|---|---|
| 4-7 | 7.82(d, 2H, J = 8.5 Hz), 7.70-7.61(br, 1H), 7.45-7.37(m, 8H), 6.96(dd, 1H, J = 7.5, 3.0 Hz), 6.93(d, 1H, J = 3.0 Hz), 3.30(t, 2H, J = 7.0 Hz), 3.19 (t, 2H, J = 7.0 Hz), 3.14(t, 2H, J = 7.0 Hz), 1.92-1.87(m, 1H), 0.92(d, 6H, J = 7.0 Hz) |
| 4-18 | 7.83(d, 2H, J = 7.5 Hz), 7.72-7.67(br, 1H), 7.52-7.49(m, 1H), 7.44-7.35 (m, 4H), 7.26(t, 1H, J = 8.0 Hz), 7.23-7.19(m, 1H), 7.12-7.10(m, 2H), 6.98-6.96(m, 1H), 4.30(t, 2H, J = 7.0 Hz), 3.20(t, 2H, J = 7.0 Hz), 3.16(t, 2H, J = 7.0 Hz), 1.94-1.86(m, 1H), 0.92(d, 6H, J = 9.0 Hz) |
| 4-30 | 7.82(d, 2H, J = 7.0 Hz), 7.72-7.66(br, 1H), 7.42(d, 2H, J = 7.0 Hz), 7.32(t, 1H, J = 8.0 Hz), 7.27-7.16(m, 4H), 6.93-6.91(m, 1H), 6.88-6.85(m, 2 H), 4.29(t, 2H, J = 7.5 Hz), 3.19(t, 2H, J = 7.5 Hz), 3.15(t, 2H, J = 7.5 Hz), 2.23(s, 3H), 1.94-1.85(m, 1H), 0.92(d, 6H, J = 7.0 Hz) |
| 4-33 | 7.83-7.80(m, 3H), 7.70-7.57(m, 3H), 7.44-7.38(m, 3H), 7.32(t, 1H, J = 8.0 Hz), 6.99-6.91(m, 1H), 6.89-6.88(m, 2H), 4.28(t, 2H, J = 7.0 Hz), 3.19(t, 2H, J = 7.0 Hz), 3.14(t, 2H, J = 7.0 Hz), 2.04-1.87(m, 1H), 0.92(d, 6H, J = 7.0 Hz) |
| 4-39 | 7.83(d, 2H, J = 7.5 Hz), 7.74-7.67(br, 1H), 7.53-7.35(m, 6H), 7.12-6.93 (m, 4H), 4.29(t, 2H, J = 7.0 Hz), 3.19(t, 2H, J = 7.0 Hz), 3.16(t, 2H, J = 7.0 Hz), 1.94-1.84(m, 1H), 0.92(d, 6H, J = 7.5 Hz) |
| 11-21 | 7.84(d, 2H, J = 8.0 Hz), 7.75-7.67(br, 1H), 7.54-7.52(m, 2H), 7.44-7.40 (m, 5H), 7.30(t, 1H, J = 8.0 Hz), 7.12-7.08(m, 2H), 6.98-6.96(m, 1H), 4.29(t, 2H, J = 6.0 Hz), 3.20(t, 2H, J = 6.0 Hz), 3.15(t, 2H, J = 6.0 Hz), 1.92-1.86(m, 1H), 0.92(d, 6H, J = 7.0 Hz) |

Now, Test Examples of the present invention will be described.

Test Example 1

Test for Examining Effect on *Haemaphysalis longicornis* (larvae)

A solution prepared so that the concentration of each Invention Compound therein was 100 ppm was used to coat a plastic vial. After the liquid chemical was air-dried, 20 larvae were placed in the vial. This vial was allowed to stand under constant dark conditions at 25° C. and a relative humidity of 80-100%. At 24 hours after the contact with the chemical, the number of dead ticks was recorded. The mortality (%) was determined using the following calculation formula. As a result, Compounds Nos. 1-1, 1-2, 1-3, 1-4, 1-5, 1-6, 1-7, 1-8, 1-9, 1-10, 1-12, 1-13, 1-15, 1-17, 1-18, 1-19, 1-23, 1-24, 1-25, 1-27, 1-48, 1-51, 1-68, 1-69, 1-70, 1-72, 1-73, 1-74, 1-75, 1-80, 1-82, 1-88, 1-95, 1-97, 1-98, 1-99, 1-100, 1-101, 1-102, 1-103, 1-113, 1-115, 1-120, 1-124, 1-128, 1-129, 1-130, 1-131, 1-132, 1-133, 1-135, 1-136, 1-138, 1-142, 1-145, 1-152, 1-156, 1-161, 1-162, 1-163, 1-164, 1-165, 1-167, 1-170, 1-172, 1-177, 1-180, 1-182, 1-183, 1-184, 1-185, 1-186, 1-187, 1-188, 1-189, 1-190, 1-191, 1-192, 1-193, 1-194, 1-195, 1-196, 1-197, 1-198, 1-200, 1-201, 1-202, 1-203, 1-204, 1-205, 1-208, 1-209, 1-210, 1-211, 1-212, 1-213, 1-214, 1-215, 1-217, 1-219, 1-220, 1-222, 1-226, 1-227, 1-229, 1-230, 1-231, 1-233, 1-235, 1-237, 1-239, 1-240, 1-243, 1-246, 1-247, 1-248, 1-249, 1-250, 1-251, 1-252, 1-253, 1-256, 1-257, 1-258, 1-259, 1-260, 1-261, 1-262, 1-263, 1-264, 1-265, 1-266, 1-267, 1-268, 1-269, 1-270, 1-272, 1-273, 1-274, 1-275, 1-276, 1-277, 1-278, 1-279, 1-280, 1-281, 1-285, 1-286, 1-288, 1-289, 1-292, 1-294, 1-295, 1-296, 1-297, 1-298, 1-326, 1-327, 2-1, 2-2, 2-3, 2-4, 4-1, 4-6, 4-7, 4-8, 4-10, 4-18, 4-19, 4-20, 4-21, 4-22, 4-23, 4-25, 4-26, 4-30, 4-31, 4-32, 4-33, 4-34, 4-35, 4-36, 4-37, 4-40, 4-41, 4-76, 4-77, 4-100, 4-106, 4-109, 4-115, 4-180, 4-181, 4-182, 4-183, 4-184, 4-185, 4-186, 4-187, 4-191, 4-223, 4-226, 4-229, 4-235, 4-328, 4-372, 4-373, 4-374, 4-376, 4-377, 4-378, 4-379, 4-380, 4-381, 4-672, 4-673, 4-676, 4-677, 6-1, 6-2, 8-1, 8-2, 9-1, 9-2, 11-1, 11-2, 11-5, 11-11, 11-20, 11-21 and 11-31 showed a mortality of 90% or higher.

Mortality (%)=((number of dead ticks)/(number of all ticks))×100

Formulation examples are given below, when the Invention Compound is used as an agricultural and horticultural insecticide, miticide, nematicide or soil pesticide.

Formulation Example 1

(1) Invention Compound, 20 parts by weight
(2) Clay, 70 parts by weight
(3) White carbon, 5 parts by weight
(4) Sodium polycarboxylate, 3 parts by weight
(5) Sodium alkylnaphthalenesulfonate, 2 parts by weight
The above ingredients are evenly mixed to obtain a wettable powder.

Formulation Example 2

(1) Invention Compound, 5 parts by weight
(2) Talc, 60 parts by weight
(3) Calcium carbonate, 34.5 parts by weight
(4) Liquid paraffin, 0.5 part by weight
The above ingredients are evenly mixed to obtain a dust.

Formulation Example 3

(1) Invention Compound, 20 parts by weight
(2) N,N-dimethylacetamide, 20 parts by weight
(3) Polyoxyethylene tristyrylphenyl ether, 10 parts by weight
(4) Calcium dodecylbenzenesulfonate, 2 parts by weight
(5) Xylene, 48 parts by weight
The above ingredients are evenly mixed and dissolved to obtain an emulsifiable concentrate.

Formulation Example 4

(1) Clay, 68 parts by weight
(2) Sodium ligninsulfonate, 2 parts by weight
(3) Polyoxyethylene alkylaryl sulfate, 5 parts by weight
(4) White carbon, 25 parts by weight
A mixture of the above ingredients is mixed with an Invention Compound in a weight ratio of 4:1 to obtain a wettable powder.

Formulation Example 5

(1) Invention Compound, 50 parts by weight
(2) Sodium alkylnaphthalenesulfonate condensed with formaldehyde, 2 parts by weight
(3) Silicone oil, 0.2 part by weight
(4) Water, 47.8 parts by weight
The above ingredients are evenly mixed and pulverized to obtain a liquid concentrate. Furthermore,
(5) Sodium polycarboxylate, 5 parts by weight and
(6) Anhydrous sodium sulfate, 42.8 parts by weight
are added thereto and evenly mixed. The mixture is granulated and dried to obtain a water dispersible granule.

Formulation Example 6

(1) Invention Compound, 5 parts by weight
(2) Polyoxyethylene octylphenyl ether, 1 part by weight
(3) Polyoxyethylene alkyl ether phosphate, 0.1 part by weight
(4) Particulate calcium carbonate, 93.9 parts by weight
(1) to (3) are evenly mixed beforehand, and this mixture is diluted with an adequate amount of acetone. Thereafter, the diluted mixture is sprayed on (4) and the acetone is removed to obtain granules.

Formulation Example 7

(1) Invention Compound, 2.5 parts by weight
(2) N,N-dimethylacetamide, 2.5 parts by weight
(3) Soybean oil, 95.0 parts by weight
The above ingredients are evenly mixed and dissolved to obtain an ultra low volume formulation.

Formulation Example 8

(1) Invention Compound, 10 parts by weight
(2) Diethylene glycol monoethyl ether, 80 parts by weight
(3) Polyoxyethylene alkyl ether, 10 parts by weight
The above ingredients are evenly mixed to obtain a liquid formulation.

Formulation Examples are given below, when the Invention Compound is used as an agent for controlling animal ectoparasites.

Formulation Example 9

Agent for Transdermal Administration (1) Invention Compound, 1 part by weight
(2) Propylene glycol, 10 parts by weight
(3) 2-Propanol, 89 parts by weight Formulation Example 10

Agent for Transdermal Administration (1) Invention Compound, 5 parts by weight
(2) Hexylene glycol, 50 parts by weight
(3) 2-Propano, 45 parts by weight Formulation Example 11

Agent for Transdermal Administration (1) Invention Compound, 5 parts by weight
(2) Propylene glycol monomethyl ether, 50 parts by weight
(3) Dipropylene glycol, 45 parts by weight Formulation Example 12

Agent for Transdermal Administration (1) Invention Compound, 10 parts by weight
(2) Diethylene glycol monoethyl ether, 90 parts by weight

INDUSTRIAL APPLICABILITY

The compound of the present invention has a high controlling effect against pests, and is useful as a pesticide.

The entire disclosures of Japanese Patent Application No. 2013-172954 filed on Aug. 23, 2013 and Japanese Patent Application No. 2014-101799 filed on May 15, 2014 including specifications, claims and summaries are incorporated herein by reference in their entireties.

The invention claimed is:

1. A phenoxyalkylbenzamide compound represented by the formula (I-5) or its salt:

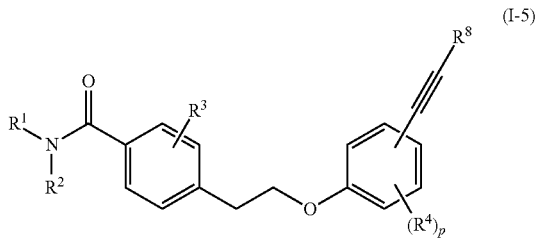

(I-5)

wherein $R^1$ is a hydrogen atom, alkyl, alkenyl, alkynyl, haloalkyl, hydroxyalkyl, alkoxyalkyl, aminoalkyl, alkylaminoalkyl, dialkylaminoalkyl, alkylamino, dialkylamino, mercaptoalkyl, alkylthioalkyl, cyanoalkyl, alkylcarbonylalkyl, Y or alkyl substituted by Y;
Y is an aryl group which may be substituted by Z;
Z is halogen, alkyl, haloalkyl, alkoxy, haloalkoxy, cyano, amino, alkoxycarbonylamino or nitro;
$R^2$ is a hydrogen atom, alkyl, alkylcarbonyl or alkylcarbonylalkyl; or $R^1$ and $R^2$ may form, together with the adjacent nitrogen atom, a cyclic structure which may be substituted by Z, and the cyclic structure may further contain one hetero atom selected from a nitrogen atom which may be substituted by alkyl, an oxygen atom and a sulfur atom;
$R^3$ is a hydrogen atom, halogen, alkyl, haloalkyl, alkylcarbonyl, alkoxycarbonyl, alkoxy, amino, monoalkylamino, dialkylamino, cyano or nitro;
$R^4$ is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano, nitro, phenoxy which may be substituted by $R^9$, phenyl which may substituted by $R^9$, or a pyridyl or thienyl group which may be substituted by $R^9$;
$R^8$ is hydrogen, alkyl, halogen, alkoxy, alkylcarbonyl, alkoxycarbonyl, amino, monoalkylamino, dialkylamino, trialkylsilyl or Y;
$R^9$ is halogen, alkyl, haloalkyl, alkenyl, alkynyl which may be substituted by $R^8$, alkoxy, haloalkoxy, alkylcarbonyl, alkoxycarbonyl, alkylthio, haloalkylthio, alkylsulfinyl, haloalkylsulfinyl, alkylsulfonyl, haloalkylsulfonyl, amino, monoalkylamino, dialkylamino, pentafluorosulfanyl, cyano or nitro; and
p is an integer of from 0 to 4.

2. The compound or its salt according to claim 1, wherein $R^1$ is a hydrogen atom, alkyl, alkenyl, alkynyl, haloalkyl, alkoxyalkyl, dialkylaminoalkyl, di alkylamino, alkylthioalkyl, cyanoalkyl, alkylcarbonylalkyl, Y or alkyl substituted by Y.

3. The compound or its salt according to claim 1, wherein $R^3$ is a hydrogen atom, halogen, alkyl, amino, cyano or nitro.

4. The compound or its salt according to claim 1, wherein $R^4$ is halogen, alkyl, haloalkyl, alkoxy, haloalkoxy, alkylcarbonyl, alkylthio, haloalkylthio, alkylsulfinyl, alkylsulfonyl, amino, dialkylamino, cyano, nitro or phenoxy which may be substituted by $R^9$.

5. A pesticidal composition containing the compound or its salt as defined in claim 1, as an active ingredient.

6. An insecticidal composition containing the compound or its salt as defined in claim 1, as an active ingredient.

7. A method for controlling pests, which comprises applying an effective amount of the compound or its salt as defined in claim 1 to the pests.

8. The compound or its salt according to claim 1, wherein $R^1$ is $CH(CH_3)CH(CH_3)_2$, $R^2$ is H, $R^3$ is H, $R^8$ is $C(CH_3)_3$ and p =0.

9. The compound or its salt according to claim 8, which is represented by the formula (I-5b):

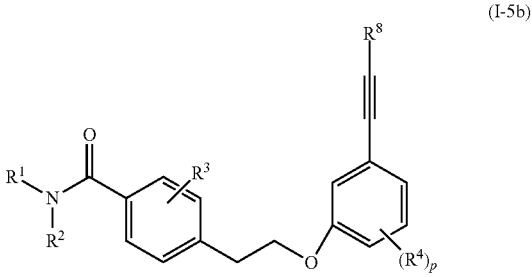

(I-5b)

wherein $R^1 R^2$, $R^3$, $R^8$ and p are as defined in claim 8.

10. The compound or its salt according to claim 1, wherein $R^1$ is
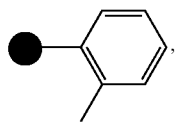
$R^2$ is H, $R^3$ is H, $R^8$ is $C(CH_3)_3$ and p =0.
11. The compound or its salt according to claim 10, which is represented by the formula (I-5b):
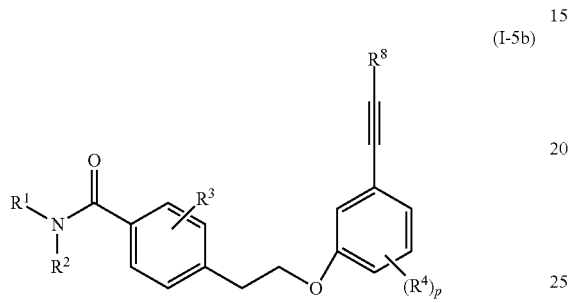
wherein $R^1, R^2, R^3, R^8$ and p are as defined in claim 10.
* * * * *

UNITED STATES PATENT AND TRADEMARK OFFICE
CERTIFICATE OF CORRECTION

PATENT NO. : 10,299,475 B2
APPLICATION NO. : 14/911642
DATED : May 28, 2019
INVENTOR(S) : Higuchi et al.

Page 1 of 1

It is certified that error appears in the above-identified patent and that said Letters Patent is hereby corrected as shown below:

In the Claims

Column 128, Line 31, Claim 2, Line 3, "di alkylamino" should be --dialkylamino--.

Signed and Sealed this
Fifth Day of November, 2019

Andrei Iancu
*Director of the United States Patent and Trademark Office*